(12) United States Patent
Castanedo et al.

(10) Patent No.: US 8,563,540 B2
(45) Date of Patent: Oct. 22, 2013

(54) PYRIDO[3,2-D]PYRIMIDINE PI3K DELTA INHIBITOR COMPOUNDS AND METHODS OF USE

(71) Applicant: Genetech, Inc., South San Francisco, CA (US)

(72) Inventors: Georgette Castanedo, Redwood City, CA (US); Bryan Chan, San Carlos, CA (US); Matthew C. Lucas, Nutley, NJ (US); Brian Safina, Redwood City, CA (US); Daniel P. Sutherlin, Burlingame, CA (US); Zachary Sweeney, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/854,635

(22) Filed: Apr. 1, 2013

(65) Prior Publication Data
US 2013/0225557 A1 Aug. 29, 2013

Related U.S. Application Data

(62) Division of application No. 13/030,246, filed on Feb. 18, 2011, now Pat. No. 8,440,651.

(60) Provisional application No. 61/306,751, filed on Feb. 22, 2010.

(51) Int. Cl.
*A61K 31/397* (2006.01)
*A61K 31/5377* (2006.01)
*C07D 413/14* (2006.01)

(52) U.S. Cl.
USPC ............... 514/210.21; 514/234.2; 514/232.5; 544/117; 544/82

(58) Field of Classification Search
USPC .......... 544/117, 82; 514/210.21, 234.2, 232.5
See application file for complete search history.

(56) References Cited

U.S. PATENT DOCUMENTS

| | | | |
|---|---|---|---|
| 3,843,638 A | 10/1974 | Nicki et al. | |
| 3,939,268 A | 2/1976 | Nickl et al. | |
| 7,615,552 B2 | 11/2009 | Ono et al. | |
| 8,067,586 B2 | 11/2011 | Hayakawa et al. | |
| 2008/0004285 A1 | 1/2008 | De Jonghe et al. | |
| 2009/0036430 A1 | 2/2009 | De Jonghe et al. | |
| 2009/0324543 A1 | 12/2009 | Watkins et al. | |

FOREIGN PATENT DOCUMENTS

| | | |
|---|---|---|
| JP | 7005594 | 1/1995 |
| WO | 2009/039140 A1 | 3/2009 |
| WO | 2009/100406 A2 | 8/2009 |
| WO | 2009/157880 A1 | 12/2009 |
| WO | 2010/037765 | 4/2010 |

OTHER PUBLICATIONS

Hayakawa et al., "Synthesis and biological evaluation of 4-morpholino-2- phenylquinazolines and related derivatives as novel PI3 kinase p110α inhibitors" Bioorganic & Medicinal Chemistry 14:6847-6858 ( 2006).

Jager et al., "Die forlaufende Messung der Plättchenaggregation ohne Zugabe von Aggregationsauslösern. II. Experimentelle Befunde und Prüfung von Aggregationshemmern " Blut (English summary), 29(4):251-9 ( 1974).

Jennes et al., "The Effect of Acetyl-Salicylic-Acid and a Pyrido-Pyrimidine-Derivate on the Rejection of Allotransplanted Canine Kidneys" Res. exp. Med. 165:67-73 ( 1975).

Maira et al., "PI3K inhibitors for cancer treatment: where do we stand?" Biochem. Soc. Trans. 37:265-272 ( 2009).

Malagu et al., "The discovery and optimisation of pyrido[2,3-d]pyrimidine-2,4-diamines as potent and selective inhibitors of mTOR kinase" Bioorganic & Medicinal Chemistry Letters 19:5950-5953 ( 2009).

Nishikawa et al., "Structure-Activity Relationships of the Diuretic Activity of Triaza- and Tetraaza-naphthalene Compounds" Chem. Pharm. Bull. 24(9):2057-2077 ( 1976).

Srinivasan et al., "Pyridopyrimidines. 12. Synthesis of 8-Deaza Analogues of Aminopterin and Folic Acid" J. Org. Chem. 46:1777-1781 ( 1981).

*Primary Examiner* — Kristin Vajda
(74) *Attorney, Agent, or Firm* — Alex Andrus; Genentech, Inc.

(57) ABSTRACT

Formula I compounds, including stereoisomers, geometric isomers, tautomers, metabolites and pharmaceutically acceptable salts thereof, are useful for inhibiting the delta isoform of PI3K, and for treating disorders mediated by lipid kinases such as inflammation, immunological disorders, and cancer. Methods of using compounds of Formula I for in vitro, in situ, and in vivo diagnosis, prevention or treatment of such disorders in mammalian cells, or associated pathological conditions, are disclosed.

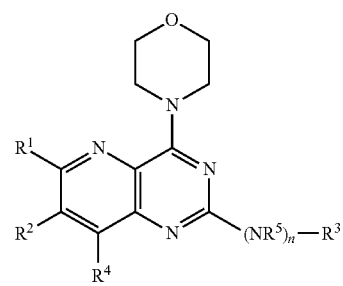

9 Claims, No Drawings

PYRIDO[3,2-D]PYRIMIDINE PI3K DELTA INHIBITOR COMPOUNDS AND METHODS OF USE

CROSS REFERENCE TO RELATED APPLICATIONS

This application is a divisional of U.S. Ser. No. 13/030,246 filed on 18 Feb. 2011, and claims the benefit under 35 USC §119(e) of U.S. Provisional Application Ser. No. 61/306,751 filed on 22 Feb. 2010, which are each incorporated by reference in their entirety.

FIELD OF THE INVENTION

The invention relates generally to compounds for treating disorders mediated by lipid kinases such as inflammation, immunological, and cancer, and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (PI), a phospholipid found in cell membranes, plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of the inositol ring of phosphoinositols (Whitman et al (1988) Nature, 332: 664). The 3'-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41). PI3K inhibition is a promising mechanism for targeted therapies for cancer treatment (Maira et al (2009) Biochem. Soc. Trans. 37:265-272).

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct.

The p110 delta isoform has been implicated in biological functions related to immune-inflammatory diseases, including signaling from the B-cell receptor, T cell receptor, FcR signaling of mast cells and monocyte/macrophage, and osteoclast function/RANKL signaling (Deane J and Fruman D A (2004) Annu. Rev. Immunol. 2004. 22:563-98; Janas et al., The Journal of Immunology, 2008, 180: 739-746; Marone R et al., Biochim. Biophy. Acta 2007, 1784:159-185). Deletion of the PI3K delta gene or selective introduction of a catalytically inactive mutant of PI3K delta causes a nearly complete ablation of B cell proliferation and signaling, and impairment of signaling through T cells as well.

SUMMARY OF THE INVENTION

The invention relates to pyrido[3,2-d]pyrimidine Formula I compounds with PI3 kinase inhibitory activity and selective binding to the p110 delta isoform relative to binding to the p110 alpha isoform.

Formula I compounds have the structures:

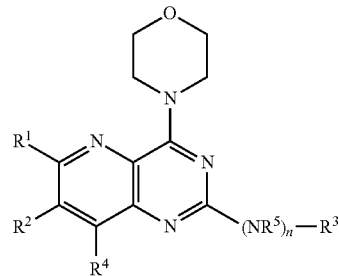

I and stereoisomers, geometric isomers, tautomers, or pharmaceutically acceptable salts thereof. The various substituents, including $R^1$, $R^2$, $R^3$, $R^4$, and $R^5$, are as defined herein.

Another aspect of the invention provides a pharmaceutical composition comprising a Formula I compound and a pharmaceutically acceptable carrier, glidant, diluent, or excipient.

The invention also relates to methods of using the Formula I compounds for in vitro, in situ, and in vivo diagnosis or treatment of mammalian cells, organisms, or associated pathological conditions, such as cancer, systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Another aspect of the invention provides a method of treating a disease or disorder which method comprises administering a Formula I compound to a patient with a disease or disorder selected from cancer, immune disorders, cardiovascular disease, viral infection, inflammation, metabolism/endocrine function disorders and neurological disorders, and mediated by the p110 delta, beta, or alpha isoform of PI3 kinase. The method may further comprise administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

Another aspect of the invention provides a kit for treating a condition mediated by the p110 delta isoform of PI3 kinase, comprising a pharmaceutical composition of a Formula I compound; and instructions for use.

Other aspects of the invention include: (i) method for preventing or treating conditions, disorders or diseases mediated by the activation of the PI3K kinase enzyme, in a subject in need of such treatment, which method comprises administering to said subject an effective amount of a compound of Formula I or a pharmaceutically acceptable salt thereof, in free form or in a pharmaceutically acceptable salt form as a pharmaceutical, in any of the methods as indicated herein; (ii) a compound of the Formula I in free form or in pharmaceutically acceptable salt form for use as a pharmaceutical in any of the methods described herein, in particular for the use in one or more phosphatidylinositol 3-kinase (PI3K) mediated diseases; (iii) the use of a compound of Formula I in free form or in pharmaceutically acceptable salt form in any of the methods as indicated herein, in particular for the treatment of one or more phosphatidylinositol 3-kinase mediated diseases; (iv) the use of a compound of Formula I in free form or in pharmaceutically acceptable salt form in any of the methods as indicated herein, in particular for the manufacture of a medicament for the treatment of one or more phosphatidylinositol 3-kinase mediated diseases.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═$CH_2$), allyl (—$CH_2$CH═$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, independently with one or more substituents described herein and includes radicals having "cis" and "trans" orientations, or alternatively, "E" and "Z" orientations. Examples include, but are not limited to, ethylenylene or vinylene (—CH═CH—), allyl (—$CH_2$CH═CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modem Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 3-azabicyclo [3.1.0]hexanyl, 3-azabicyclo[4.1.0]heptanyl, azabicyclo [2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, benzimidazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafamib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, 11), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclophosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; (ix) topoisomerase 1 inhibitors such as LURTOTECAN®; ABARELIX® rmRH; (x) anti-angiogenic agents such as bevacizumab (AVASTIN®, Genentech); (xi) alkylating agents such as VNP-40101M or cloretizine, oxaliplatin (U.S. Pat. No. 4,169,846, WO 03/24978m WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine), brostallicin, mitomycin C (MitoExtra), TLK-286 (TELCYTA™), temozolomide, trabectedin (U.S. Pat. No. 5,478,932), AP-5280 (Platinate formulation of Cisplatin), porfiromycin, and clearazide (meclorethamine); (xii) chelating agents including tetrathiomolybdate (WO 01/60814), RP-697, Chimeric T84.66 (cT84.66), gadofosveset (VASOVIST™), deferoxamine, and bleomycin optionally in combination with electroporation; (xiii) anti-cancer vaccines including AVICINE™ (Tetrahedron Lett. 26:2269-70 (1974)), oregovomab (OVAREX™), THERATOPE™ (STn-KLH), Melanoma Vaccines, GI-4000 series (GI-4014, GI-4015, and GI-4016), directed to mutations in the Ras protein, GlioVax-1, MelaVax, Advexin™ or INGN-201 (WO 95/12660), Sig/E7/LAMP-1, encoding HPV-16 E7, MAGE-3 Vaccine or M3TK (WO 94/05304), HER-2VAX, ACTIVE which stimulates T-cells specific for tumors, GM-CSF cancer vaccine, ICT-107 (ImmunoCellular Therapeutics), and Listeria monocytogenes-based vaccines; and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula I, such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Certain structures may exist as geometric isomers (i.e. cis and trans isomers), tautomers, or atropisomers.

Any formula given herein is also intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as 2H (deuterium), 3H (tritium), 11C, 13C, 14C, 15N, 31P, 32P, .sup.18F 35S, 36Cl, 125I respectively. Various isotopically labeled compounds of the present invention, for example those into which radioactive isotopes such as 3H, 13C, and 14C are incorporated. Such isotopically labelled compounds are useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. In particular, an 18F or labeled compound may be particularly preferred for PET or SPECT studies. Further, substitution with heavier isotopes such as deuterium may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

Pyrido[3,2-d]Pyrimidine Formula I Compounds

Formula I compounds include compounds having the formula:

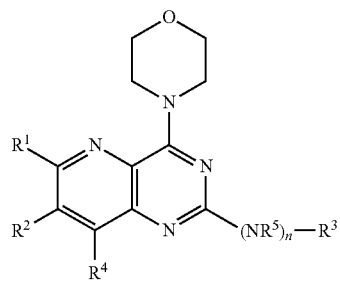

I and stereoisomers, geometric isomers, tautomers, or pharmaceutically acceptable salts thereof, wherein $R^1$ is selected from H, F, Cl, Br, I, $N(R^2)_2$, $OR^2$, $SR^2$, $SOR^2$, $SO_2R^2$, $SO_2N(R^2)_2$, $C_1$-$C_{12}$ alkyl,
$C_2$-$C_8$ alkenyl,
$C_2$-$C_8$ alkynyl,
$C_6$-$C_{20}$ aryl,
$C_3$-$C_{12}$ carbocyclyl,
$C_2$-$C_{20}$ heterocyclyl,
$C_1$-$C_{20}$ heteroaryl,
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)-C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)-N($R^2$)$_2$,
—($C_1$-$C_{12}$ alkylene)-$NR^2$C(=O)$R^2$,
—($C_1$-$C_{12}$ alkylene)-$NR^2$—($C_1$-$C_{12}$ alkyl),
—($C_1$-$C_{12}$ alkylene)-N($C_1$-$C_{12}$ alkyl)($C_2$-$C_{20}$ heterocyclyl),
—($C_1$-$C_{12}$ alkylene)-$NR^2$—($C_1$-$C_{12}$ alkylene)-($C_1$-$C_{20}$ heteroaryl),
—($C_1$-$C_{12}$ alkylene)-$NR^2$—($C_1$-$C_{12}$ alkylene)-($C_1$-$C_{20}$ heterocyclyl),
—($C_1$-$C_{12}$ alkylene)-$NR^2$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-N($C_1$-$C_{12}$ alkyl)$R^2$,
—($C_1$-$C_{12}$ alkylene)-($C_2$-$C_{20}$ heterocyclyl)-($C_1$-$C_{12}$ alkyl)-N($C_1$-$C_{12}$ alkyl)$R^2$,
—($C_1$-$C_{12}$ alkylene)-$NR^2$—($C_2$-$C_{20}$ heterocyclyl),
—($C_2$-$C_{12}$ alkenylene)-($C_2$-$C_{20}$ heterocyclyl),
—($C_2$-$C_{20}$ heterocyclyl)-($C_1$-$C_{12}$ alkyl),
—$NR^2$—($C_2$-$C_{20}$ heterocyclyl),
—C(=O)—($C_2$-$C_{20}$ heterocyclyl), and
—C(=O)—($C_1$-$C_{12}$ alkyl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2CH_3$, —$CH_2CH(CH_3)_2$, —$CH_2OH$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —CN, —$CF_3$, —$CHF_2$, —$CO_2H$, —$COCH_3$, —$CO_2CH_3$, —$C(CH_3)_2CO_2CH_3$, —$CO_2C(CH_3)_3$, —$COCH(OH)CH_3$, —$COCH(CH_3)_2$, —$CONH_2$, —$CONHCH_3$, —$CON(CH_3)_2$, —$C(CH_3)_2CONH_2$, —$NO_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, =O, —OH, —$OCH_3$, —$S(O)_2N(CH_3)_2$, —$SCH_3$, —$CH_2OCH_3$, —$S(O)_2CH_3$, cyclopropyl, oxetanyl, and morpholino;

$R^2$ and $R^4$ are independently selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$COC(CH_3)_3$, —$COCF_3$, —$CH_2CF_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$OCH_2CH_3$, —$OCH(CH_3)_2$, —$S(O)_2N(CH_3)_2$, —$SCH_3$, —$CH_2OCH_3$, and —$S(O)_2CH_3$;

$R^3$ is selected from $C_6$-$C_{20}$ aryl, $C_2$-$C_{20}$ heterocyclyl and $C_1$-$C_{20}$ heteroaryl, each of which are optionally substituted with one or more groups independently selected from F, Cl, Br, I, —$CH_3$, —$CH_2CH_3$, —$CH(CH_3)_2$, —$CH_2CN$, —CN, —$CHF_2$, —$CF_3$, —$CH_2CF_3$, —$CF_2CH_3$, —$CH_2OH$, —$CH_2CH_2OH$, —$CH(CH_3)OH$, —$CH(CH_3)OCH_3$, —$CO_2H$, —$CONH_2$, —$CON(CH_3)_2$, —$NO_2$, —$NH_2$, —$NHCH_3$, —$N(CH_3)_2$, —$NHCOCH_3$, —OH, —$OCH_3$, —SH, —NHC(=O)$NHCH_3$, —NHC(=O)$NHCH_2CH_3$, —$S(O)_2CH_3$, cyclopropyl, pyrrolidin-1-yl, 3-methoxyazetidin-1-yl, and azetidin-1-yl;

$R^5$ is selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C (=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

and n is 0 or 1.

Further it is to be understood that every embodiment relating to a specific residue $R^1$, $R^2$, $R^3$, $R^4$ and $R^5$ as disclosed herein may be combined with any other embodiment relating to another residue $R^1$, $R^2$, $R^3$, $R^4$ and $R^5$ as disclosed herein.

Exemplary embodiments of Formula I compounds include wherein $R^1$ is selected from the structures

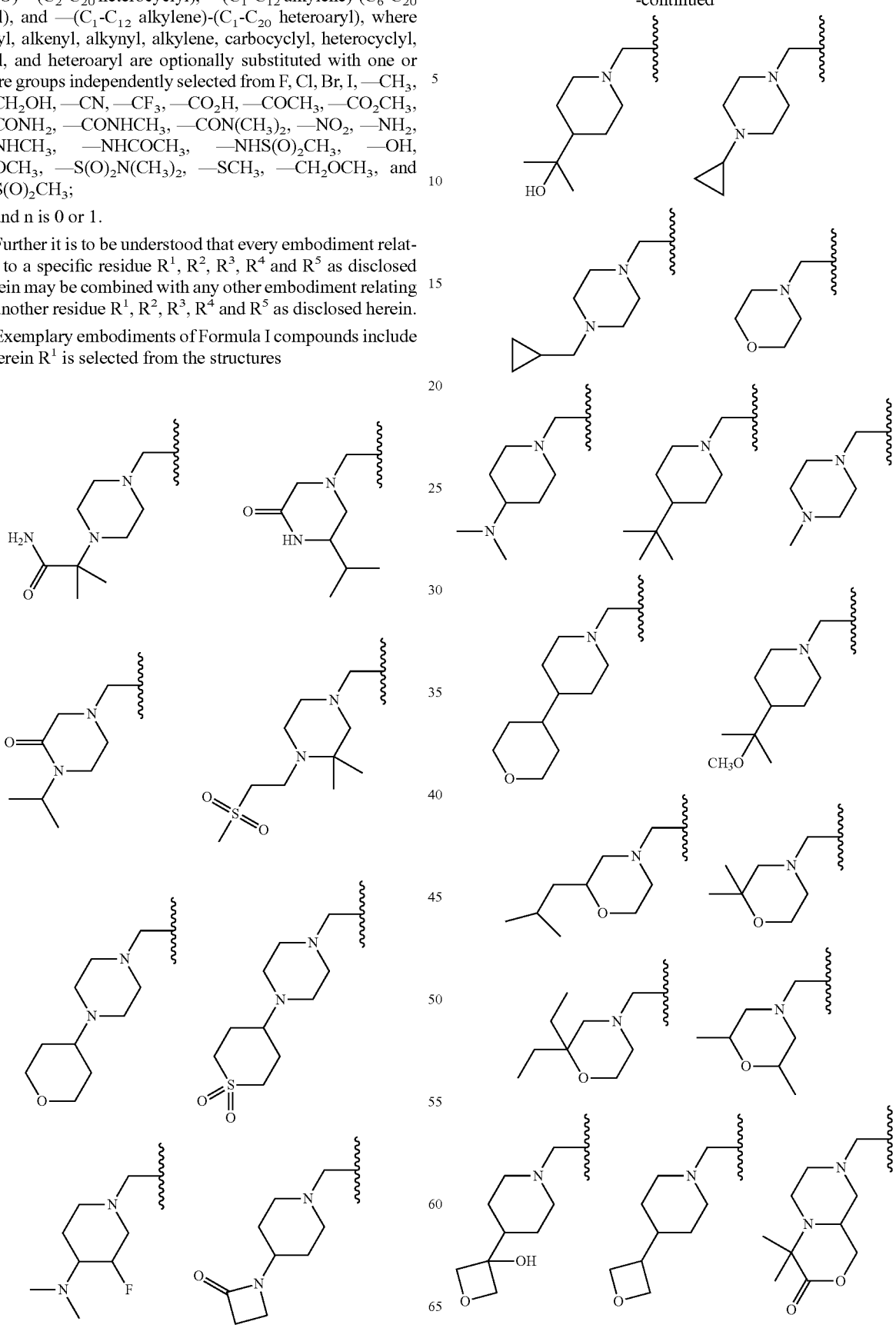

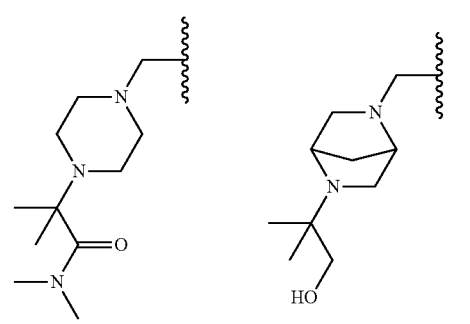
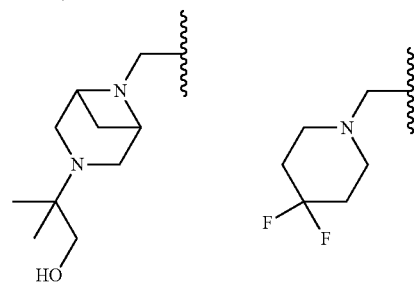
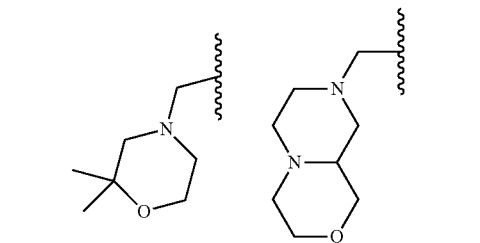
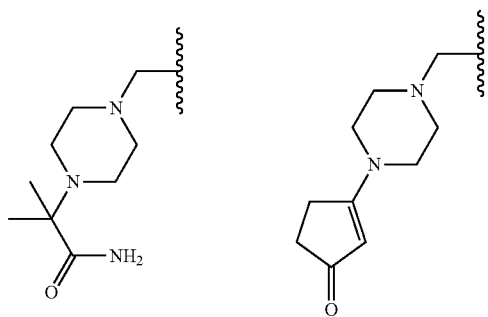
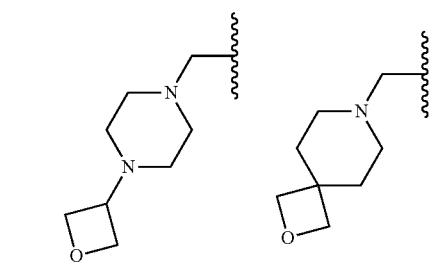
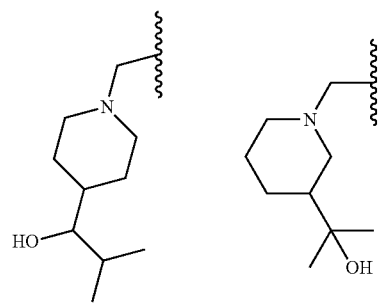
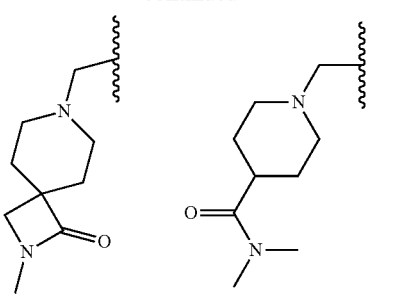
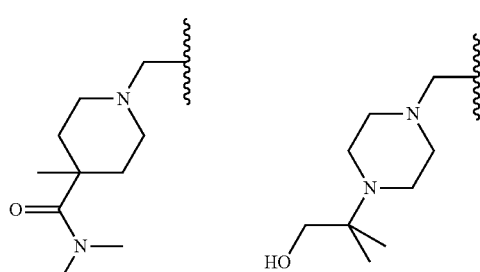
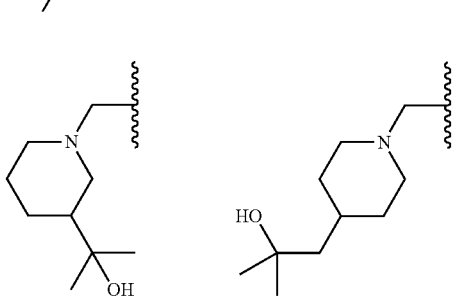
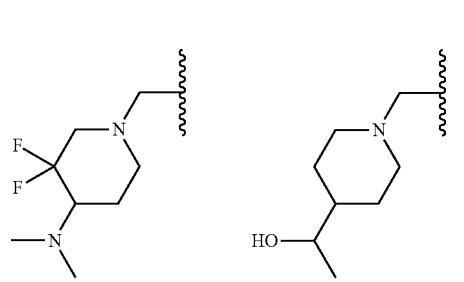
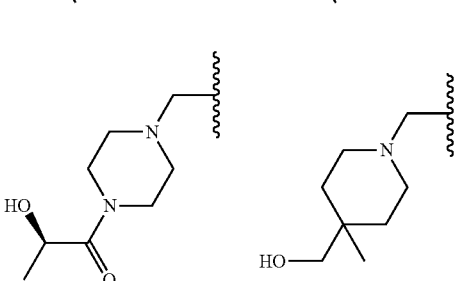
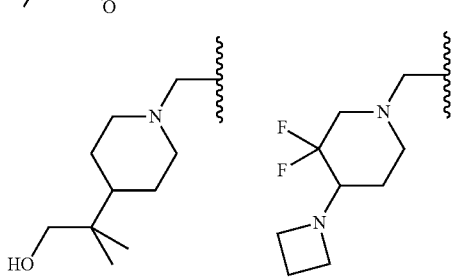

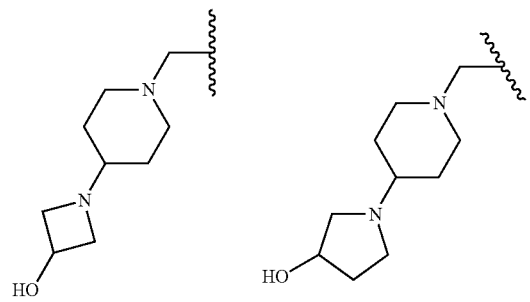
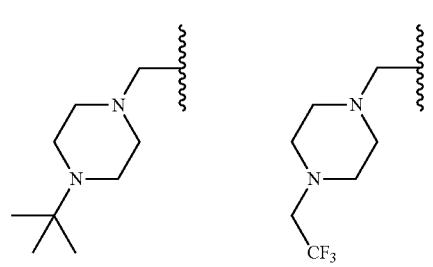
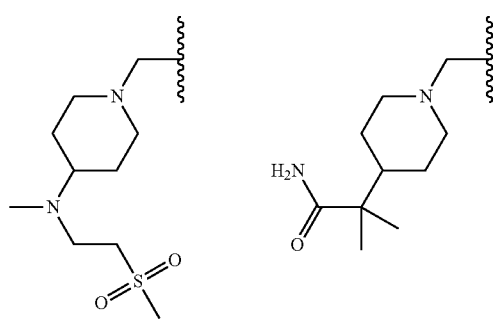
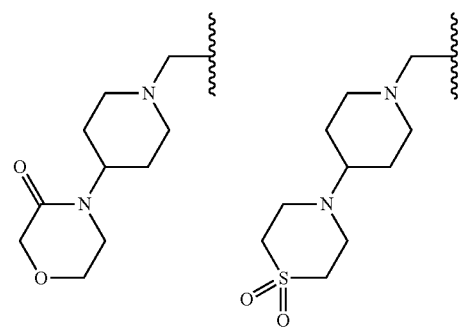
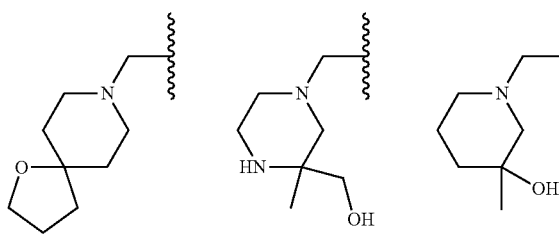
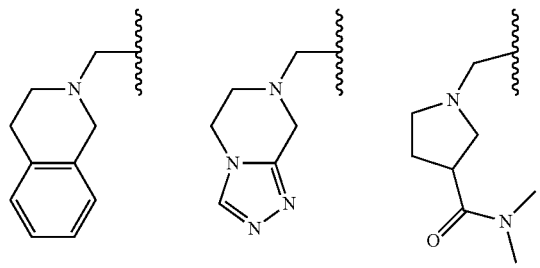
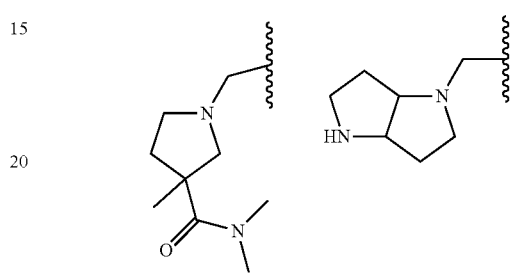
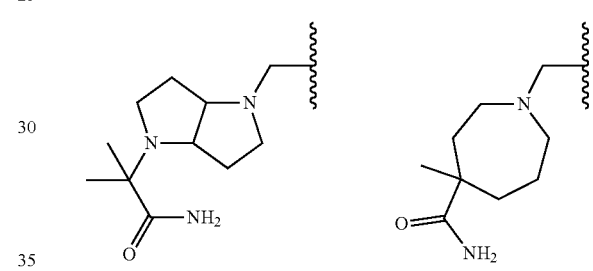
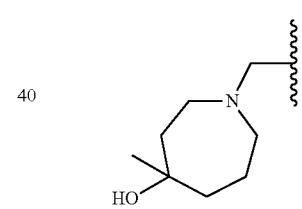
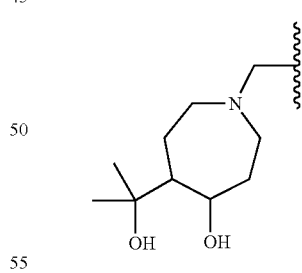
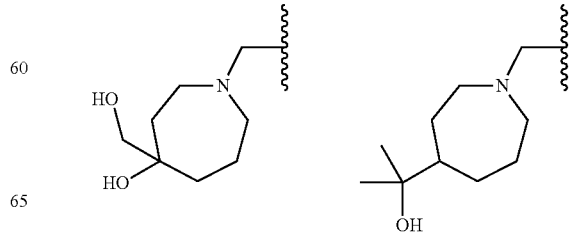

23
-continued
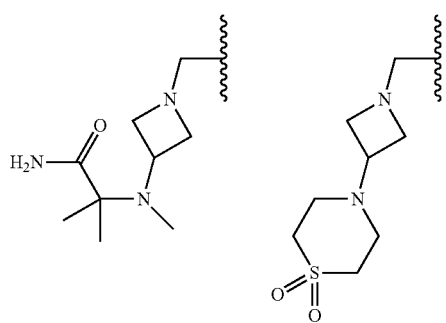
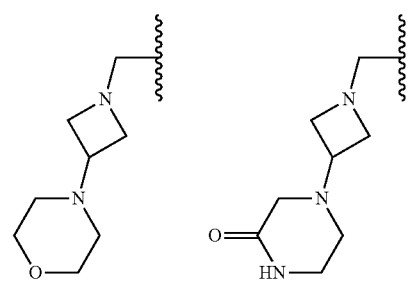
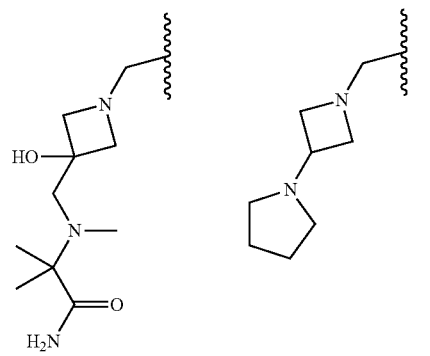
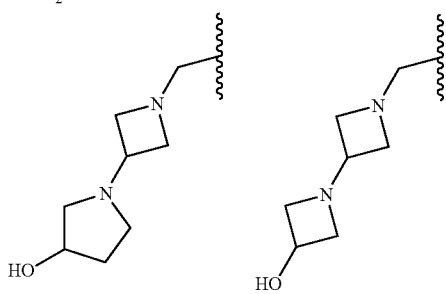
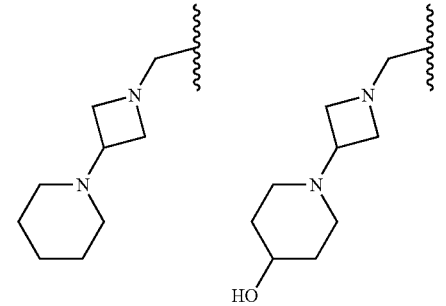
24
-continued
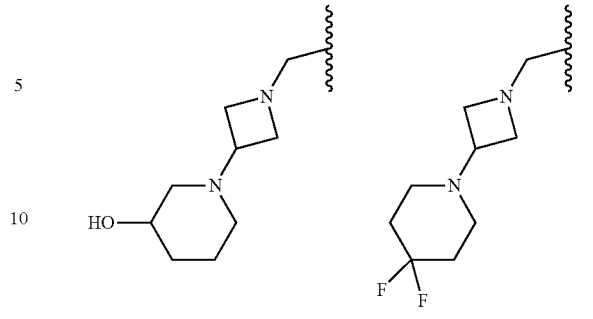
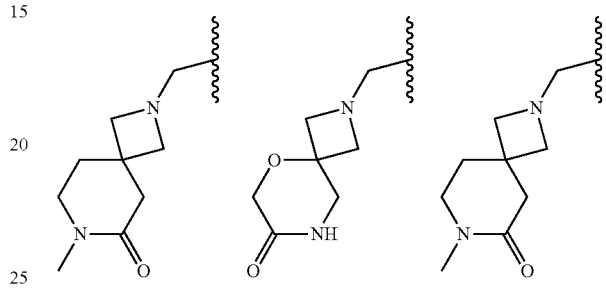
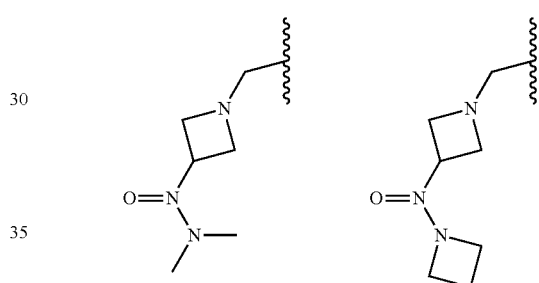
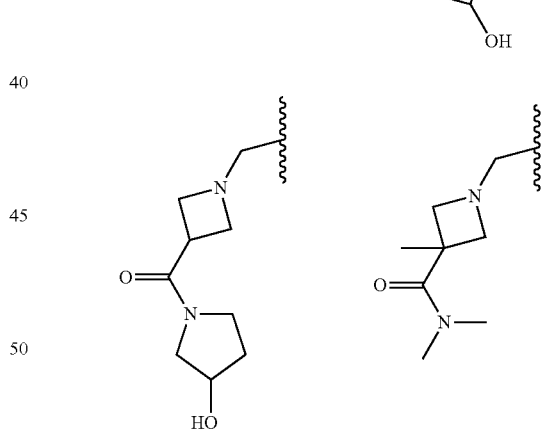
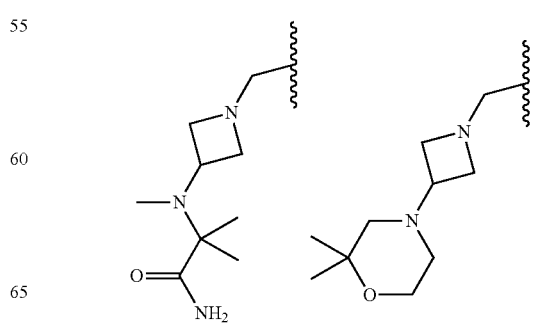

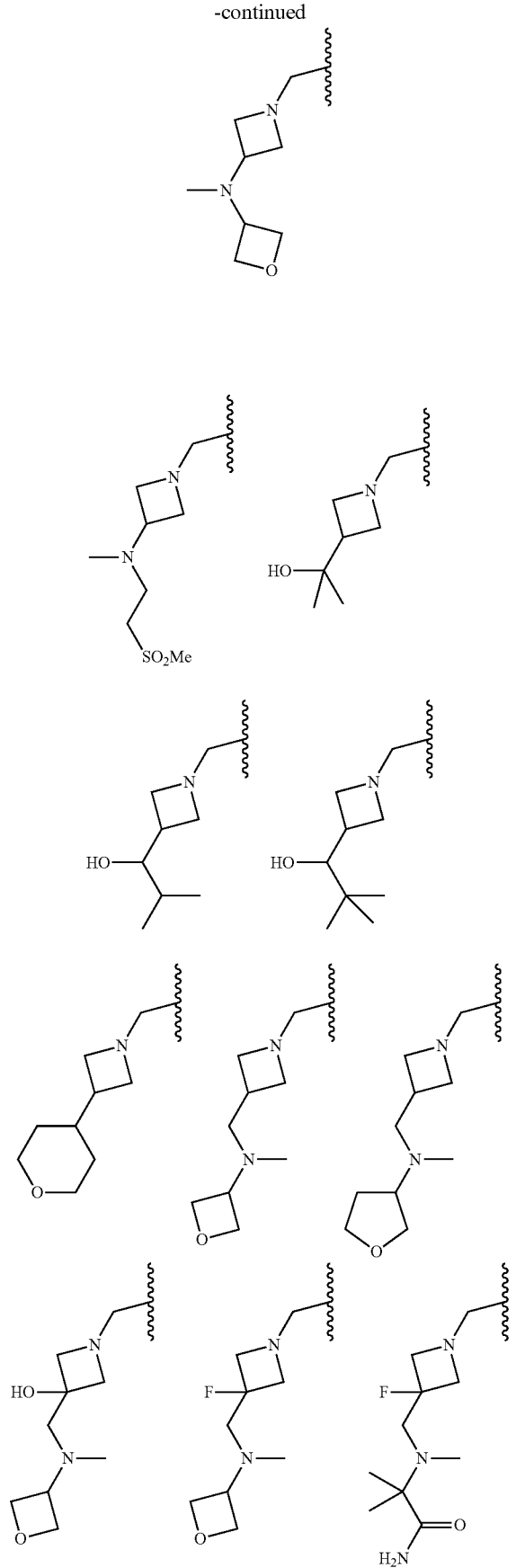
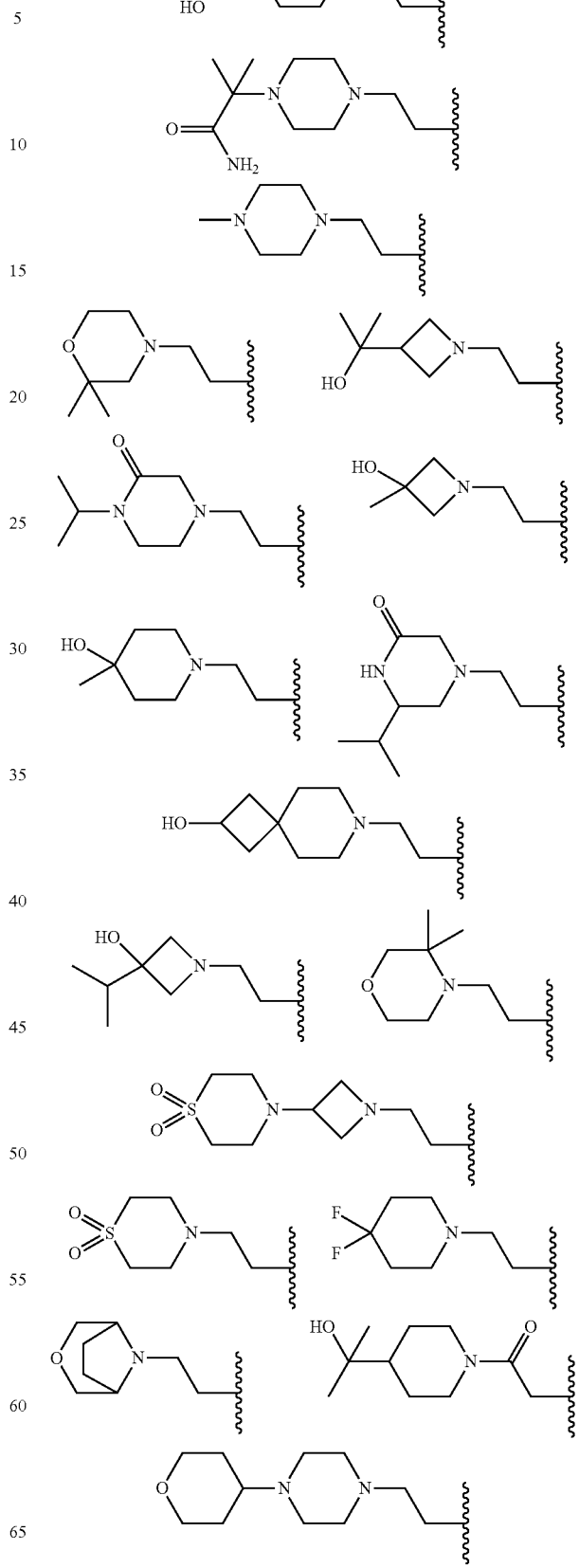

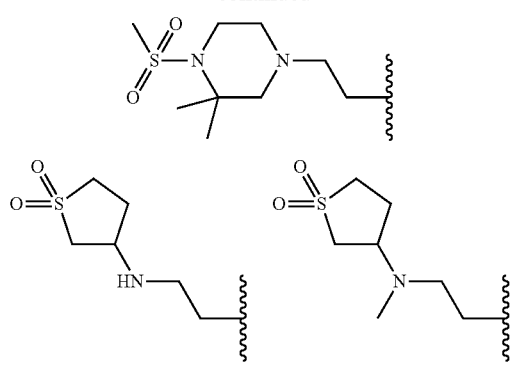
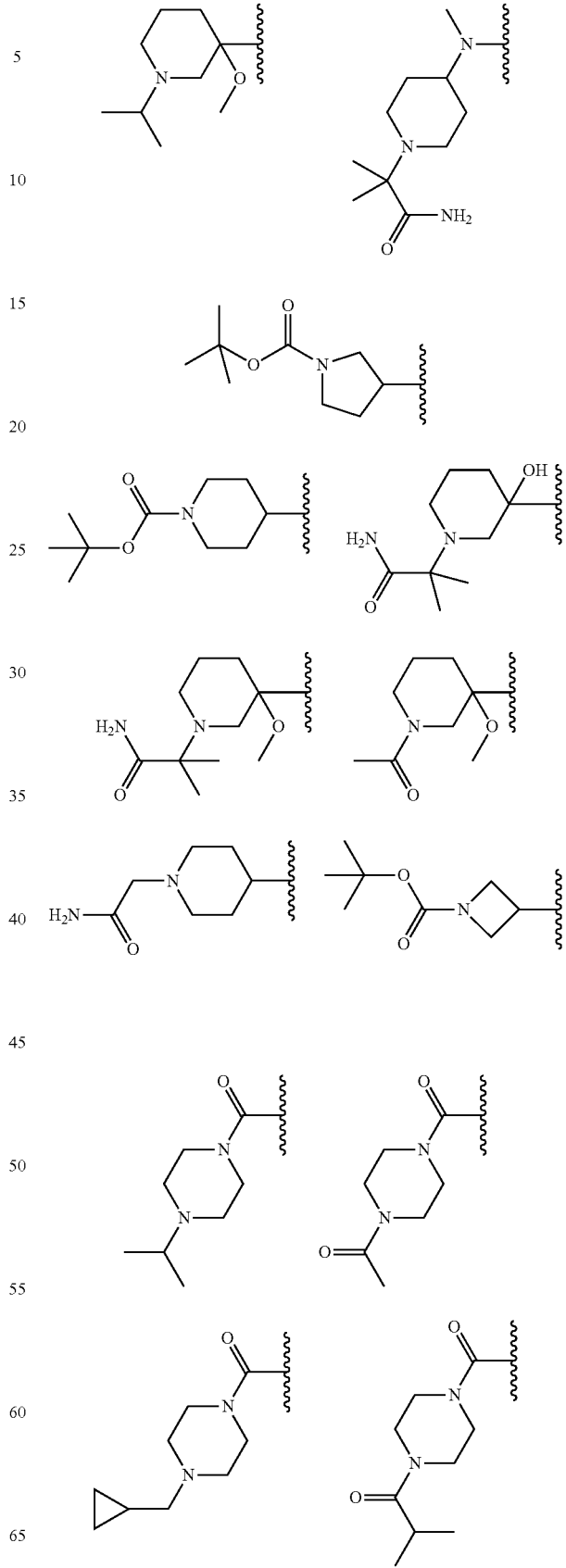

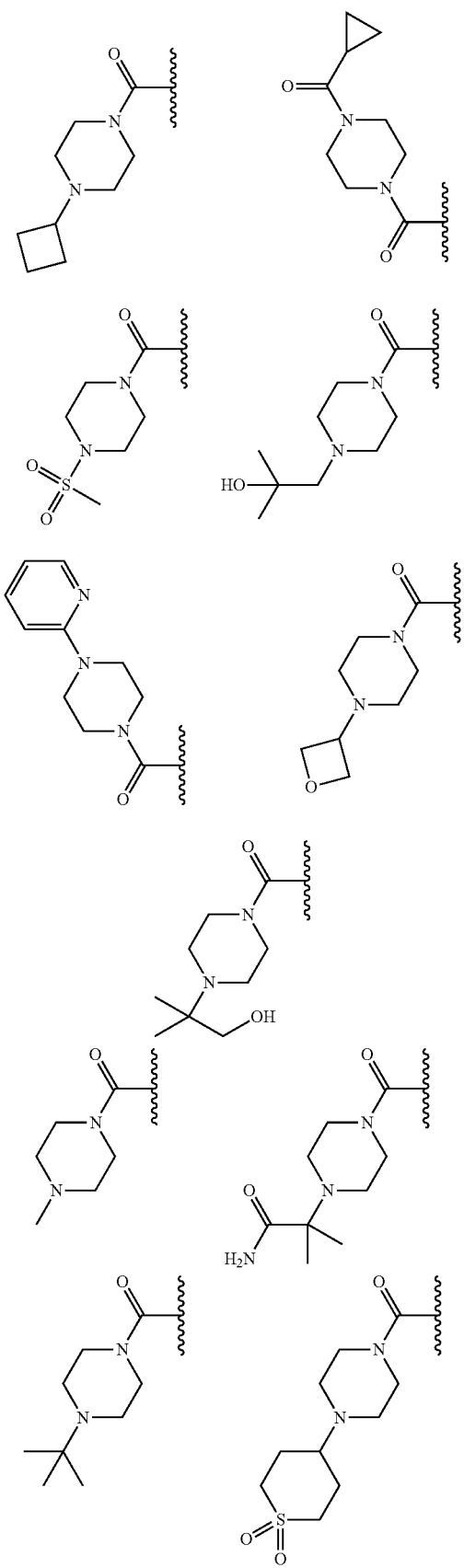
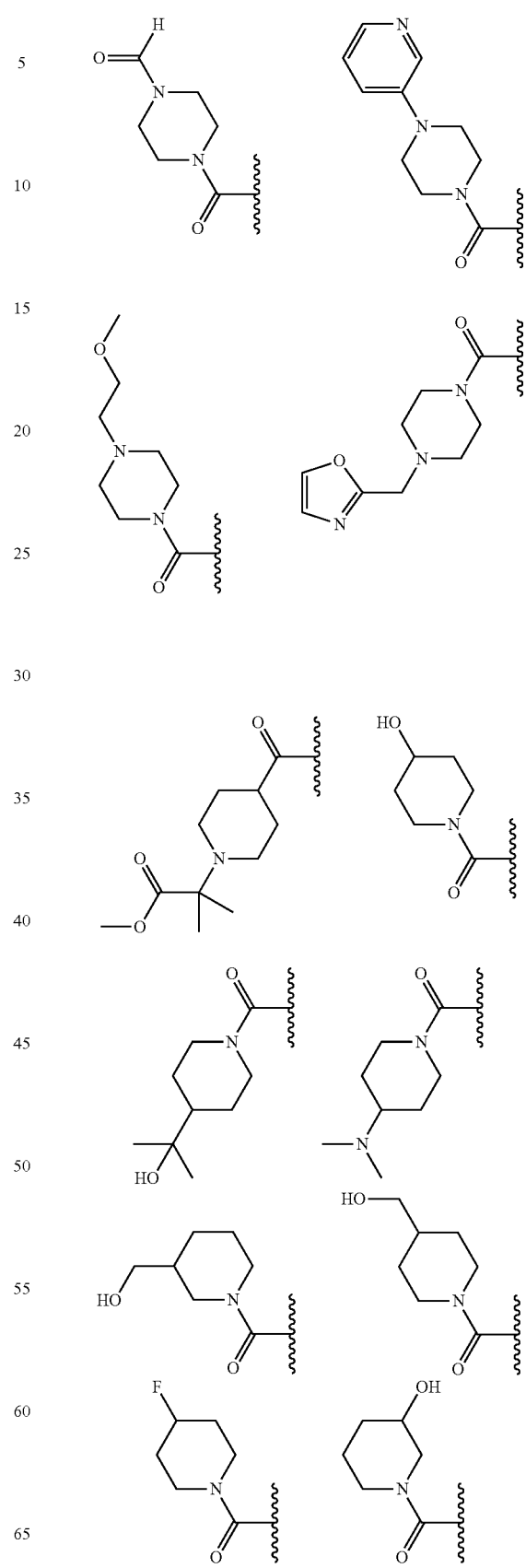

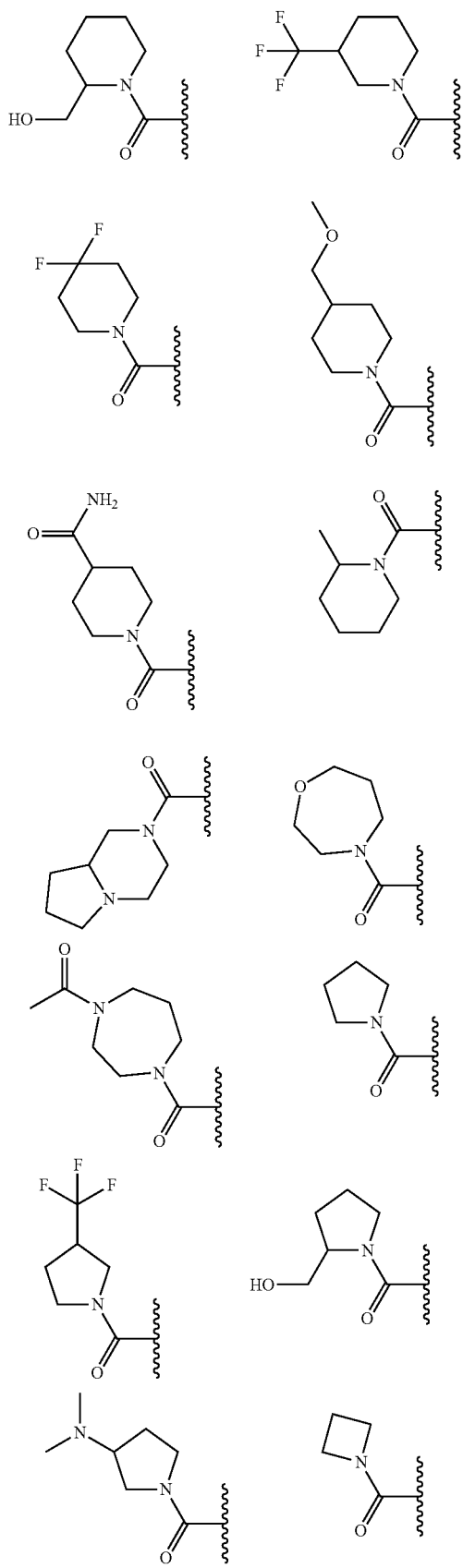
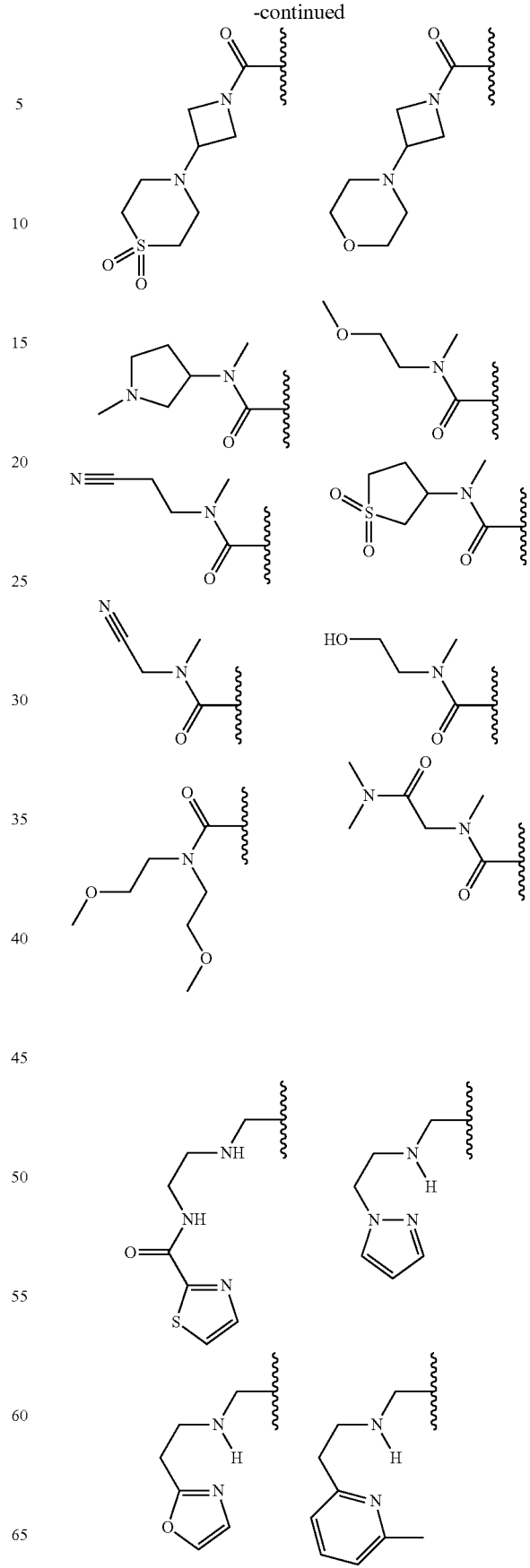

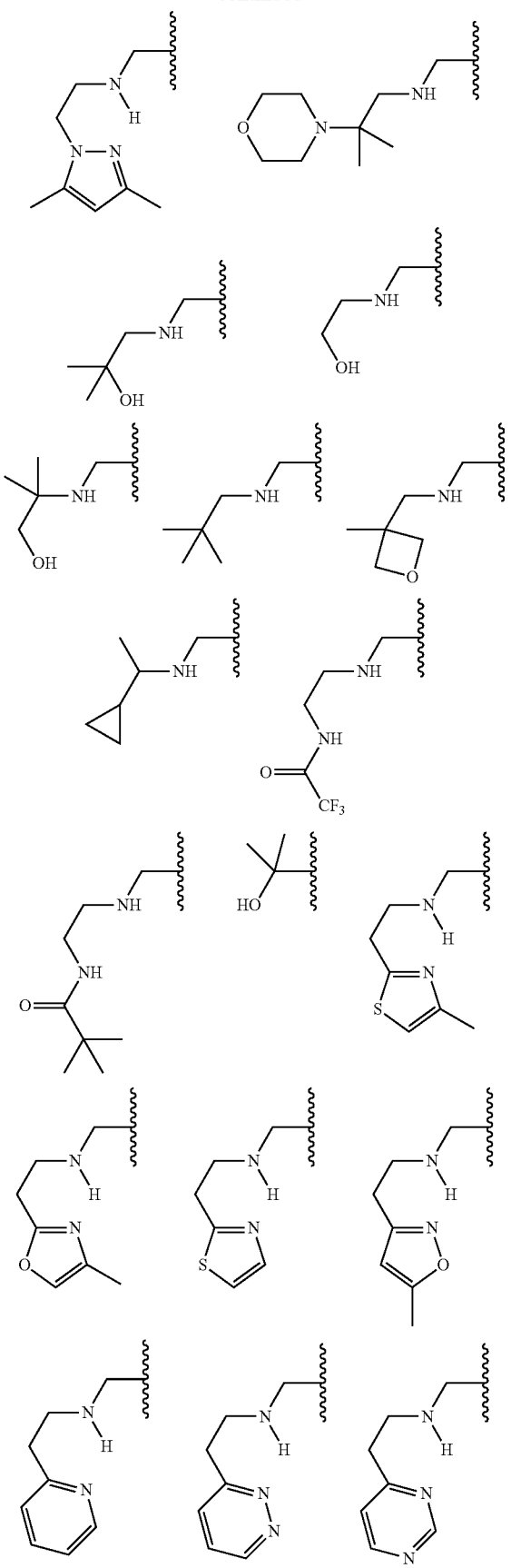

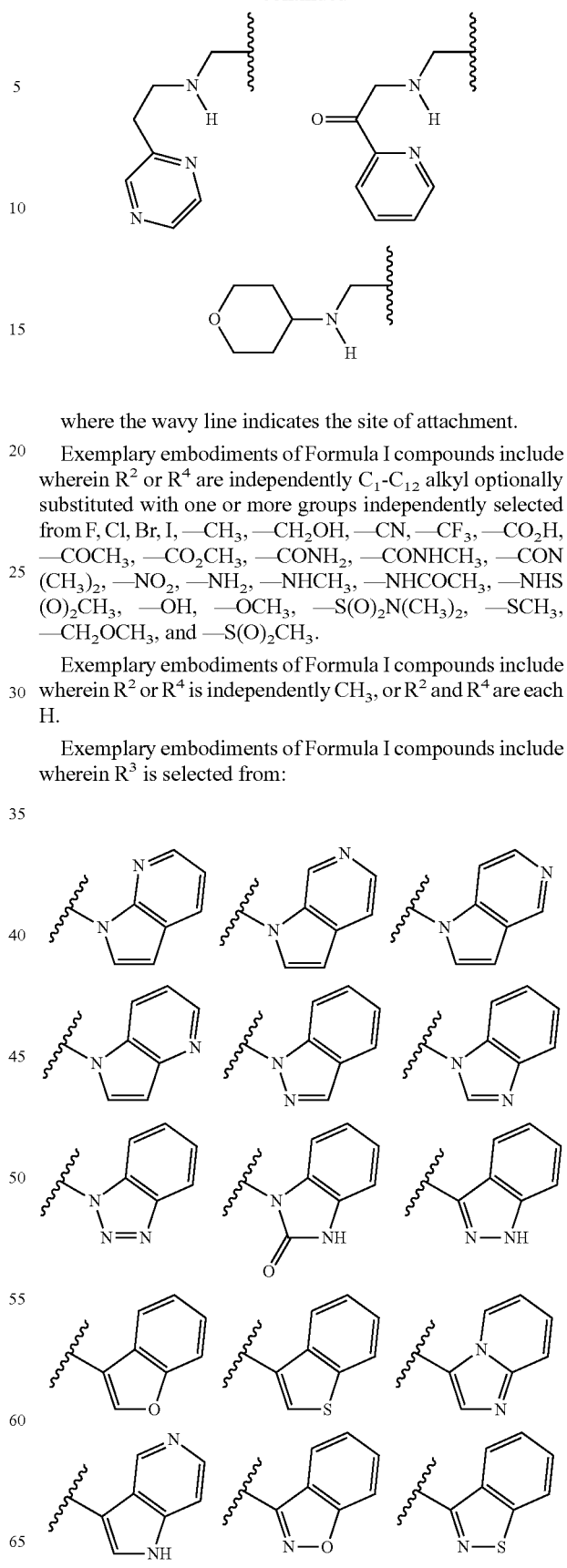

where the wavy line indicates the site of attachment.

Exemplary embodiments of Formula I compounds include wherein $R^2$ or $R^4$ are independently $C_1$-$C_{12}$ alkyl optionally substituted with one or more groups independently selected from F, Cl, Br, I, —$CH_3$, —$CH_2OH$, —CN, —$CF_3$, —$CO_2H$, —$COCH_3$, —$CO_2CH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$.

Exemplary embodiments of Formula I compounds include wherein $R^2$ or $R^4$ is independently $CH_3$, or $R^2$ and $R^4$ are each H.

Exemplary embodiments of Formula I compounds include wherein $R^3$ is selected from:

35
-continued

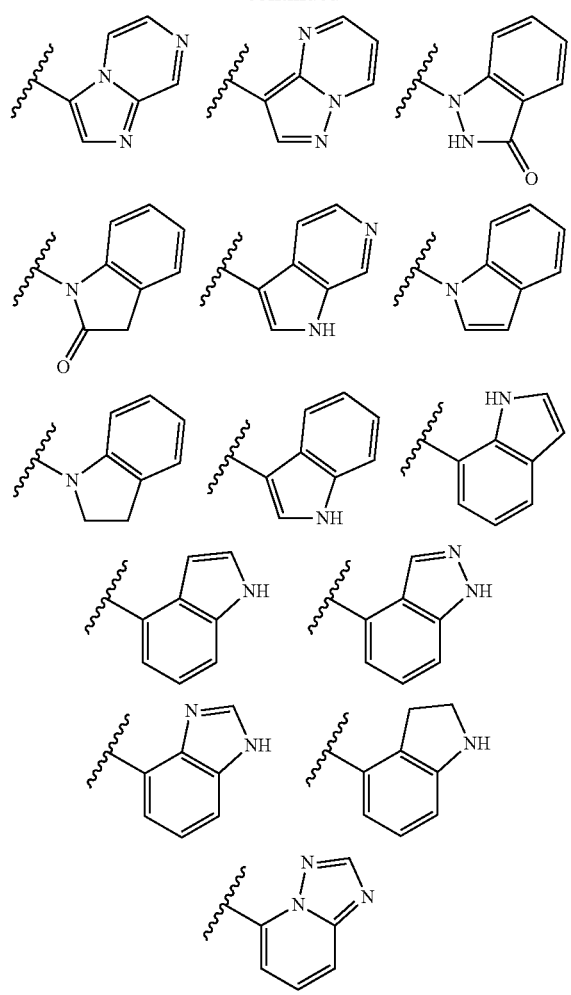

36
-continued

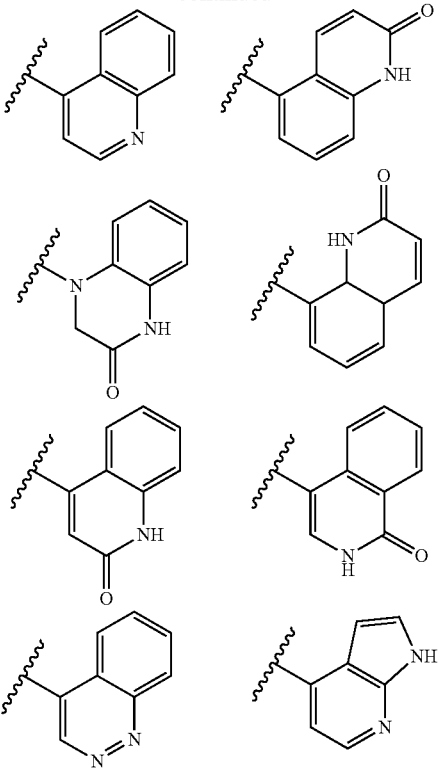

each of which are optionally substituted with one or more groups independently selected from F, Cl, Br, I, —CH₃, —CH₂CH₃, —CH₂CH₂CH₃, —CH(CH₃)₂, —C(CH₃)₃, —CH₂OCH₃, —CHF₂, —CN, —CF₃, —CH₂OH, —CH₂OCH₃, —CH₂CH₂OH, —CH₂C(CH₃)₂OH, —CH(CH₃)OH, —CH(CH₂CH₃)OH, —CH₂CH(OH)CH₃, —CH₂CH(OCH₃)CH₃, —C(CH₃)₂OH, —C(CH₃)₂OCH₃, —CH(CH₃)F, —C(CH₃)F₂, —CH(CH₂CH₃)F, —C(CH₂CH₃)₂F, —CO₂H, —CONH₂, —CON(CH₂CH₃)₂, —COCH₃, —CON(CH₃)₂, —NO₂, —NH₂, —NHCH₃, —N(CH₃)₂, —NHCH₂CH₃, —NHCH(CH₃)₂, —NHCH₂CH₂OH, —NHCH₂CH₂OCH₃, —NHCOCH₃, —NHCOCH₂CH₃, —NHCOCH₂OH, —NHS(O)₂CH₃, —N(CH₃)S(O)₂CH₃, =O, —OH, —OCH₃, —OCH₂CH₃, —OCH(CH₃)₂, —SH, —NHC(=O)NHCH₃, —NHC(=O)NHCH₂CH₃, —S(O)CH₃, —S(O)CH₂CH₃, —S(O)₂CH₃, —S(O)₂NH₂, —S(O)₂NHCH₃, —S(O)₂N(CH₃)₂, —CH₂S(O)₂CH₃, and a group selected from

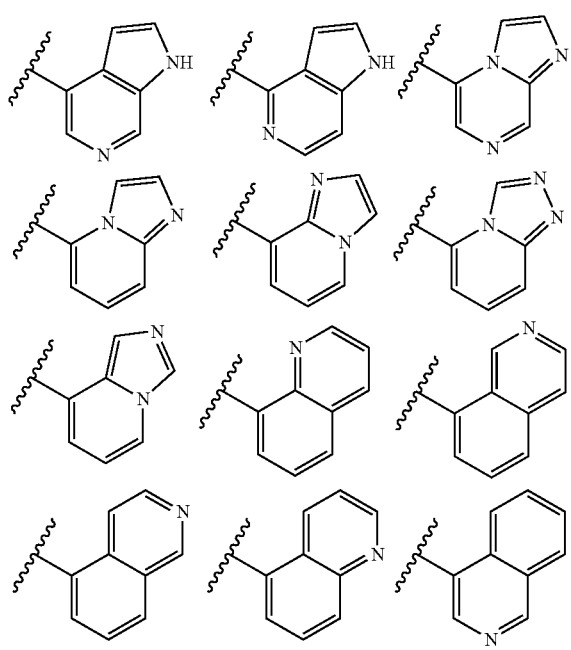

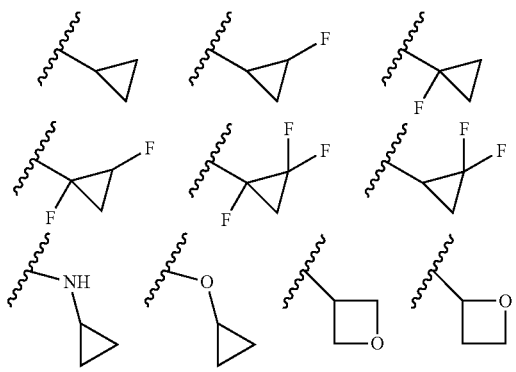

-continued

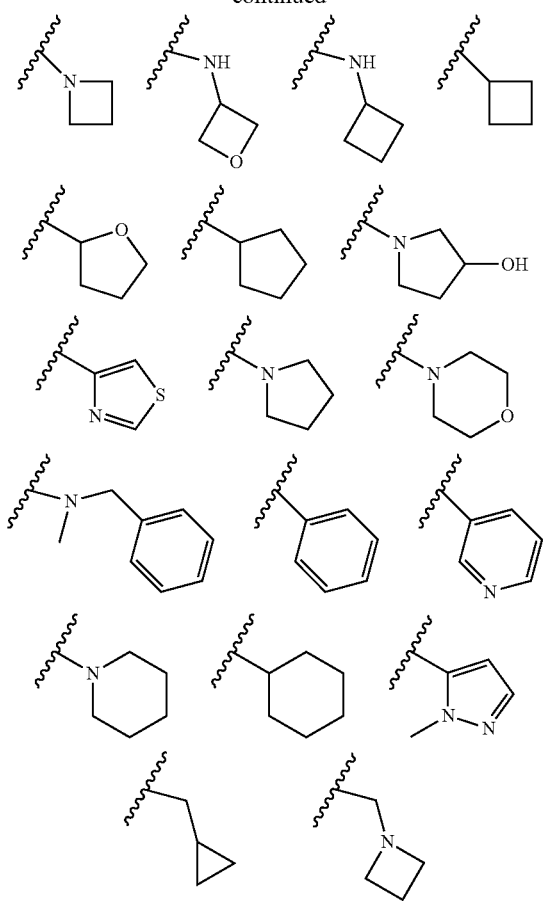

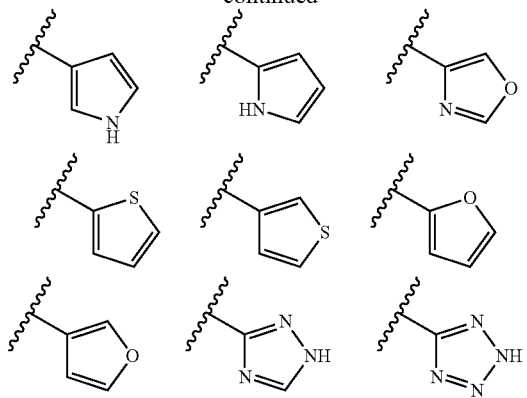

where the wavy line indicates the site of attachment.
Exemplary embodiments of Formula I compounds include wherein R³ is a monocyclic heteroaryl selected from:

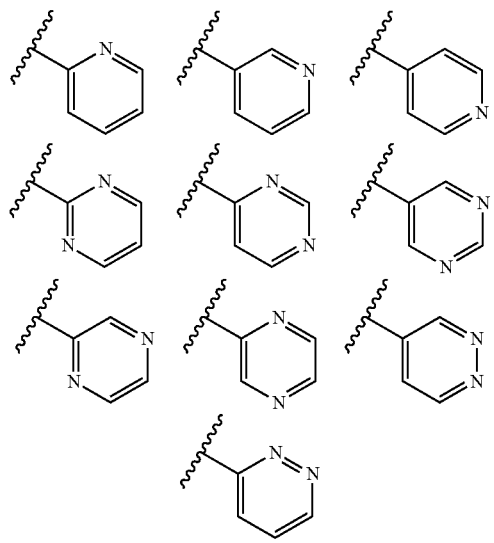

where the wavy line indicates the site of attachment.
Exemplary embodiments of Formula I compounds include wherein R³ is a monocyclic heteroaryl selected from pyridyl, isoxazolyl, imidazolyl, pyrazolyl, pyrrolyl, thiazolyl, pyridazinyl, pyrimidinyl, pyrazinyl, oxazolyl, oxadiazolyl, furanyl, thienyl, triazolyl, and tetrazolyl.

Exemplary embodiments of Formula I compounds include wherein R³ is a monocyclic heteroaryl selected from:

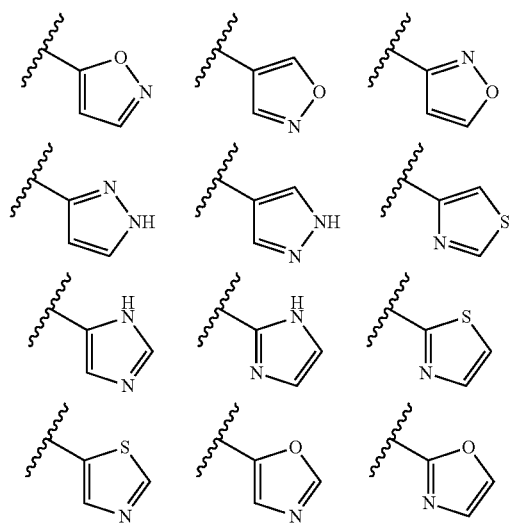

where the wavy line indicates the site of attachment.
Exemplary embodiments of Formula I compounds include wherein R³ is a monocyclic heteroaryl selected from:

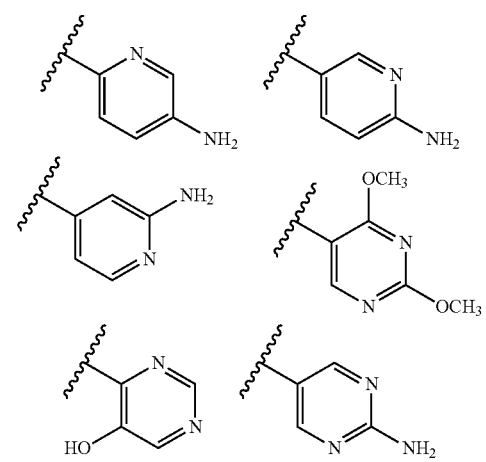

-continued
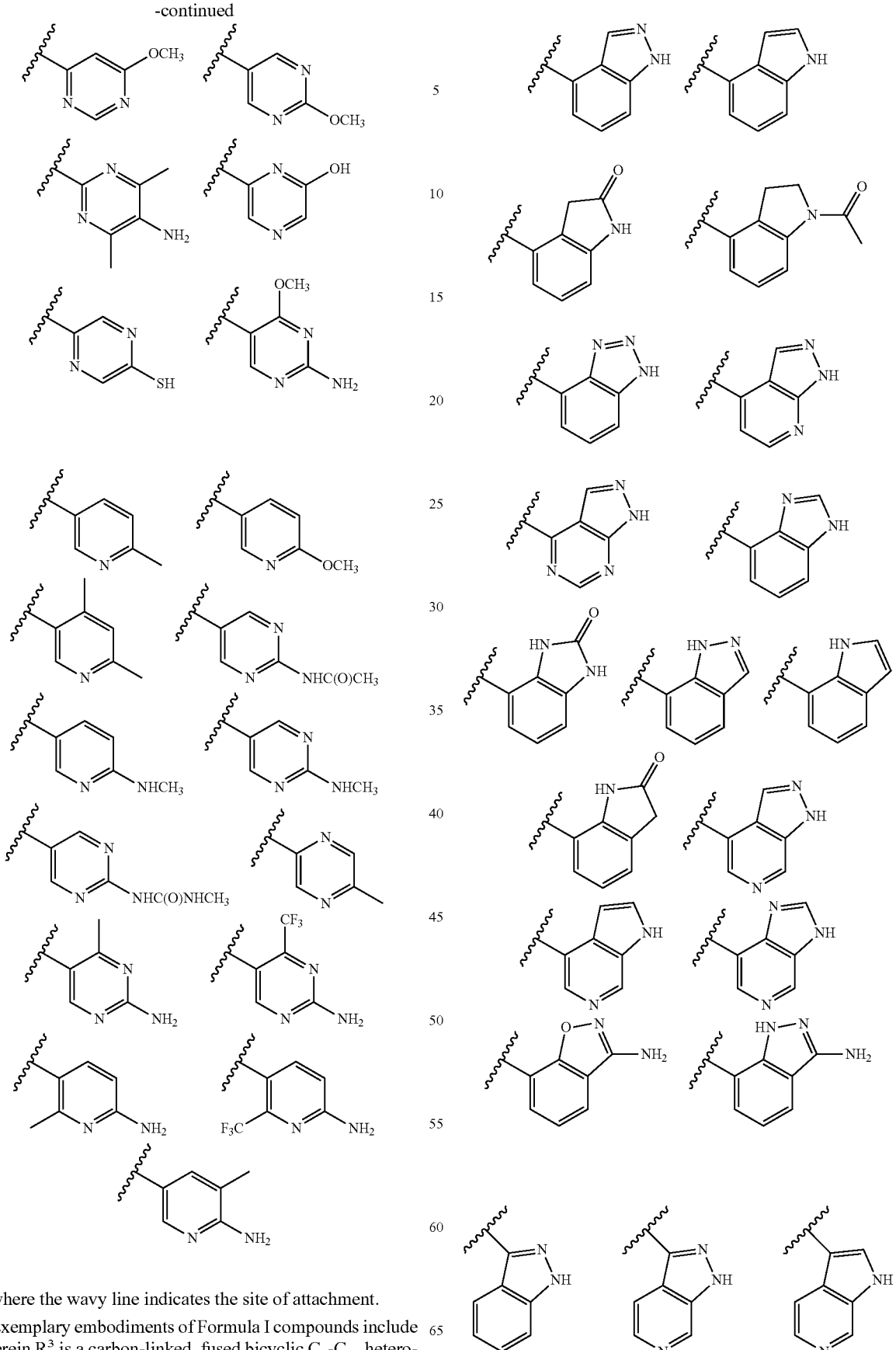
where the wavy line indicates the site of attachment.
Exemplary embodiments of Formula I compounds include wherein $R^3$ is a carbon-linked, fused bicyclic $C_4$-$C_{20}$ heterocyclyl or $C_1$-$C_{20}$ heteroaryl selected from -continued

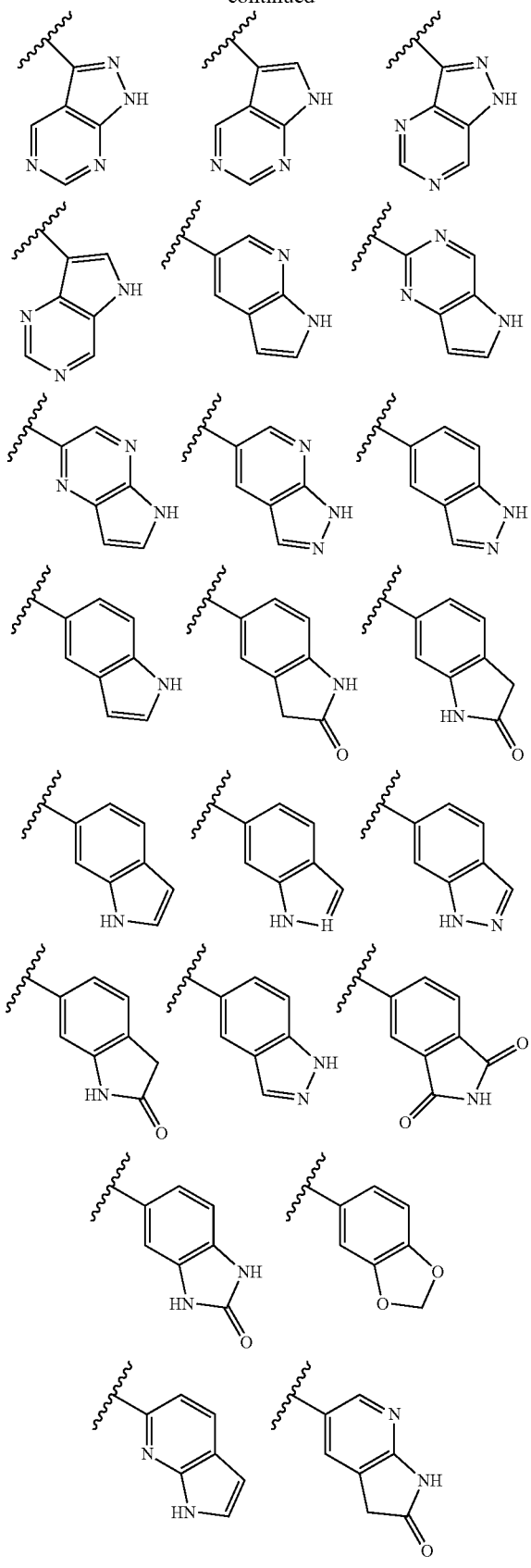

where the wavy line indicates the site of attachment.

Exemplary embodiments of Formula I compounds include wherein $R^3$ is selected from:

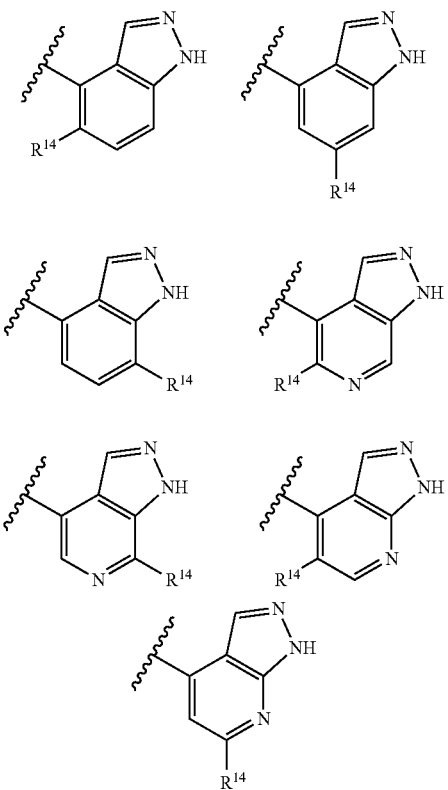

where the wavy line indicates the site of attachment and $R^{14}$ is selected from F, Cl, Br, I, —CH$_3$, —CN, —CF$_3$, —CH$_2$OH, —CO$_2$H, —CONH$_2$, —CON(CH$_3$)$_2$, —NO$_2$, —NH$_2$, —NHCH$_3$, —NHCOCH$_3$, —OH, —OCH$_3$, —SH, —NHC(=O)NHCH$_3$, —NHC(=O)NHCH$_2$CH$_3$, and —S(O)$_2$CH$_3$.

Exemplary embodiments of Formula I compounds include wherein $R^3$ is a carbon-linked, fused bicyclic $C_4$-$C_{20}$ heterocyclyl or $C_1$-$C_{20}$ heteroaryl selected from:

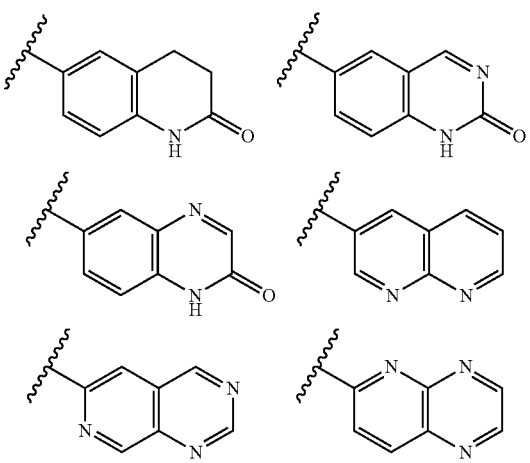

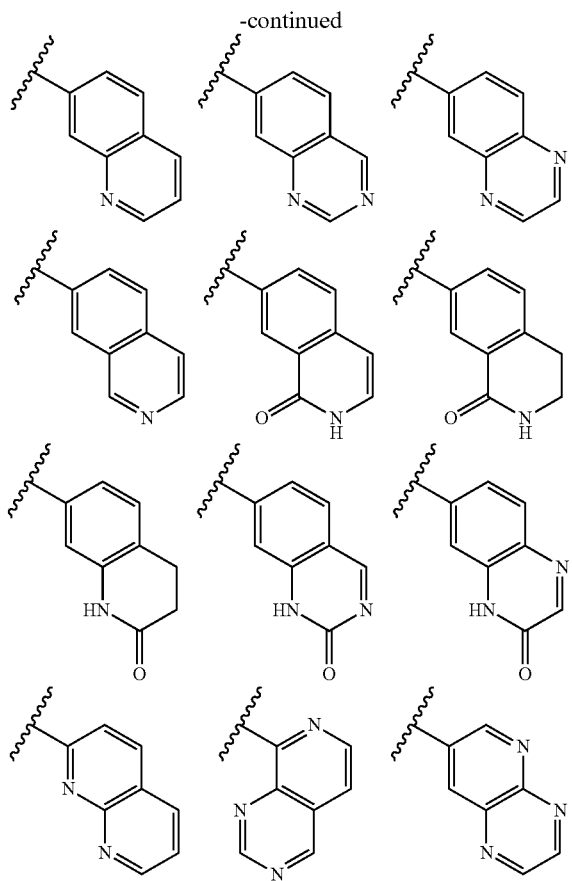

where the wavy line indicates the site of attachment.

Exemplary embodiments of Formula I compounds include wherein $R^3$ is 1H-indazol-4-yl and n is 0.

Alternatively, Formula I compounds include compounds having the formula:

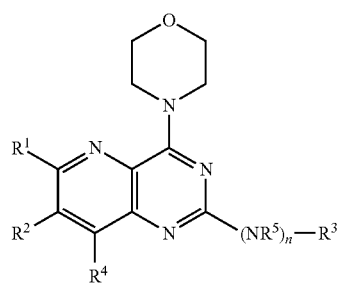

and stereoisomers, geometric isomers, tautomers, or pharmaceutically acceptable salts thereof,
wherein $R^1$ is selected from $C_1$-$C_{12}$ alkyl, $C_2$-$C_8$ alkenyl, $C_2$-$C_8$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_2$-$C_{20}$ heterocyclyl)-($C_2$-$C_{20}$ heterocyclyl), —($C_1$-$C_{12}$ alkylene)-($C_2$-$C_{20}$ heterocyclyl)-($C_3$-$C_{12}$ carbocyclyl), —($C_1$-$C_{12}$ alkylene)-($C_2$-$C_{20}$ heterocyclyl)-C(=O)—($C_2$-$C_{20}$ heterocyclyl), —($C_1$-$C_{12}$ alkylene)-($C_1$-$C_{20}$ heteroaryl), —($C_1$-$C_{12}$ alkylene)-($C_2$-$C_{20}$ heterocyclyl)-($C_1$-$C_{12}$ alkyl), —($C_1$-$C_{12}$ alkylene)-($C_6$-$C_{20}$ aryl)-($C_1$-$C_{12}$ alkyl), —($C_1$-$C_{12}$ alkylene)-($C_1$-$C_{20}$ heteroaryl)-($C_1$-$C_{12}$ alkyl), —($C_1$-$C_{12}$ alkylene)-C(=O)—($C_2$-$C_{20}$ heterocyclyl), —($C_1$-$C_{12}$ alkylene)-NHR$^2$, —($C_1$-$C_{12}$ alkylene)-NR$^2$—($C_1$-$C_{12}$ alkyl), —($C_1$-$C_{12}$ alkylene)-N($C_1$-$C_{12}$ alkyl)($C_2$-$C_{20}$ heterocyclyl), —($C_1$-$C_{12}$ alkylene)-NR$^2$—($C_1$-$C_{12}$ alkylene)-($C_1$-$C_{20}$ heteroaryl), —($C_1$-$C_{12}$ alkylene)-NR$^2$—($C_1$-$C_{12}$ alkylene)-($C_2$-$C_{20}$ heterocyclyl), —($C_1$-$C_{12}$ alkylene)-NR$^2$—($C_1$-$C_{12}$ alkylene)-NHC(=O)—($C_1$-$C_{20}$ heteroaryl), —($C_1$-$C_{12}$ alkylene)-($C_2$-$C_{20}$ heterocyclyl)-N($C_1$-$C_{12}$ alkyl)R$^2$, —($C_1$-$C_{12}$ alkylene)-($C_2$-$C_{20}$ heterocyclyl)-($C_1$-$C_{12}$ alkyl)-N($C_1$-$C_{12}$ alkyl)R$^2$, —($C_1$-$C_{12}$ alkylene)-NR$^2$—($C_2$-$C_{20}$ heterocyclyl), —($C_2$-$C_{12}$ alkenylene)-($C_2$-$C_{20}$ heterocyclyl), —NR$^2$—($C_2$-$C_{20}$ heterocyclyl), —C(=O)—($C_2$-$C_{20}$ heterocyclyl), and —C(=O)—($C_1$-$C_{12}$ alkyl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino;

$R^2$ and $R^4$ are independently selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —COC(CH$_3$)$_3$, —COCF$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

$R^3$ is selected from $C_6$-$C_{20}$ aryl, $C_2$-$C_{20}$ heterocyclyl and $C_1$-$C_{20}$ heteroaryl, each of which are optionally substituted with one or more groups independently selected from F, Cl, Br, I, —CH$_3$, —CN, —CF$_3$, —CH$_2$OH, —CO$_2$H, —CONH$_2$, —CON(CH$_3$)$_2$, —NO$_2$, —NH$_2$, —NHCH$_3$, —NHCOCH$_3$, —OH, —OCH$_3$, —SH, —NHC(=O)NHCH$_3$, —NHC(=O)NHCH$_2$CH$_3$, and —S(O)$_2$CH$_3$;

$R^5$ is selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

and n is 0 or 1.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Accordingly, a "selective PI3K delta inhibitor" can be understood to refer to a compound that exhibits a 50% inhibitory concentration ($IC_{50}$) with respect to PI3K delta that is at least at least 10-fold lower than the IC50 value with respect to any or all of the other Class I PI3K family members.

Determination of the activity of PI3 kinase activity of Formula I compounds is possible by a number of direct and indirect detection methods. Certain exemplary compounds described herein were assayed for their ability to inhibit PI3K alpha, beta, gamma, and delta isoforms (Example 901). The range of IC50 values for inhibition of PI3K delta was less than 1 nM (nanomolar) to about 10 μM (micromolar). Certain exemplary compounds of the invention had PI3K delta inhibitory $IC_{50}$ values less than 10 nM. The compounds are selective for the p110δ (delta) isoform, which is a class Ia PI3 kinase, over other class Ia PI3 kinases, and are thus selective for the p110δ isoform over both the p110α (alpha) isoform and the p110β (beta) isoform. In particular, they are selective for p110δ (delta) over p110α (alpha). The compounds are also selective for the p110δ isoform over p110γ (gamma), which is a class Ib kinase. The selectivity exhibited by certain Formula I compounds of the invention for p110δ (delta) over the p110α (alpha) isoform of PI3 kinase is at least 10 fold, as exemplified by the ratios of biochemical $IC_{50}$ values (Example 901).

Certain Formula I compounds may have antiproliferative activity to treat hyperproliferative disorders such as cancer. The Formula I compounds may inhibit tumor growth in mammals and may be useful for treating human cancer patients. Formula I compounds may be tested for in vitro cell proliferation activity and in vivo tumor growth inhibition according to the methods in WO 2006/046031; US 2008/0039459; US 2008/0076768; US 2008/0076758; WO 2008/070740; WO 2008/073785, which are incorporated by reference herein.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology, Vol. 1.* Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through the PI3K pathway in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study using an autoimmune mechanism to mimic human arthritis; rat and mouse models (Example 902). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 903) determines the ability of compounds to inhibit the production of CD69 by B lymphocytes in human whole blood activated by crosslinking surface IgM with goat F(ab')2 anti-human IgM.

The T-cell Dependent Antibody Response (TDAR) is a predictive assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern Methods in Immunotoxicology, Volume* 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

Exemplary Formula I compounds No. 101-201 in Tables 1 and 2 were made, characterized, and tested for inhibition of PI3K delta and selectivity according to the methods of this invention, and have the following structures and corresponding names (ChemDraw Ultra, Version 9.0.1, CambridgeSoft Corp., Cambridge Mass.).

TABLE 1

| No. | Structure | Name |
|---|---|---|
| 101 | 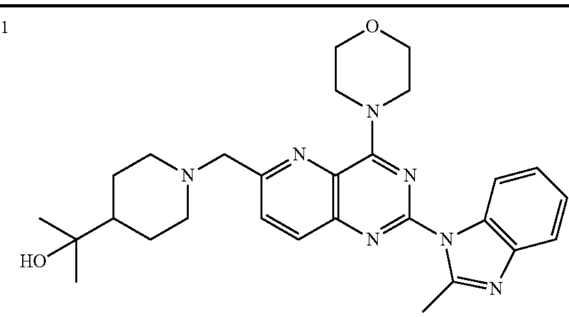 | 2-(1-((2-(2-methyl-1H-benzo[d]imidazol-1-yl)-4-morpholinopyrido[3,2-d]pyrimidin-6-yl)methyl)piperidin-4-yl)propan-2-ol |
| 102 | 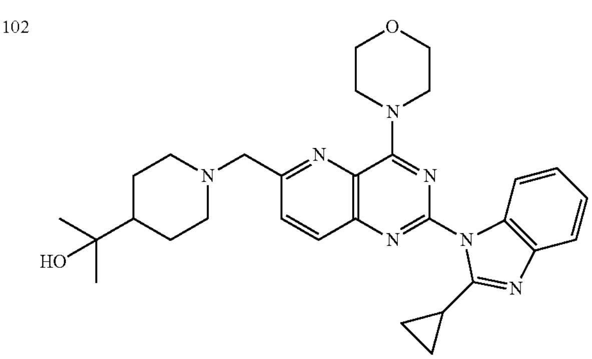 | 2-(1-((2-(2-cyclopropyl-1H-benzo[d]imidazol-1-yl)-4-morpholinopyrido[3,2-d]pyrimidin-6-yl)methyl)piperidin-4-yl)propan-2-ol |

TABLE 1-continued

| No. | Structure | Name |
|---|---|---|
| 103 | 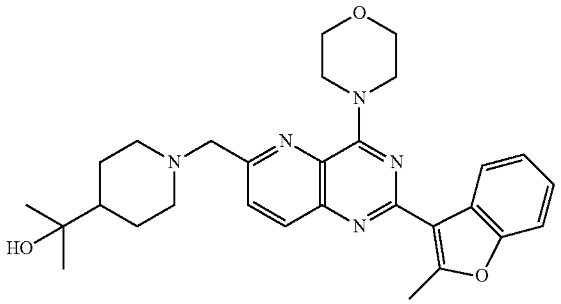 [SMILES: Cc1oc2ccccc2c1-c1nc(N2CCOCC2)c2nc(CN3CCC(C(C)(C)O)CC3)ccc2n1] | 2-(1-((2-(2-methylbenzofuran-3-yl)-4-morpholinopyrido[3,2-d]pyrimidin-6-yl)methyl)piperidin-4-yl)propan-2-ol |
| 104 | 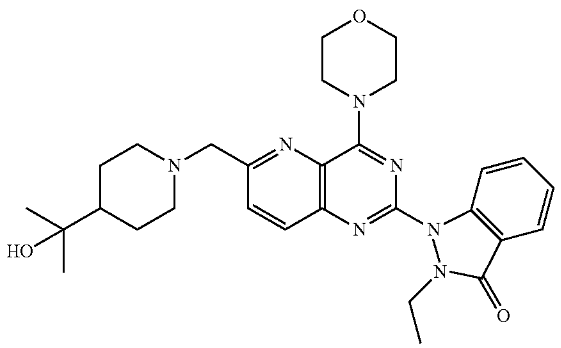 [SMILES: CCn1c(=O)c2ccccc2n1-c1nc(N2CCOCC2)c2nc(CN3CCC(C(C)(C)O)CC3)ccc2n1] | 2-ethyl-1-(6-((4-(2-hydroxypropan-2-yl)piperidin-1-yl)methyl)-4-morpholinopyrido[3,2-d]pyrimidin-2-yl)-1H-indazol-3(2H)-one |
| 105 | 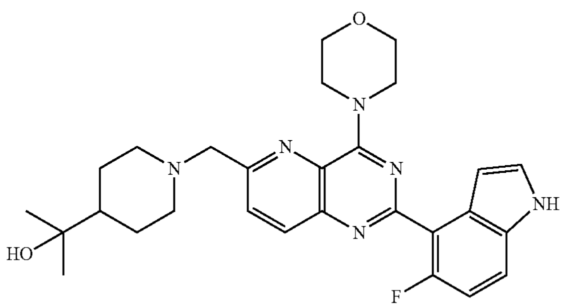 [SMILES: CC(C)(O)C1CCN(Cc2ccc3nc(-c4c(F)ccc5[nH]ccc45)nc(N4CCOCC4)c3n2)CC1] | 2-(1-((2-(5-fluoro-1H-indol-4-yl)-4-morpholinopyrido[3,2-d]pyrimidin-6-yl)methyl)piperidin-4-yl)propan-2-ol |
| 106 | 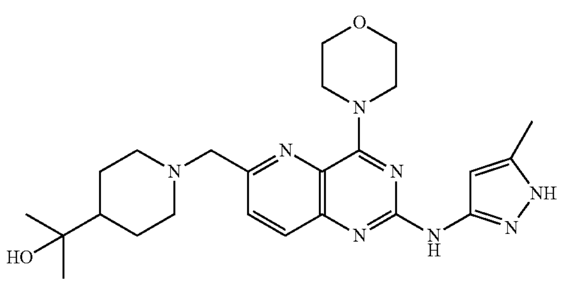 [SMILES: Cc1cc(Nc2nc(N3CCOCC3)c3nc(CN4CCC(C(C)(C)O)CC4)ccc3n2)n[nH]1] | 2-(1-((2-(5-methyl-1H-pyrazol-3-ylamino)-4-morpholinopyrido[3,2-d]pyrimidin-6-yl)methyl)piperidin-4-yl)propan-2-ol |
| 107 | 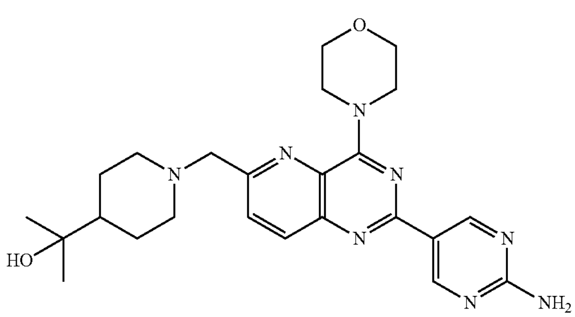 [SMILES: CC(C)(O)C1CCN(Cc2ccc3nc(-c4cnc(N)nc4)nc(N4CCOCC4)c3n2)CC1] | 2-(1-((2-(2-aminopyrimidin-5-yl)-4-morpholinopyrido[3,2-d]pyrimidin-6-yl)methyl)piperidin-4-yl)propan-2-ol |

TABLE 1-continued

| No. | Structure | Name |
|---|---|---|
| 108 | 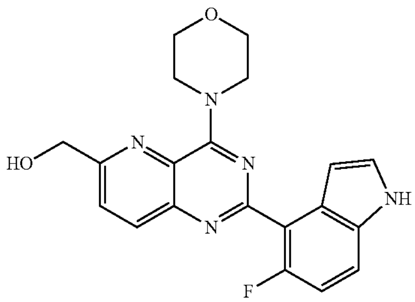 [SMILES: OCc1ccc2nc(-c3c(F)ccc4[nH]ccc34)nc(N3CCOCC3)c2n1] | (2-(5-fluoro-1H-indol-4-yl)-4-morpholinopyrido[3,2-d]pyrimidin-6-yl)methanol |
| 109 | 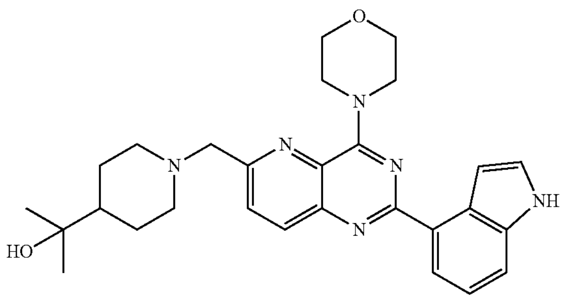 [SMILES: CC(C)(O)C1CCN(Cc2ccc3nc(-c4cccc5[nH]ccc45)nc(N4CCOCC4)c3n2)CC1] | 2-(1-((2-(1H-indol-4-yl)-4-morpholinopyrido[3,2-d]pyrimidin-6-yl)methyl)piperidin-4-yl)propan-2-ol |
| 110 | 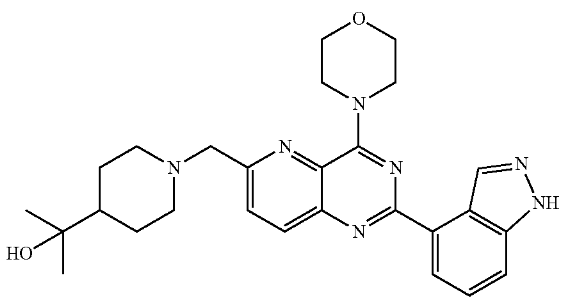 [SMILES: CC(C)(O)C1CCN(Cc2ccc3nc(-c4cccc5[nH]ncc45)nc(N4CCOCC4)c3n2)CC1] | 2-(1-((2-(1H-indazol-4-yl)-4-morpholinopyrido[3,2-d]pyrimidin-6-yl)methyl)piperidin-4-yl)propan-2-ol |
| 111 | 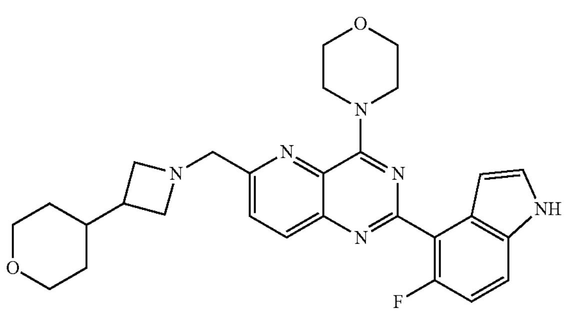 [SMILES: Fc1ccc2[nH]ccc2c1-c1nc(N2CCOCC2)c2nc(CN3CC(C4CCOCC4)C3)ccc2n1] | 4-(2-(5-fluoro-1H-indol-4-yl)-6-((3-(tetrahydro-2H-pyran-4-yl)azetidin-1-yl)methyl)pyrido[3,2-d]pyrimidin-4-yl)morpholine |
| 112 | 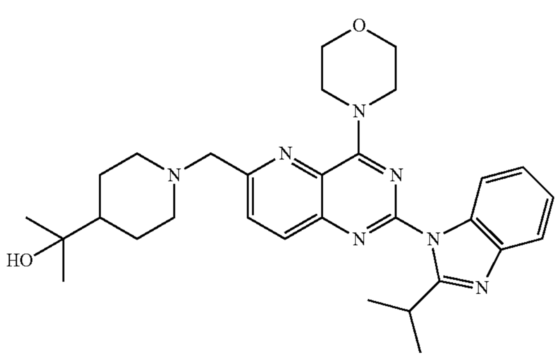 [SMILES: CC(C)c1nc2ccccc2n1-c1nc(N2CCOCC2)c2nc(CN3CCC(C(C)(C)O)CC3)ccc2n1] | 2-(1-((2-(2-isopropyl-1H-benzo[d]imidazol-1-yl)-4-morpholinopyrido[3,2-d]pyrimidin-6-yl)methyl)piperidin-4-yl)propan-2-ol |

TABLE 1-continued

| No. | Structure | Name |
|---|---|---|
| 113 | 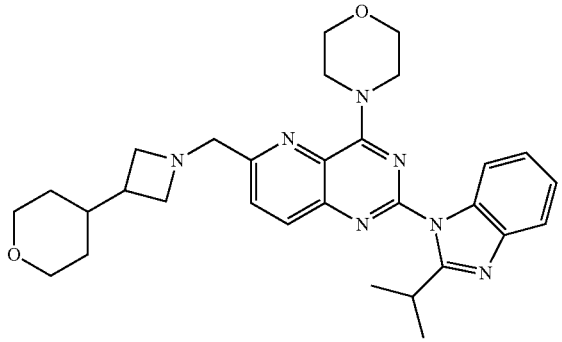 [SMILES: CC(C)c1nc2ccccc2n1-c1nc(N2CCOCC2)c2nc(CN3CC(C4CCOCC4)C3)ccc2n1] | 4-(2-(2-isopropyl-1H-benzo[d]imidazol-1-yl)-6-((3-(tetrahydro-2H-pyran-4-yl)azetidin-1-yl)methyl)pyrido[3,2-d]pyrimidin-4-yl)morpholine |
| 114 | 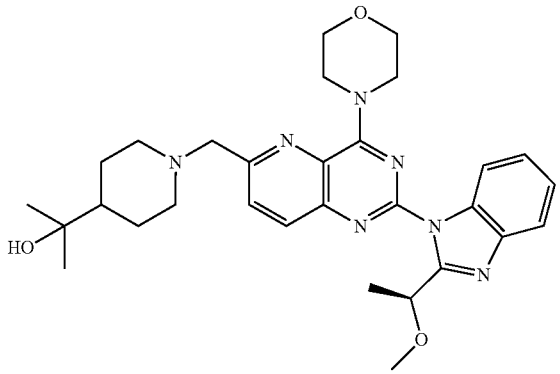 [SMILES: CO[C@@H](C)c1nc2ccccc2n1-c1nc(N2CCOCC2)c2nc(CN3CCC(C(C)(C)O)CC3)ccc2n1] | (S)-2-(1-((2-(2-(1-methoxyethyl)-1H-benzo[d]imidazol-1-yl)-4-morpholinopyrido[3,2-d]pyrimidin-6-yl)methyl)piperidin-4-yl)propan-2-ol |
| 115 | 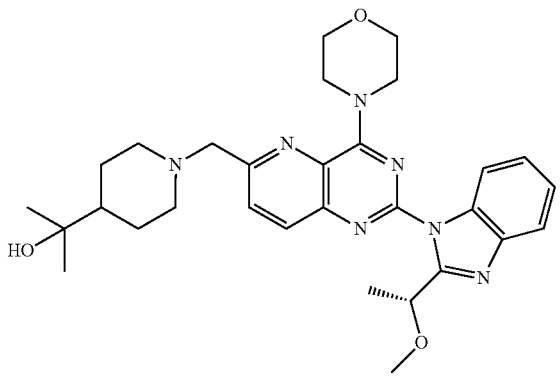 [SMILES: CO[C@H](C)c1nc2ccccc2n1-c1nc(N2CCOCC2)c2nc(CN3CCC(C(C)(C)O)CC3)ccc2n1] | (R)-2-(1-((2-(2-(1-methoxyethyl)-1H-benzo[d]imidazol-1-yl)-4-morpholinopyrido[3,2-d]pyrimidin-6-yl)methyl)piperidin-4-yl)propan-2-ol |
| 116 | 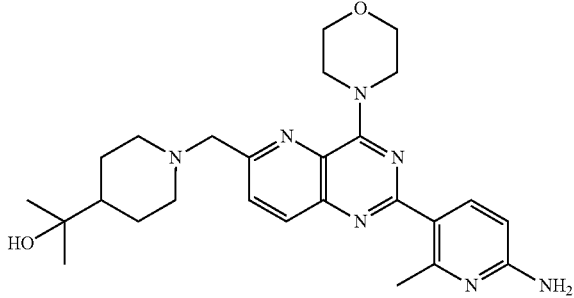 [SMILES: Cc1nc(N)ccc1-c1nc(N2CCOCC2)c2nc(CN3CCC(C(C)(C)O)CC3)ccc2n1] | 2-(1-((2-(6-amino-2-methylpyridin-3-yl)-4-morpholinopyrido[3,2-d]pyrimidin-6-yl)methyl)piperidin-4-yl)propan-2-ol |

TABLE 1-continued

| No. | Structure | Name |
|---|---|---|
| 117 | 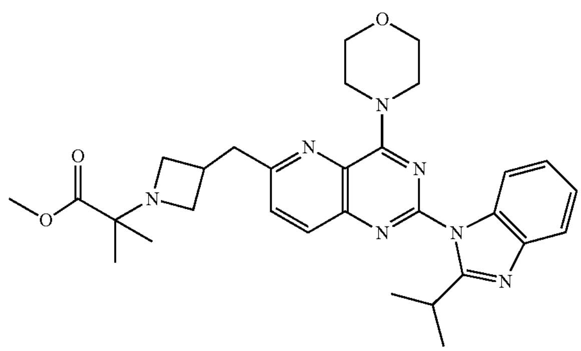 [SMILES: COC(=O)C(C)(C)N1CC(Cc2ccc3nc(-n4c(C(C)C)nc5ccccc54)nc(N4CCOCC4)c3n2)C1] | methyl 2-(3-((2-(2-isopropyl-1H-benzo[d]imidazol-1-yl)-4-morpholinopyrido[3,2-d]pyrimidin-6-yl)methyl)azetidin-1-yl)-2-methylpropanoate |
| 118 | 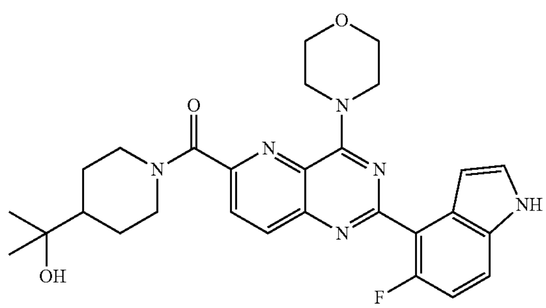 [SMILES: CC(C)(O)C1CCN(C(=O)c2ccc3nc(-c4c(F)ccc5[nH]ccc45)nc(N4CCOCC4)c3n2)CC1] | (2-(5-fluoro-1H-indol-4-yl)-4-morpholinopyrido[3,2-d]pyrimidin-6-yl)(4-(2-hydroxypropan-2-yl)piperidin-1-yl)methanone |
| 119 | 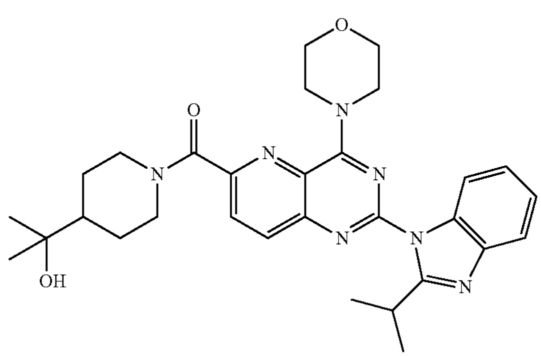 [SMILES: CC(C)c1nc2ccccc2n1-c1nc(N2CCOCC2)c2nc(C(=O)N3CCC(C(C)(C)O)CC3)ccc2n1] | (4-(2-hydroxypropan-2-yl)piperidin-1-yl)(2-(2-isopropyl-1H-benzo[d]imidazol-1-yl)-4-morpholinopyrido[3,2-d]pyrimidin-6-yl)methanone |
| 120 | 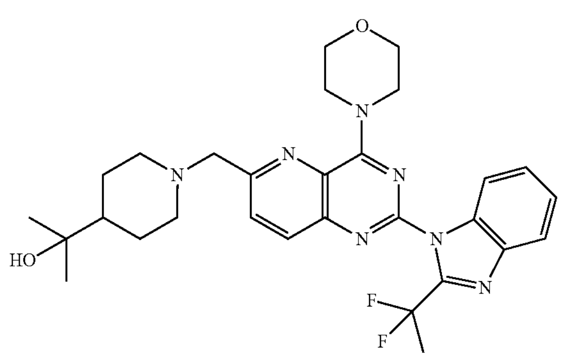 [SMILES: CC(F)(F)c1nc2ccccc2n1-c1nc(N2CCOCC2)c2nc(CN3CCC(C(C)(C)O)CC3)ccc2n1] | 2-(1-((2-(2-(1,1-difluoroethyl)-1H-benzo[d]imidazol-1-yl)-4-morpholinopyrido[3,2-d]pyrimidin-6-yl)methyl)piperidin-4-yl)propan-2-ol |

TABLE 1-continued

| No. | Structure | Name |
|---|---|---|
| 121 | 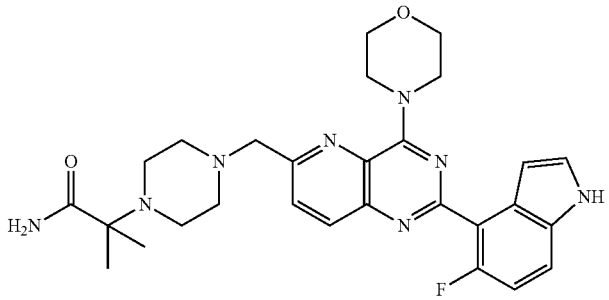 [SMILES: CC(C)(C(N)=O)N1CCN(Cc2ccc3nc(-c4c(F)ccc5[nH]ccc45)nc(N4CCOCC4)c3n2)CC1] | 2-(4-((2-(5-fluoro-1H-indol-4-yl)-4-morpholinopyrido[3,2-d]pyrimidin-6-yl)methyl)piperazin-1-yl)-2-methylpropanamide |
| 122 | 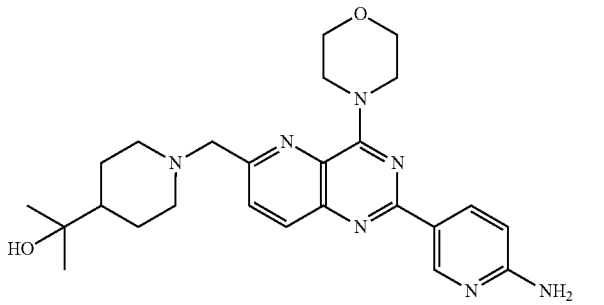 | 2-(1-((2-(6-aminopyridin-3-yl)-4-morpholinopyrido[3,2-d]pyrimidin-6-yl)methyl)piperidin-4-yl)propan-2-ol |
| 123 | 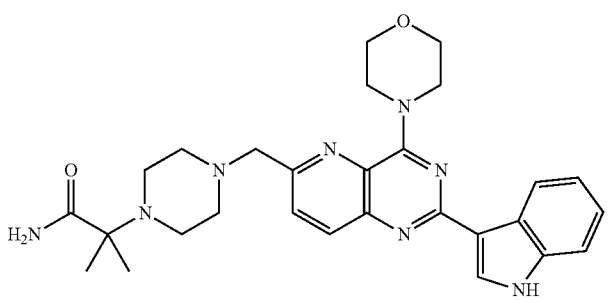 [SMILES: CC(C)(C(N)=O)N1CCN(Cc2ccc3nc(-c4c[nH]c5ccccc45)nc(N4CCOCC4)c3n2)CC1] | 2-(4-((2-(1H-indol-3-yl)-4-morpholinopyrido[3,2-d]pyrimidin-6-yl)methyl)piperazin-1-yl)-2-methylpropanamide |
| 124 | 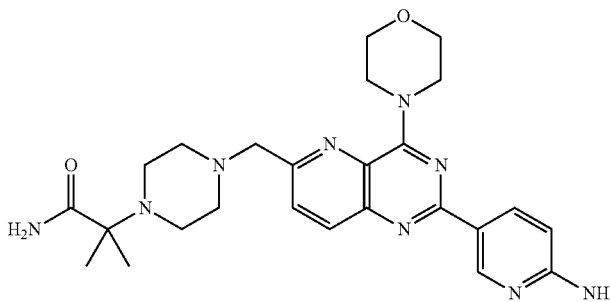 | 2-(4-((2-(6-aminopyridin-3-yl)-4-morpholinopyrido[3,2-d]pyrimidin-6-yl)methyl)piperazin-1-yl)-2-methylpropanamide |
| 125 | 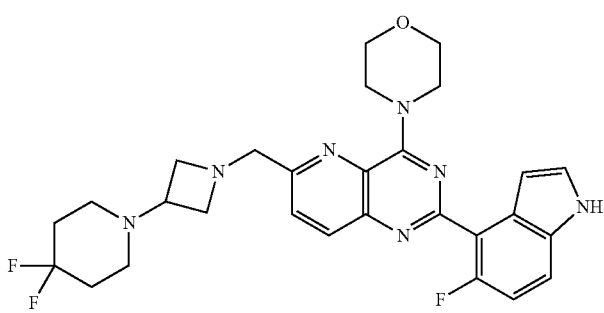 [SMILES: Fc1ccc2[nH]ccc2c1-c1nc(N2CCOCC2)c2nc(CN3CC(N4CCC(F)(F)CC4)C3)ccc2n1] | 4-(6-((3-(4,4-difluoropiperidin-1-yl)azetidin-1-yl)methyl)-2-(5-fluoro-1H-indol-4-yl)pyrido[3,2-d]pyrimidin-4-yl)morpholine |

TABLE 1-continued

| No. | Structure | Name |
|---|---|---|
| 126 | 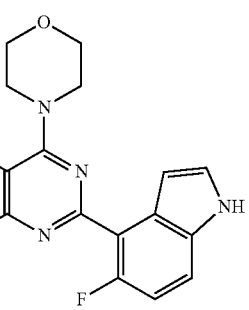 | 4-(1-((2-(5-fluoro-1H-indol-4-yl)-4-morpholinopyrido[3,2-d]pyrimidin-6-yl)methyl)azetidin-3-yl)morpholine |
| 127 | 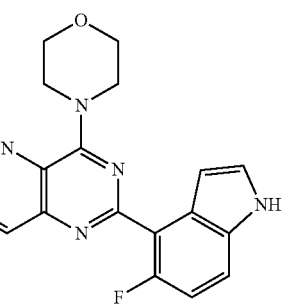 | 4-(1-((2-(5-fluoro-1H-indol-4-yl)-4-morpholinopyrido[3,2-d]pyrimidin-6-yl)methyl)azetidin-3-yl)piperazin-2-one |
| 128 | 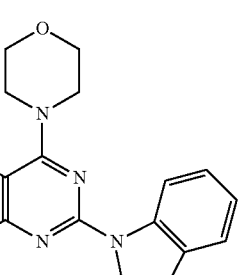 | 2-(1-((2-(1H-indol-1-yl)-4-morpholinopyrido[3,2-d]pyrimidin-6-yl)methyl)piperidin-4-yl)propan-2-ol |
| 129 | 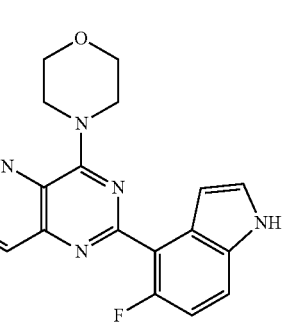 | 4-(2-(5-fluoro-1H-indol-4-yl)-6-((3-(1,1-dioxo)thiomorpholinoazetidin-1-yl)methyl)pyrido[3,2-d]pyrimidin-4-yl)morpholine |
| 130 | 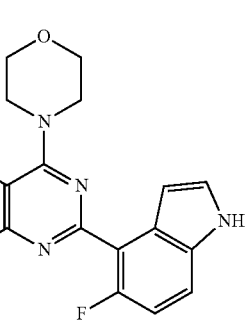 | 4-(2-(5-fluoro-1H-indol-4-yl)-6-((4-(oxetan-3-yl)piperidin-1-yl)methyl)pyrido[3,2-d]pyrimidin-4-yl)morpholine |

TABLE 1-continued

| No. | Structure | Name |
|---|---|---|
| 131 | 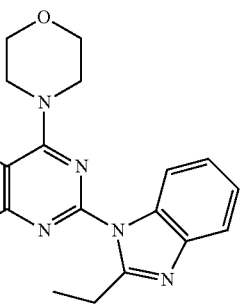 | 4-(1-((2-(2-ethyl-1H-benzo[d]imidazol-1-yl)-4-morpholinopyrido[3,2-d]pyrimidin-6-yl)methyl)azetidin-3-yl)morpholine |
| 132 | 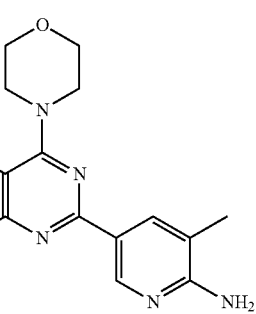 | 2-(1-((2-(6-amino-5-methylpyridin-3-yl)-4-morpholinopyrido[3,2-d]pyrimidin-6-yl)methyl)piperidin-4-yl)propan-2-ol |
| 133 | 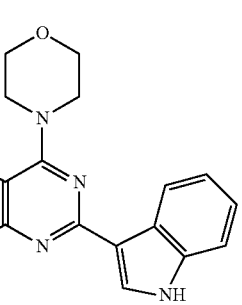 | 2-(1-((2-(1H-indol-3-yl)-4-morpholinopyrido[3,2-d]pyrimidin-6-yl)methyl)piperidin-4-yl)propan-2-ol |
| 134 | 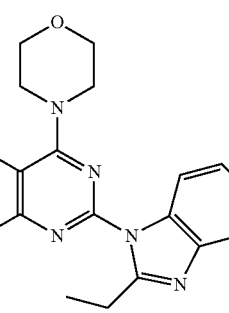 | 4-(1-((2-(2-ethyl-1H-benzo[d]imidazol-1-yl)-4-morpholinopyrido[3,2-d]pyrimidin-6-yl)methyl)azetidin-3-yl)piperazin-2-one |

TABLE 2

| No. | Structure | Name |
|---|---|---|
| 135 | 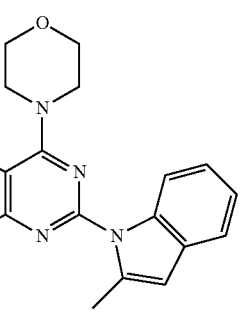 | 2-(1-((2-(2-methyl-1H-indol-1-yl)-4-morpholinopyrido[3,2-d]pyrimidin-6-yl)methyl)piperidin-4-yl)propan-2-ol |
| 136 | 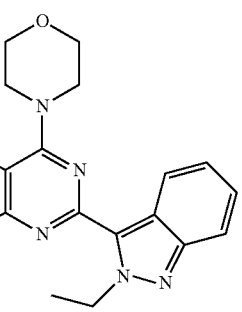 | 2-(1-((2-(2-ethyl-2H-indazol-3-yl)-4-morpholinopyrido[3,2-d]pyrimidin-6-yl)methyl)piperidin-4-yl)propan-2-ol |
| 137 | 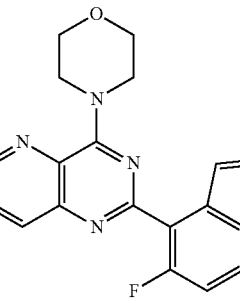 | tert-butyl 4-((2-(5-fluoro-1H-indol-4-yl)-4-morpholinopyrido[3,2-d]pyrimidin-6-yl)methyl)piperidine-1-carboxylate |
| 138 | 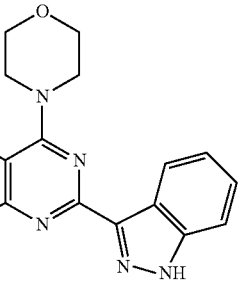 | 2-(1-((2-(1H-indazol-3-yl)-4-morpholinopyrido[3,2-d]pyrimidin-6-yl)methyl)piperidin-4-yl)propan-2-ol |
| 139 | 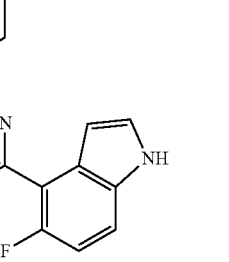 | 4-(2-(5-fluoro-1H-indol-4-yl)-6-(piperidin-4-ylmethyl)pyrido[3,2-d]pyrimidin-4-yl)morpholine |

TABLE 2-continued

| No. | Structure | Name |
|---|---|---|
| 140 | 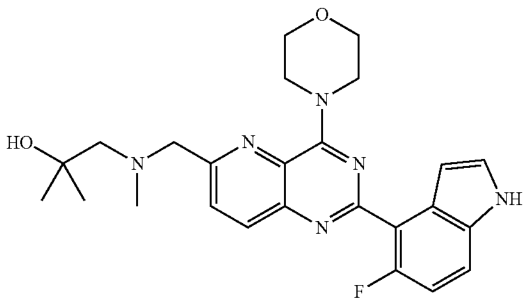 | 1-(((2-(5-fluoro-1H-indol-4-yl)-4-morpholinopyrido[3,2-d]pyrimidin-6-yl)methyl)(methyl)amino)-2-methylpropan-2-ol |
| 141 | 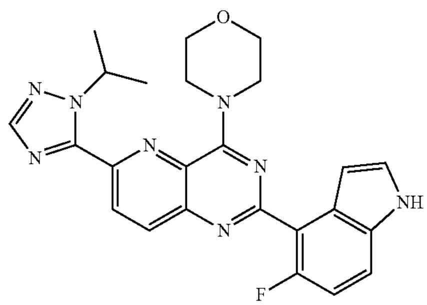 [SMILES: CC(C)n1ncnc1-c1ccc2nc(-c3c(F)ccc4[nH]ccc34)nc(N3CCOCC3)c2n1] | 4-(2-(5-fluoro-1H-indol-4-yl)-6-(1-isopropyl-1H-1,2,4-triazol-5-yl)pyrido[3,2-d]pyrimidin-4-yl)morpholine |
| 142 | 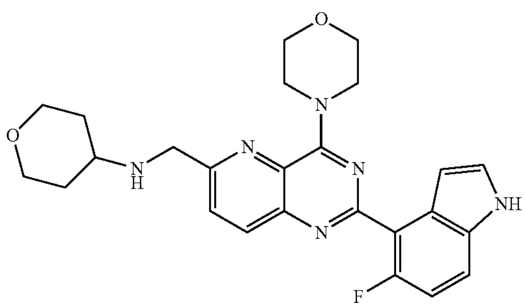 [SMILES: Fc1ccc2[nH]ccc2c1-c1nc(N2CCOCC2)c2nc(CNC3CCOCC3)ccc2n1] | N-((2-(5-fluoro-1H-indol-4-yl)-4-morpholinopyrido[3,2-d]pyrimidin-6-yl)methyl)tetrahydro-2H-pyran-4-amine |
| 143 | 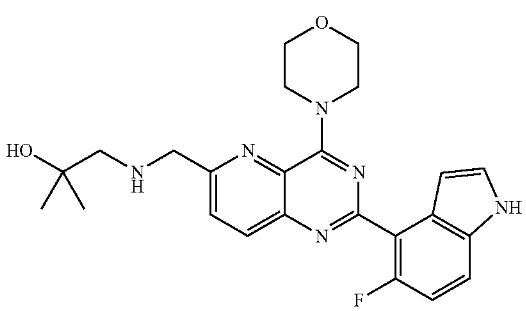 [SMILES: CC(C)(O)CNCc1ccc2nc(-c3c(F)ccc4[nH]ccc34)nc(N3CCOCC3)c2n1] | 1-((2-(5-fluoro-1H-indol-4-yl)-4-morpholinopyrido[3,2-d]pyrimidin-6-yl)methylamino)-2-methylpropan-2-ol |
| 144 | 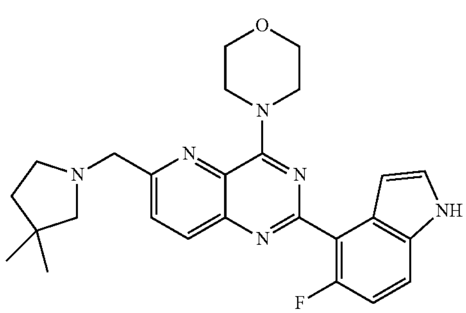 [SMILES: CC1(C)CCN(Cc2ccc3nc(-c4c(F)ccc5[nH]ccc45)nc(N4CCOCC4)c3n2)C1] | 4-(6-((3,3-dimethylpyrrolidin-1-yl)methyl)-2-(5-fluoro-1H-indol-4-yl)pyrido[3,2-d]pyrimidin-4-yl)morpholine |

TABLE 2-continued

| No. | Structure | Name |
|---|---|---|
| 145 | 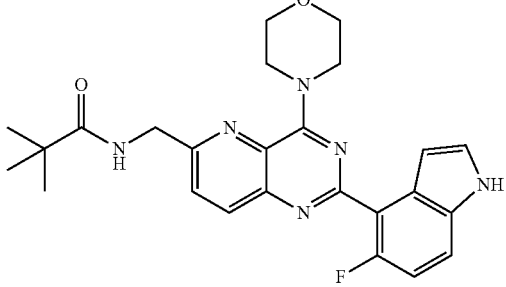 | N-((2-(5-fluoro-1H-indol-4-yl)-4-morpholinopyrido[3,2-d]pyrimidin-6-yl)methyl)pivalamide |
| 146 | 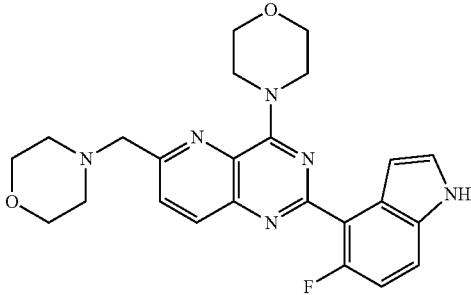 [SMILES: Fc1ccc2[nH]ccc2c1-c1nc(N2CCOCC2)c2nc(CN3CCOCC3)ccc2n1] | 4-((2-(5-fluoro-1H-indol-4-yl)-4-morpholinopyrido[3,2-d]pyrimidin-6-yl)methyl)morpholine |
| 147 | 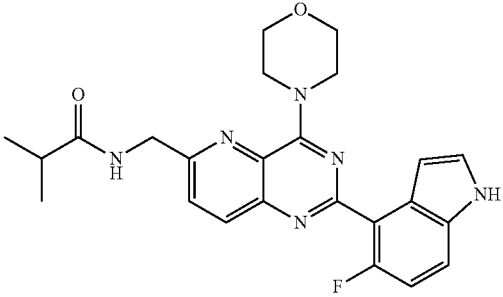 [SMILES: CC(C)C(=O)NCc1ccc2nc(-c3c(F)ccc4[nH]ccc34)nc(N3CCOCC3)c2n1] | N-((2-(5-fluoro-1H-indol-4-yl)-4-morpholinopyrido[3,2-d]pyrimidin-6-yl)methyl)isobutyramide |
| 148 | 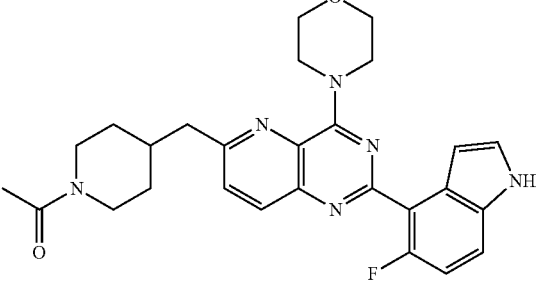 | 1-(4-((2-(5-fluoro-1H-indol-4-yl)-4-morpholinopyrido[3,2-d]pyrimidin-6-yl)methyl(piperidin-1-yl)ethanone |
| 149 | 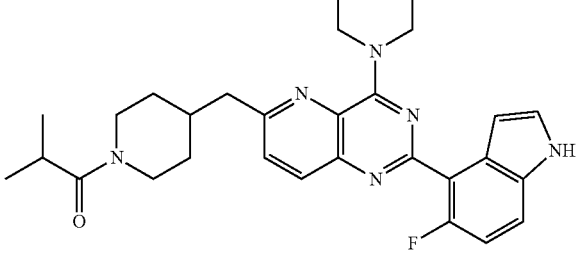 | 1-(4-((2-(5-fluoro-1H-indol-4-yl)-4-morpholinopyrido[3,2-d]pyrimidin-6-yl)methyl)piperidin-1-yl)-2-methylpropan-1-one |

TABLE 2-continued

| No. | Structure | Name |
|---|---|---|
| 150 | 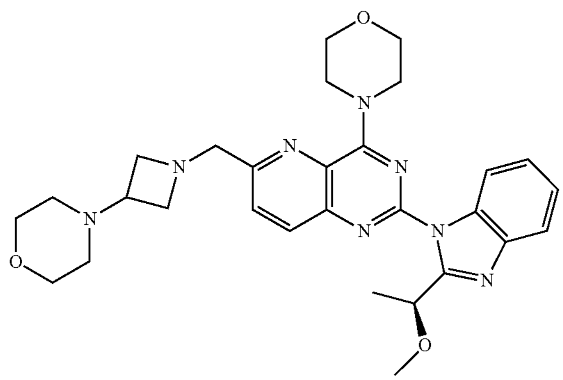 [SMILES: CO[C@@H](C)c1nc2ccccc2n1-c1nc(N2CCOCC2)c2nc(CN3CC(N4CCOCC4)C3)ccc2n1] | (S)-4-(1-((2-(2-(1-methoxyethyl)-1H-benzo[d]imidazol-1-yl)-4-morpholinopyrido[3,2-d]pyrimidin-6-yl)methyl)azetidin-3-yl)morpholine |
| 151 | 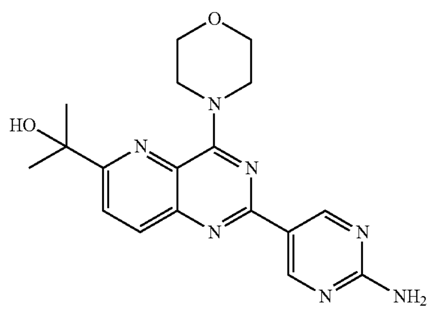 [SMILES: CC(C)(O)c1ccc2nc(-c3cnc(N)nc3)nc(N3CCOCC3)c2n1] | 2-(2-(2-aminopyrimidin-5-yl)-4-morpholinopyrido[3,2-d]pyrimidin-6-yl)propan-2-ol |
| 152 | 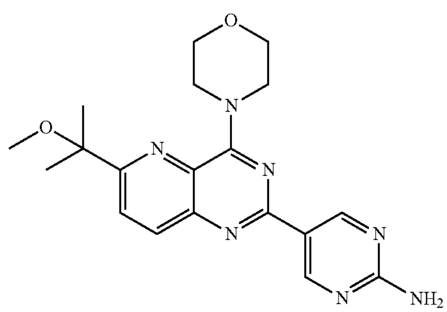 [SMILES: COC(C)(C)c1ccc2nc(-c3cnc(N)nc3)nc(N3CCOCC3)c2n1] | 5-(6-(2-methoxypropan-2-yl)-4-morpholinopyrido[3,2-d]pyrimidin-2-yl)pyrimidin-2-amine |
| 153 | 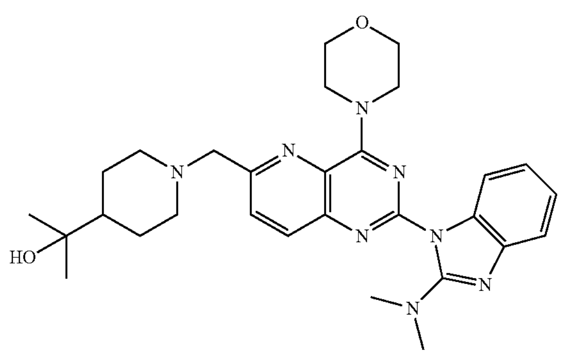 [SMILES: CN(C)c1nc2ccccc2n1-c1nc(N2CCOCC2)c2nc(CN3CCC(C(C)(C)O)CC3)ccc2n1] | 2-(1-((2-(2-(dimethylamino)-1H-benzo[d]imidazol-1-yl)-4-morpholinopyrido[3,2-d]pyrimidin-6-yl)methyl)piperidin-4-yl)propan-2-ol |

TABLE 2-continued

| No. | Structure | Name |
|---|---|---|
| 154 | 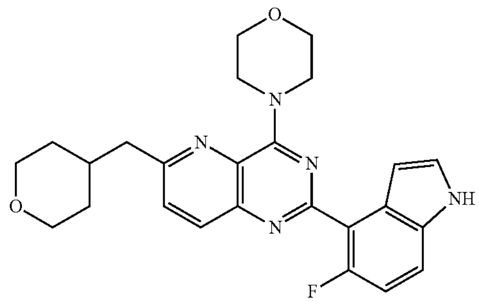 | 4-(2-(5-fluoro-1H-indol-4-yl)-6-((tetrahydro-2H-pyran-4-yl)methyl)pyrido[3,2-d]pyrimidin-4-yl)morpholine |
| 155 | 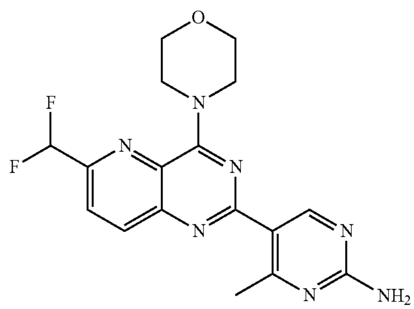 [SMILES: Cc1nc(N)ncc1-c1nc(N2CCOCC2)c2nc(C(F)F)ccc2n1] | 5-(6-(difluoromethyl)-4-morpholinopyrido[3,2-d]pyrimidin-2-yl)-4-methylpyrimidin-2-amine |
| 156 | 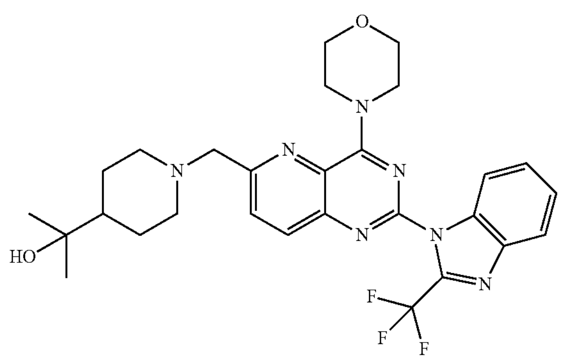 [SMILES: CC(C)(O)C1CCN(Cc2ccc3nc(-n4c(C(F)(F)F)nc5ccccc54)nc(N4CCOCC4)c3n2)CC1] | 2-(1-((4-morpholino-2-(2-(trifluoromethyl)-1H-benzo[d]imidazol-1-yl)pyrido[3,2-d]pyrimidin-6-yl)methyl)piperidin-4-yl)propan-2-ol |
| 157 | 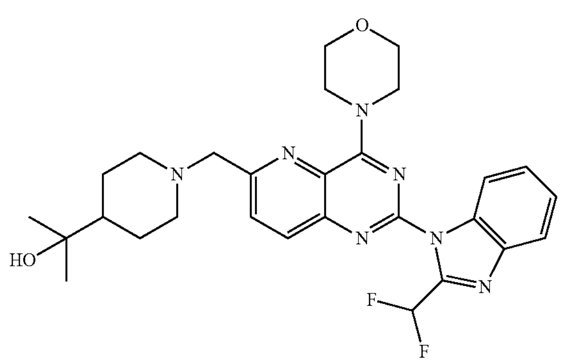 [SMILES: CC(C)(O)C1CCN(Cc2ccc3nc(-n4c(C(F)F)nc5ccccc54)nc(N4CCOCC4)c3n2)CC1] | 2-(1-((2-(2-(difluoromethyl)-1H-benzo[d]imidazol-1-yl)-4-morpholinopyrido[3,2-d]pyrimidin-6-yl)methyl)piperidin-4-yl)propan-2-ol |

TABLE 2-continued

| No. | Structure | Name |
|---|---|---|
| 158 | 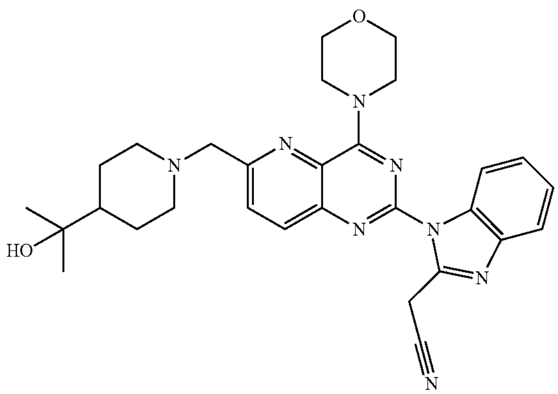 [SMILES: CC(C)(O)C1CCN(Cc2ccc3nc(-n4c(CC#N)nc5ccccc54)nc(N4CCOCC4)c3n2)CC1] | 2-(1-(6-((4-(2-hydroxypropan-2-yl)piperidin-1-yl)methyl)-4-morpholinopyrido[3,2-d]pyrimidin-2-yl)-1H-benzo[d]imidazol-2-yl)acetonitrile |
| 159 | 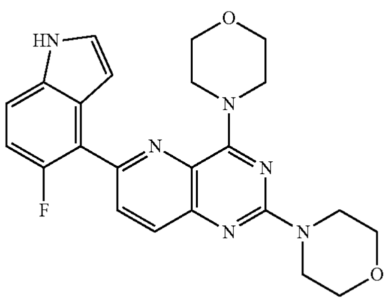 [SMILES: Fc1ccc2[nH]ccc2c1-c1ccc2nc(N3CCOCC3)nc(N3CCOCC3)c2n1] | 4,4'-(6-(5-fluoro-1H-indol-4-yl)pyrido[3,2-d]pyrimidine-2,4-diyl)dimorpholine |
| 160 | 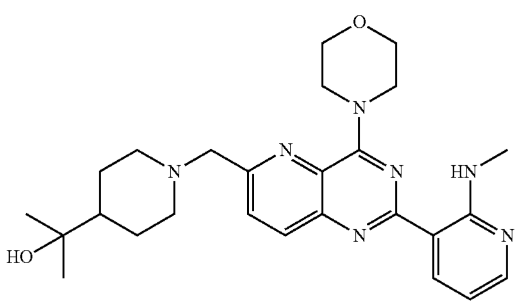 [SMILES: CNc1ncccc1-c1nc(N2CCOCC2)c2nc(CN3CCC(C(C)(C)O)CC3)ccc2n1] | 2-(1-((2-(2-(methylamino)pyridin-3-yl)-4-morpholinopyrido[3,2-d]pyrimidin-6-yl)methyl)piperidin-4-yl)propan-2-ol |
| 161 | 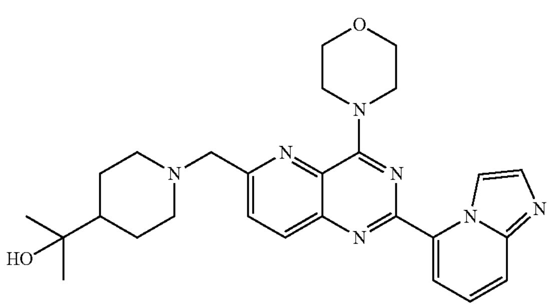 [SMILES: CC(C)(O)C1CCN(Cc2ccc3nc(-c4cccc5nccn45)nc(N4CCOCC4)c3n2)CC1] | 2-(1-((2-(imidazo[1,2-a]pyridin-5-yl)-4-morpholinopyrido[3,2-d]pyrimidin-6-yl)methyl)piperidin-4-yl)propan-2-ol |
| 162 | 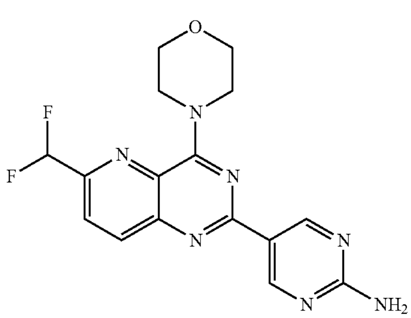 [SMILES: Nc1ncc(-c2nc(N3CCOCC3)c3nc(C(F)F)ccc3n2)cn1] | 5-(6-(difluoromethyl)-4-morpholinopyrido[3,2-d]pyrimidin-2-yl)pyrimidin-2-amine |

TABLE 2-continued

| No. | Structure | Name |
|---|---|---|
| 163 | 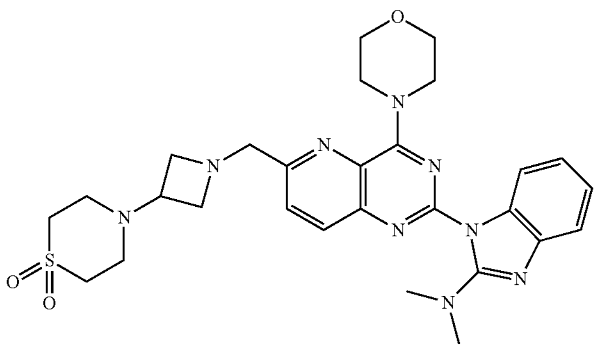 [SMILES: CN(C)c1nc2ccccc2n1-c1nc(N2CCOCC2)c2nc(CN3CC(N4CCS(=O)(=O)CC4)C3)ccc2n1] | N,N-dimethyl-1-(4-morpholino-6-((3-(1,1-dioxo)thiomorpholinoazetidin-1-yl)methyl)pyrido[3,2-d]pyrimidin-2-yl)-1H-benzo[d]imidazol-2-amine |
| 164 | 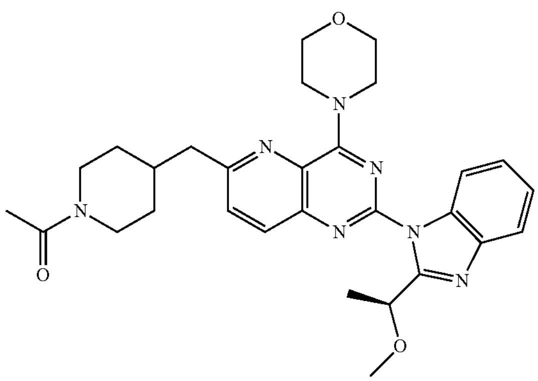 [SMILES: CO[C@@H](C)c1nc2ccccc2n1-c1nc(N2CCOCC2)c2nc(CC3CCN(C(C)=O)CC3)ccc2n1] | (S)-1-(4-((2-(2-(1-methoxyethyl)-1H-benzo[d]imidazol-1-yl)-4-morpholinopyrido[3,2-d]pyrimidin-6-yl)methyl)piperidin-1-yl)ethanone |
| 165 | 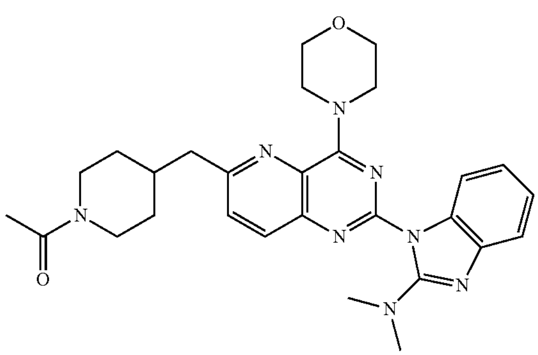 [SMILES: CC(=O)N1CCC(Cc2ccc3nc(-n4c(N(C)C)nc5ccccc54)nc(N4CCOCC4)c3n2)CC1] | 1-(4-((2-(2-(dimethylamino)-1H-benzo[d]imidazol-1-yl)-4-morpholinopyrido[3,2-d]pyrimidin-6-yl)methyl)piperidin-1-yl)ethanone |
| 166 | 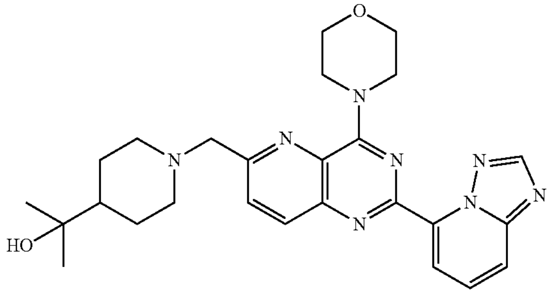 [SMILES: CC(C)(O)C1CCN(Cc2ccc3nc(-c4cccc5ncnn45)nc(N4CCOCC4)c3n2)CC1] | 2-(1-((2-([1,2,4]triazolo[1,5-a]pyridin-5-yl)-4-morpholinopyrido[3,2-d]pyrimidin-6-yl)methyl)piperidin-4-yl)propan-2-ol |

TABLE 2-continued

| No. | Structure | Name |
|---|---|---|
| 167 | 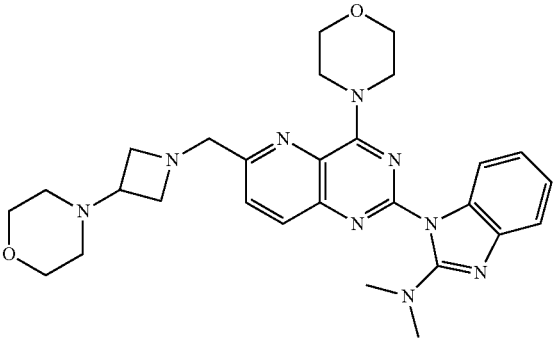 [SMILES: CN(C)c1nc2ccccc2n1-c1nc(N2CCOCC2)c2nc(CN3CC(N4CCOCC4)C3)ccc2n1] | N,N-dimethyl-1-(4-morpholino-6-((3-morpholinoazetidin-1-yl)methyl)pyrido[3,2-d]pyrimidin-2-yl)-1H-benzo[d]imidazol-2-amine |
| 168 | 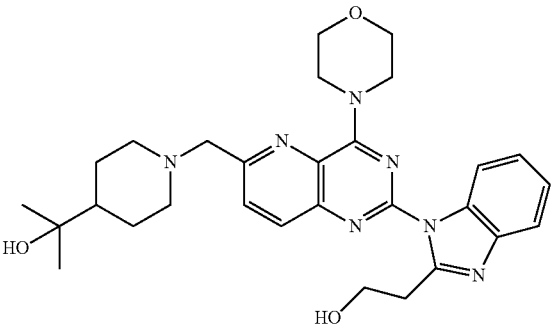 [SMILES: CC(C)(O)C1CCN(Cc2ccc3nc(-n4c(CCO)nc5ccccc54)nc(N4CCOCC4)c3n2)CC1] | 2-(1-((2-(2-(2-hydroxyethyl)-1H-benzo[d]imidazol-1-yl)-4-morpholinopyrido[3,2-d]pyrimidin-6-yl)methyl)piperidin-4-yl)propan-2-ol |
| 169 | 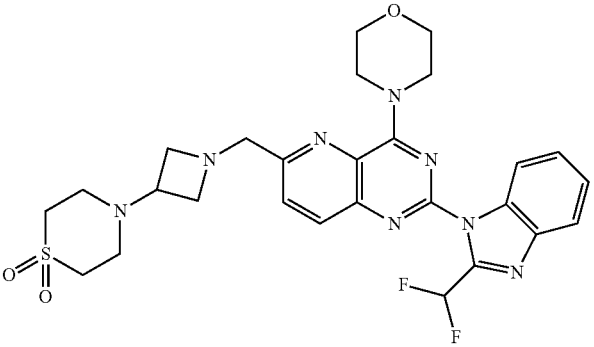 [SMILES: O=S1(=O)CCN(C2CN(Cc3ccc4nc(-n5c(C(F)F)nc6ccccc65)nc(N5CCOCC5)c4n3)C2)CC1] | 4-(2-(2-(difluoromethyl)-1H-benzo[d]imidazol-1-yl)-6-((3-(1,1-dioxo)thiomorpholinoazetidin-1-yl)methyl)pyrido[3,2-d]pyrimidin-4-yl)morpholine |
| 170 | 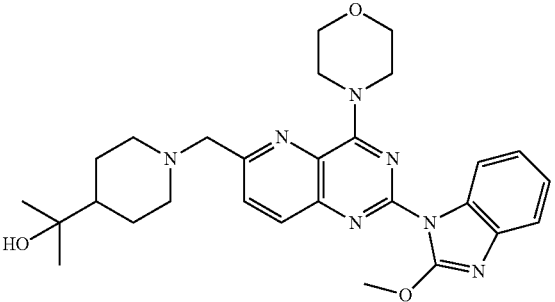 [SMILES: COc1nc2ccccc2n1-c1nc(N2CCOCC2)c2nc(CN3CCC(C(C)(C)O)CC3)ccc2n1] | 2-(1-((2-(2-methoxy-1H-benzo[d]imidazol-1-yl)-4-morpholinopyrido[3,2-d]pyrimidin-6-yl)methyl)piperidin-4-yl)propan-2-ol |

TABLE 2-continued

| No. | Structure | Name |
|---|---|---|
| 171 | 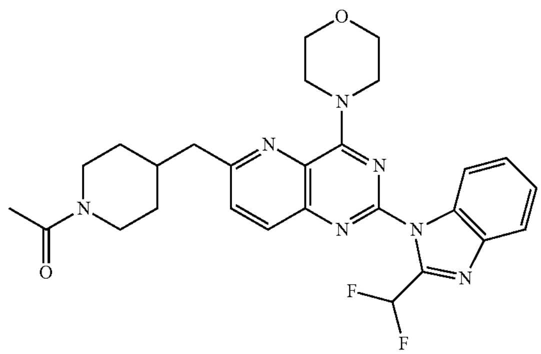 [SMILES: CC(=O)N1CCC(Cc2ccc3nc(-n4c(C(F)F)nc5ccccc54)nc(N4CCOCC4)c3n2)CC1] | 1-(4-((2-(2-(difluoromethyl)-1H-benzo[d]imidazol-1-yl)-4-morpholinopyrido[3,2-d]pyrimidin-6-yl)methyl)piperidin-1-yl)ethanone |
| 172 | 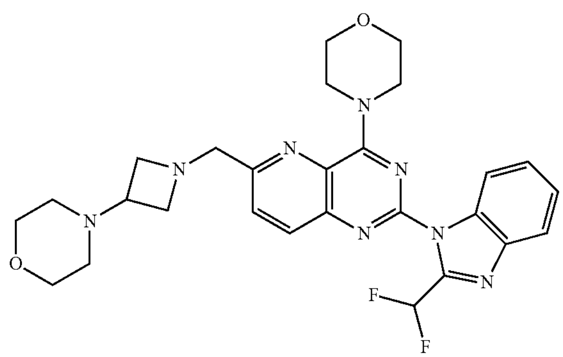 [SMILES: FC(F)c1nc2ccccc2n1-c1nc(N2CCOCC2)c2nc(CN3CC(N4CCOCC4)C3)ccc2n1] | 4-(1-((2-(2-(difluoromethyl)-1H-benzo[d]imidazol-1-yl)-4-morpholinopyrido[3,2-d]pyrimidin-6-yl)methyl)azetidin-3-yl)morpholine |
| 173 | 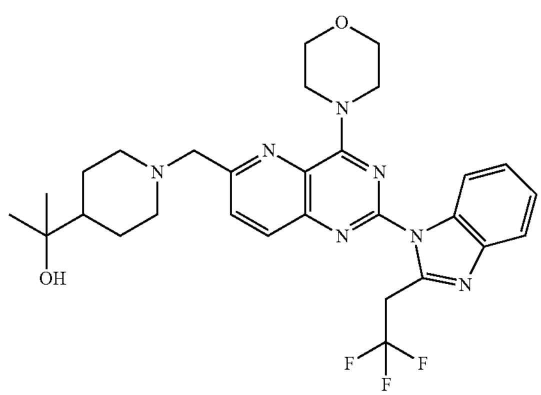 [SMILES: CC(C)(O)C1CCN(Cc2ccc3nc(-n4c(CC(F)(F)F)nc5ccccc54)nc(N4CCOCC4)c3n2)CC1] | 2-(1-((4-morpholino-2-(2-(2,2,2-trifluoroethyl)-1H-benzo[d]imidazol-1-yl)pyrido[3,2-d]pyrimidin-6-yl)methyl)piperidin-4-yl)propan-2-ol |
| 174 | 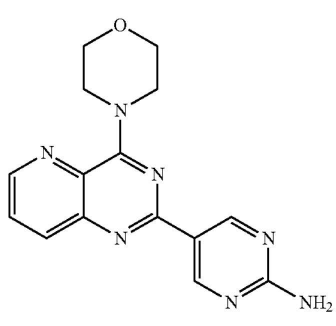 [SMILES: Nc1ncc(-c2nc(N3CCOCC3)c3ncccc3n2)cn1] | 5-(4-morpholinopyrido[3,2-d]pyrimidin-2-yl)pyrimidin-2-amine |

TABLE 2-continued

| No. | Structure | Name |
|---|---|---|
| 175 | 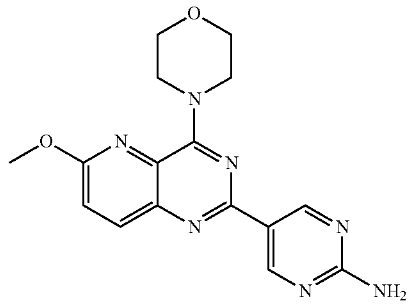 [SMILES: COc1ccc2nc(-c3cnc(N)nc3)nc(N3CCOCC3)c2n1] | 5-(6-methoxy-4-morpholinopyrido[3,2-d]pyrimidin-2-yl)pyrimidin-2-amine |
| 176 | 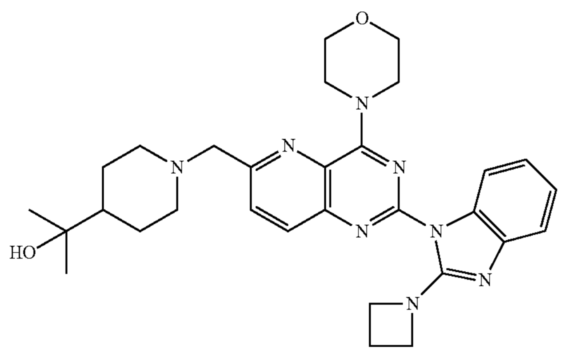 [SMILES: CC(C)(O)C1CCN(Cc2ccc3nc(-n4c(N5CCC5)nc5ccccc54)nc(N4CCOCC4)c3n2)CC1] | 2-(1-((2-(2-(azetidin-1-yl)-1H-benzo[d]imidazol-1-yl)-4-morpholinopyrido[3,2-d]pyrimidin-6-yl)methyl)piperidin-4-yl)propan-2-ol |
| 177 | 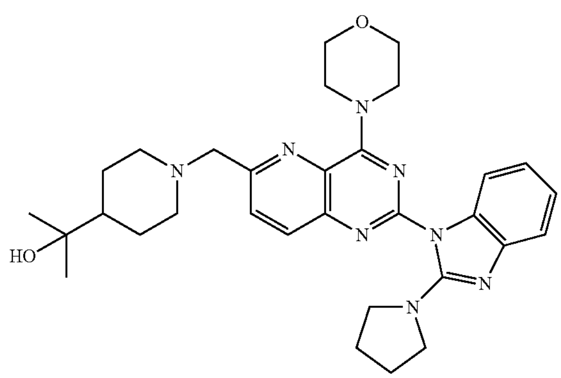 [SMILES: CC(C)(O)C1CCN(Cc2ccc3nc(-n4c(N5CCCC5)nc5ccccc54)nc(N4CCOCC4)c3n2)CC1] | 2-(1-((4-morpholino-2-(2-(pyrrolidin-1-yl)-1H-benzo[d]imidazol-1-yl)pyrido[3,2-d]pyrimidin-6-yl)methyl)piperidin-4-yl)propan-2-ol |
| 178 | 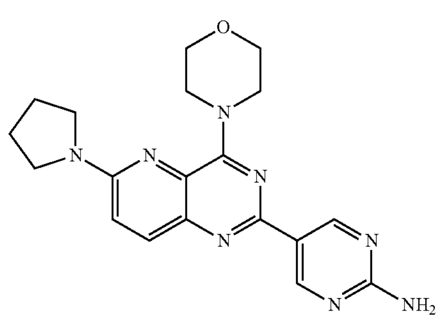 [SMILES: Nc1ncc(-c2nc(N3CCOCC3)c3nc(N4CCCC4)ccc3n2)cn1] | 5-(4-morpholino-6-(pyrrolidin-1-yl)pyrido[3,2-d]pyrimidin-2-yl)pyrimidin-2-amine |

TABLE 2-continued

| No. | Structure | Name |
|---|---|---|
| 179 | 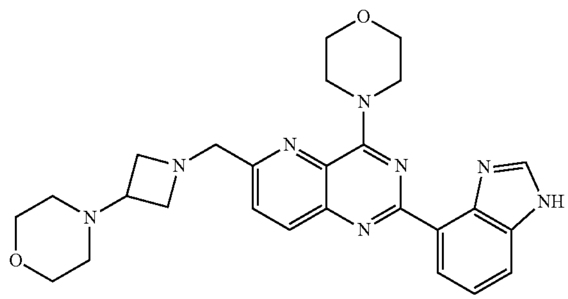 [SMILES: c1cc(-c2nc(N3CCOCC3)c3nc(CN4CC(N5CCOCC5)C4)ccc3n2)c2nc[nH]c2c1] | 4-(1-((2-(1H-benzo[d]imidazol-4-yl)-4-morpholinopyrido[3,2-d]pyrimidin-6-yl)methyl)azetidin-3-yl)morpholine |
| 180 | 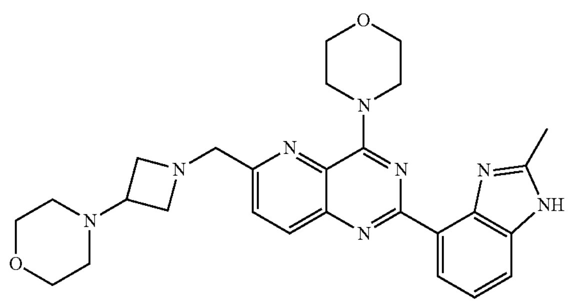 [SMILES: Cc1nc2c(-c3nc(N4CCOCC4)c4nc(CN5CC(N6CCOCC6)C5)ccc4n3)cccc2[nH]1] | 4-(1-((2-(2-methyl-1H-benzo[d]imidazol-4-yl)-4-morpholinopyrido[3,2-d]pyrimidin-6-yl)methyl)azetidin-3-yl)morpholine |
| 181 | 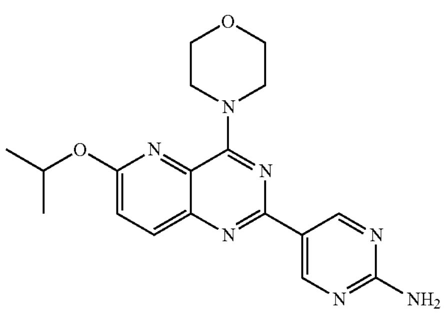 [SMILES: CC(C)Oc1ccc2nc(-c3cnc(N)nc3)nc(N3CCOCC3)c2n1] | 5-(6-isopropoxy-4-morpholinopyrido[3,2-d]pyrimidin-2-yl)pyrimidin-2-amine |
| 182 | 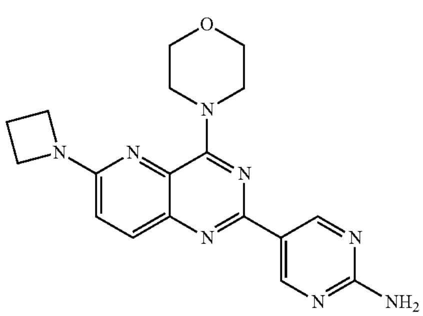 [SMILES: Nc1ncc(-c2nc(N3CCOCC3)c3nc(N4CCC4)ccc3n2)cn1] | 5-(6-(azetidin-1-yl)-4-morpholinopyrido[3,2-d]pyrimidin-2-yl)pyrimidin-2-amine |
| 183 | 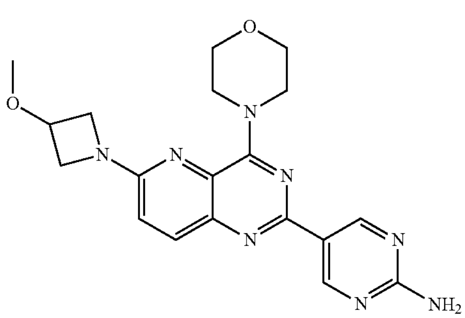 | 5-(6-(3-methoxyazetidin-1-yl)-4-morpholinopyrido[3,2-d]pyrimidin-2-yl)pyrimidin-2-amine |

TABLE 2-continued

| No. | Structure | Name |
|---|---|---|
| 184 | 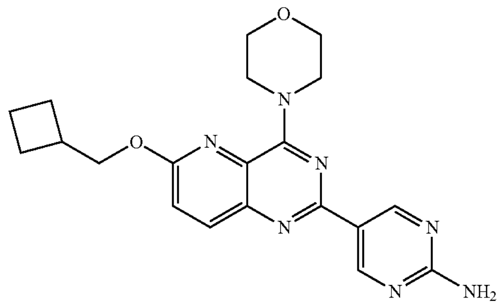 [SMILES: Nc1ncc(-c2nc(N3CCOCC3)c3nc(OCC4CCC4)ccc3n2)cn1] | 5-(6-(cyclobutylmethoxy)-4-morpholinopyrido[3,2-d]pyrimidin-2-yl)pyrimidin-2-amine |
| 185 | 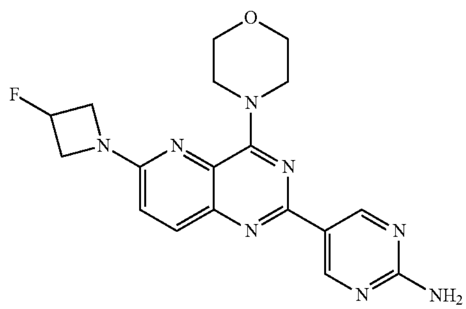 [SMILES: Nc1ncc(-c2nc(N3CCOCC3)c3nc(N4CC(F)C4)ccc3n2)cn1] | 5-(6-(3-fluoroazetidin-1-yl)-4-morpholinopyrido[3,2-d]pyrimidin-2-yl)pyrimidin-2-amine |
| 186 | 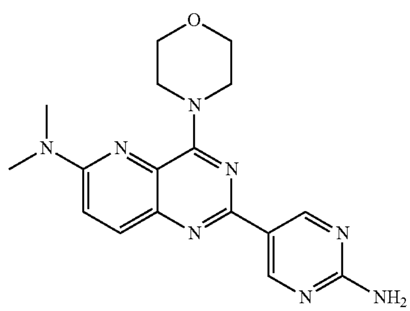 [SMILES: CN(C)c1ccc2nc(-c3cnc(N)nc3)nc(N3CCOCC3)c2n1] | 2-(2-aminopyrimidin-5-yl)-N,N-dimethyl-4-morpholinopyrido[3,2-d]pyrimidin-6-amine |
| 187 | 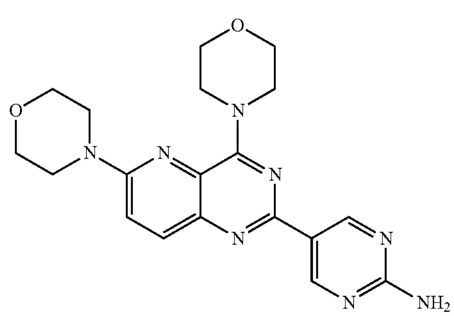 [SMILES: Nc1ncc(-c2nc(N3CCOCC3)c3nc(N4CCOCC4)ccc3n2)cn1] | 5-(4,6-dimorpholinopyrido[3,2-d]pyrimidin-2-yl)pyrimidin-2-amine |
| 188 | 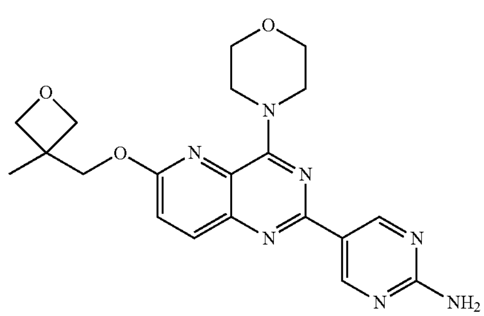 [SMILES: CC1(COc2ccc3nc(-c4cnc(N)nc4)nc(N4CCOCC4)c3n2)COC1] | 5-(6-((3-methyloxetan-3-yl)methoxy)-4-morpholinopyrido[3,2-d]pyrimidin-2-yl)pyrimidin-2-amine |

TABLE 2-continued

| No. | Structure | Name |
|---|---|---|
| 189 | 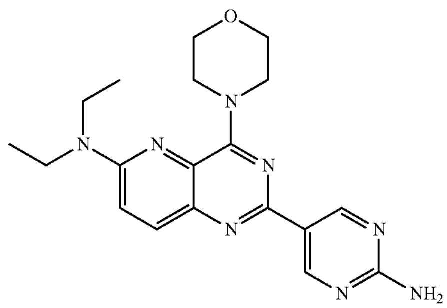 [SMILES: CCN(CC)c1ccc2nc(-c3cnc(N)nc3)nc(N3CCOCC3)c2n1] | 2-(2-aminopyrimidin-5-yl)-N,N-diethyl-4-morpholinopyrido[3,2-d]pyrimidin-6-amine |
| 190 | 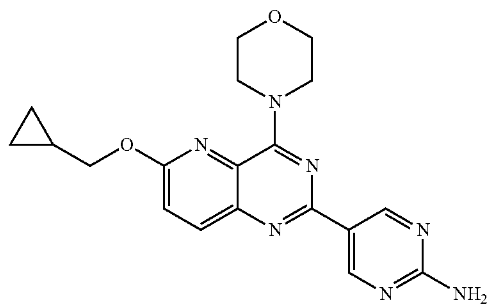 [SMILES: Nc1ncc(-c2nc(N3CCOCC3)c3nc(OCC4CC4)ccc3n2)cn1] | 5-(6-(cyclopropylmethoxy)-4-morpholinopyrido[3,2-d]pyrimidin-2-yl)pyrimidin-2-amine |
| 191 | 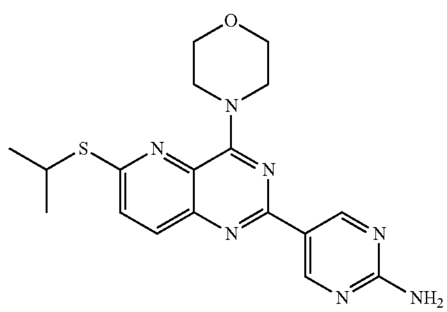 | 5-(6-(isopropylthio)-4-morpholinopyrido[3,2-d]pyrimidin-2-yl)pyrimidin-2-amine |
| 192 | 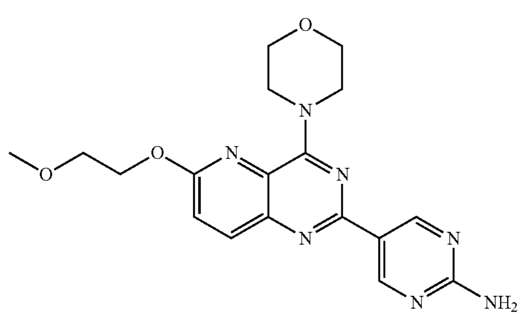 [SMILES: COCCOc1ccc2nc(-c3cnc(N)nc3)nc(N3CCOCC3)c2n1] | 5-(6-(2-methoxyethoxy)-4-morpholinopyrido[3,2-d]pyrimidin-2-yl)pyrimidin-2-amine |
| 193 | 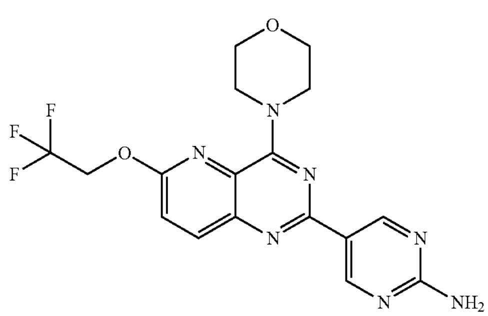 [SMILES: Nc1ncc(-c2nc(N3CCOCC3)c3nc(OCC(F)(F)F)ccc3n2)cn1] | 5-(4-morpholino-6-(2,2,2-trifluoroethoxy)pyrido[3,2-d]pyrimidin-2-yl)pyrimidin-2-amine |

TABLE 2-continued

| No. | Structure | Name |
|---|---|---|
| 194 | 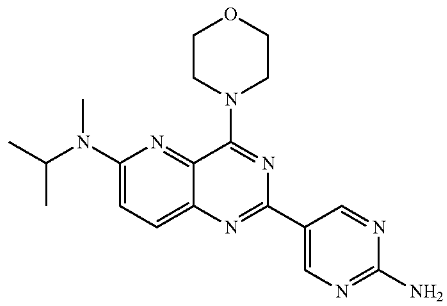 [SMILES: CC(C)N(C)c1ccc2nc(-c3cnc(N)nc3)nc(N3CCOCC3)c2n1] | 2-(2-aminopyrimidin-5-yl)-N-isopropyl-N-methyl-4-morpholinopyrido[3,2-d]pyrimidin-6-amine |
| 195 | 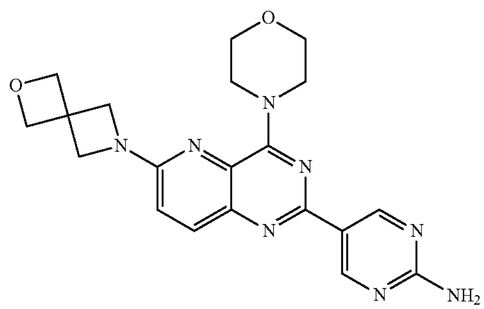 [SMILES: Nc1ncc(-c2nc(N3CCOCC3)c3nc(N4CC5(COC5)C4)ccc3n2)cn1] | 5-(4-morpholino-6-(2-oxa-6-azaspiro[3.3]heptan-6-yl)pyrido[3,2-d]pyrimidin-2-yl)pyrimidin-2-amine |
| 196 | 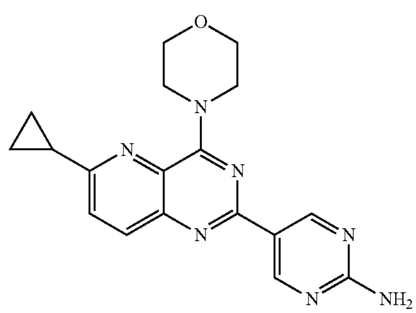 [SMILES: Nc1ncc(-c2nc(N3CCOCC3)c3nc(C4CC4)ccc3n2)cn1] | 5-(6-cyclopropyl-4-morpholinopyrido[3,2-d]pyrimidin-2-yl)pyrimidin-2-amine |
| 197 | 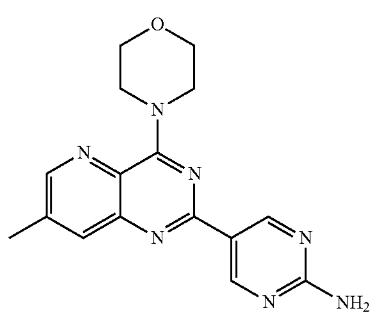 [SMILES: Cc1cnc2c(N3CCOCC3)nc(-c3cnc(N)nc3)nc2c1] | 5-(7-methyl-4-morpholinopyrido[3,2-d]pyrimidin-2-yl)pyrimidin-2-amine |
| 198 | 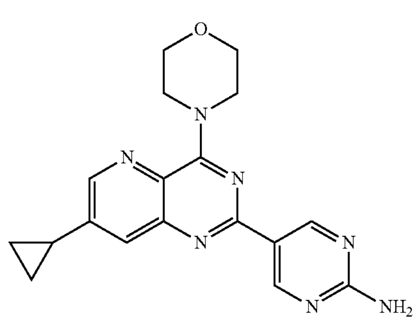 [SMILES: Nc1ncc(-c2nc(N3CCOCC3)c3ncc(C4CC4)cc3n2)cn1] | 5-(7-cyclopropyl-4-morpholinopyrido[3,2-d]pyrimidin-2-yl)pyrimidin-2-amine |

TABLE 2-continued

| No. | Structure | Name |
|---|---|---|
| 199 | 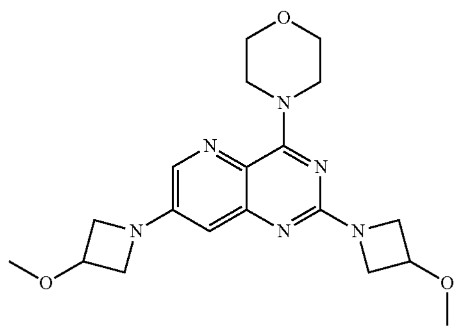 | 4-(2,7-bis(3-methoxyazetidin-1-yl)pyrido[3,2-d]pyrimidin-4-yl)morpholine |
| 200 | 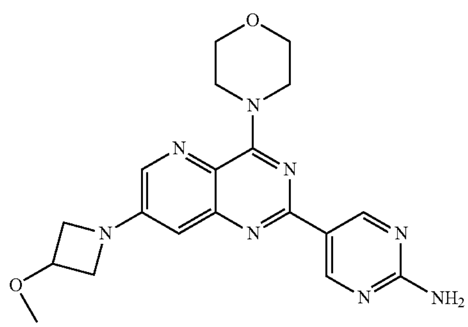 [SMILES: COC1CN(c2cnc3c(N4CCOCC4)nc(-c4cnc(N)nc4)nc3c2)C1] | 5-(7-(3-methoxyazetidin-1-yl)-4-morpholinopyrido[3,2-d]pyrimidin-2-yl)pyrimidin-2-amine |
| 201 | 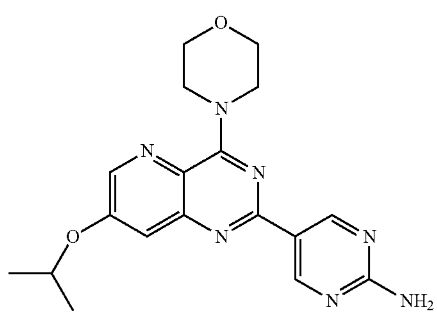 [SMILES: CC(C)Oc1cnc2c(N3CCOCC3)nc(-c3cnc(N)nc3)nc2c1] | 5-(7-isopropoxy-4-morpholinopyrido[3,2-d]pyrimidin-2-yl)pyrimidin-2-amine |

Administration of Formula I Compounds

The Formula I compounds of the invention may be administered by a route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from function or behavior associated with PI3 kinase, in particular with the p110δ (delta) isoform of PI3 kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from abnormal cell growth or cellular proliferative diseases such as tumor and/or cancerous cell growth mediated by PI3K may also be treated by a method comprising the administration thereto of a Formula I compound. The condition of the patient may thereby be improved or ameliorated. In particular, the compounds are useful in the treatment of human or animal (e.g., murine) cancers, including, for example, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, myeloid leukemia, oral cavity and pharynx, non-Hodgkin lymphoma, melanoma, and villous colon adenoma.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3K delta activity may result in reduced amounts of reperfusion injury in such situations.

Methods of the invention also include treating cancer in a mammal comprised of administering to said mammal a therapeutically effective amount of a Formula I compound wherein the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's or leukemia.

Formula I compounds may be useful for treating conditions of the brain and central nervous system which require transport across the blood-brain barrier. Certain Formula I compounds have favorable penetrant properties across the blood-brain barrier for delivery to the brain. Disorders of the brain which may be effectively treated with Formula I compounds include metastatic and primary brain tumors, such as glioblastoma and melanoma.

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Formulations include where the particle size of a Formula I compound is between 10-1000 nm, or between 10-400 nm. Such pharmaceutical formulations may be useful for a Formula I compound with poor bioavailability based upon the principle that bioavailability can be increased by increasing the surface area by decreasing particle size (U.S. Pat. No. 4,107,288, U.S. Pat. No. 5,145,684) to the size range from 10 to 1,000 nm where the Formula I compound is supported on a cross linked matrix of macromolecules.

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) $16^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16$^{th}$ edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner, including a mixture of at least one emulsifier with a fat or an oil, or with both a fat and an oil. A hydrophilic emulsifier included together with a lipophilic emulsifier acts as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr (hour) can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, geometric isomer, tautomer, solvate, metabolite, or pharmaceutically acceptable salt or prodrug thereof, in combination with a therapeutic agent such as an NSAID.

Combination refers to either a fixed combination in one dosage unit form, or a kit of parts for the combined administration where a compound of Formula I and a second therapeutic agent may be administered independently at the same time or separately within time intervals, especially where these time intervals allow that the combination partners show a cooperative, e.g. synergistic effect. The combination therapy methods and compositions of the invention are meant to encompass administration of the selected combination to a single subject in need thereof (e.g. a patient), and are intended to include treatment regimens in which the agents are not necessarily administered by the same route of administration or at the same time. The term "pharmaceutical combination" means a product that results from the mixing or combining of more than one active ingredient and includes both fixed and non-fixed combinations of the active ingredients. The term "fixed combination" means that the active ingredients, e.g. a compound of Formula I and a second therapeutic combination partner, are both administered to a patient simultaneously in the form of a single entity or dosage. The term "non-fixed combination" means that the active ingredients, e.g. a compound of Formula I and a second therapeutic combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, geometric isomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

For certain embodiments, Formula I compounds may be readily prepared using well-known procedures to prepare pyrido[3,2-d]pyrimidine compounds, including the route of Scheme 1 and the methods of: Srinivasan and Broom (1981) J. Org. Chem. 46:1777-1781; Malagu K. et al (2009) Bioorg. & Med. Chem. Letters 19(20):5950-5953; Hayakawa M. et al (2006) Bioorg. & Med. Chem. 14(20):6847-6858; Nishikawa, K. et al (1976) Chem. and Pharm. Bull. 24(9):2057-2077; US 2008/0004285; US 2009/0324543; US 2009/0131414; U.S. Pat. No. 6,608,053; and U.S. Pat. No. 3,939,268.

Scheme 1

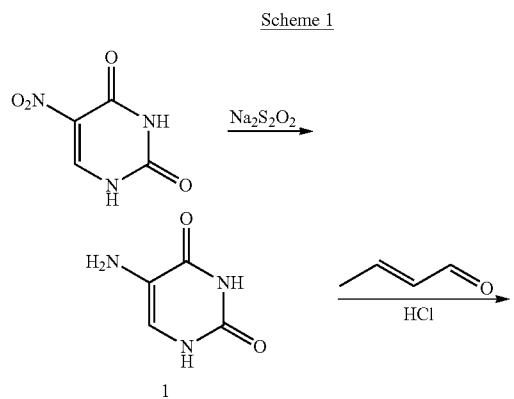

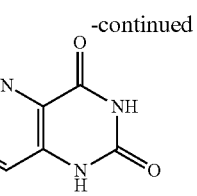

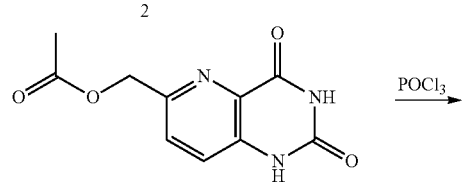

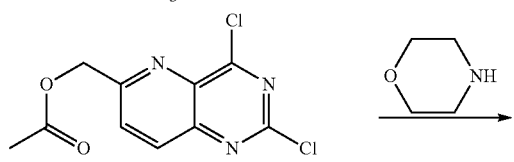

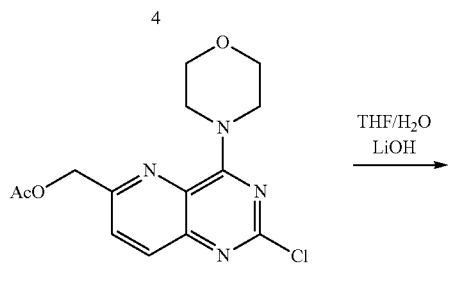

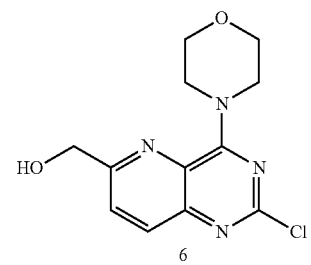

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

General Procedures and Examples provide exemplary methods for preparing Formula I compounds. Those skilled in the art will appreciate that other synthetic routes may be used to synthesize the Formula I compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

GENERAL PREPARATIVE PROCEDURES

General Procedure A

Suzuki Coupling

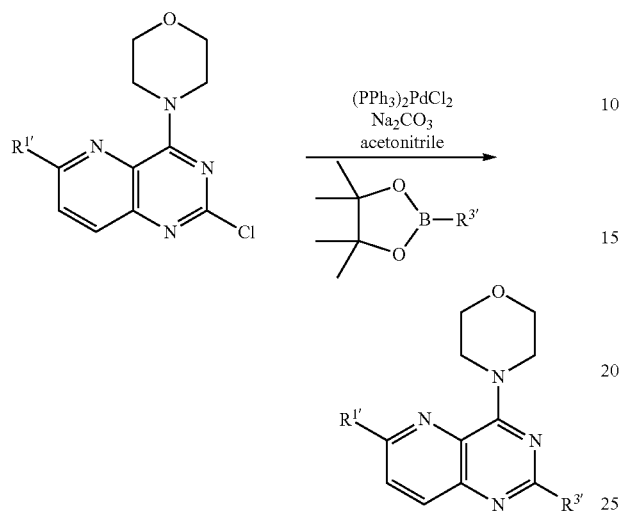

To a microwave reaction tube is charged a 4-(2-chloropyrido[3,2-d]pyrimidin-4-yl)morpholine compound (1 mmol), a $C_6$-$C_{20}$ aryl, $C_2$-$C_{20}$ heterocyclyl or $C_1$-$C_{20}$ heteroaryl boronic ester (1.3 mmol), a 2M solution of sodium carbonate in water (3 mmol), bis(triphenylphosphine)palladium(II) chloride (0.05 mmol) and acetonitrile (200 mmol). The reaction vessel is sealed and the reaction is heated in a Biotage microwave at about 140° C. for 30 minutes. The reaction mixture is loaded onto a Biotage ISOLUTE SCX-2 column. The column was first washed with MeOH. The product was eluted with a 2M solution of ammonia in methanol. After concentration, the crude product is further purified by RP-HPLC. $R^{1'}$ and $R^{3'}$ are $R^1$ and $R^3$ respectively as defined herein, or precursors or protected forms thereof.

The Suzuki-type coupling reaction is useful to attach a heterocycle or a heteroaryl at the 2-position of the pyrimidine ring of a 2-chloropyrido[3,2-d]pyrimidine compound. For example, 4-(2-chloropyrido[3,2-d]pyrimidin-4-yl)morpholine may be combined with about 1.5 equivalents of 4-(4,4,5,5-tetramethyl-1,3,2-dioxaborolan-2-yl)-1H-pyrrolo[2,3-c]pyridine, and dissolved in 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, a nitrogen of the fused bicyclic heterocycle or a fused bicyclic heteroaryl may be protected, for example as N-THP. In some cases potassium acetate was used in place of sodium carbonate to adjust the pH of the aqueous layer. The reaction is then heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the 4-(2-substituted pyrido[3,2-d]pyrimidin-4-yl)morpholine compound Suzuki coupling product may be purified on silica or by reverse phase HPLC.

A variety of palladium catalysts can be used during the Suzuki coupling step to form 4-(2-substituted pyrido[3,2-d]pyrimidin-4-yl)morpholine exemplary compounds. Low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd [P(o-tol)$_3$]$_2$, Pd$_2$(dba)$_3$/P(o-tol)$_3$, Pd$_2$(dba)/P(furyl)$_3$, Cl$_2$Pd [P(furyl)$_3$]$_2$, Cl$_2$Pd(PmePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II)EnCat™ BINAP30 (US 2004/0254066).

General Procedure B

Alkylation of 4-(6-(bromomethyl)-2-chloropyrido[3,2-d]pyrimidin-4-yl)morpholine 7

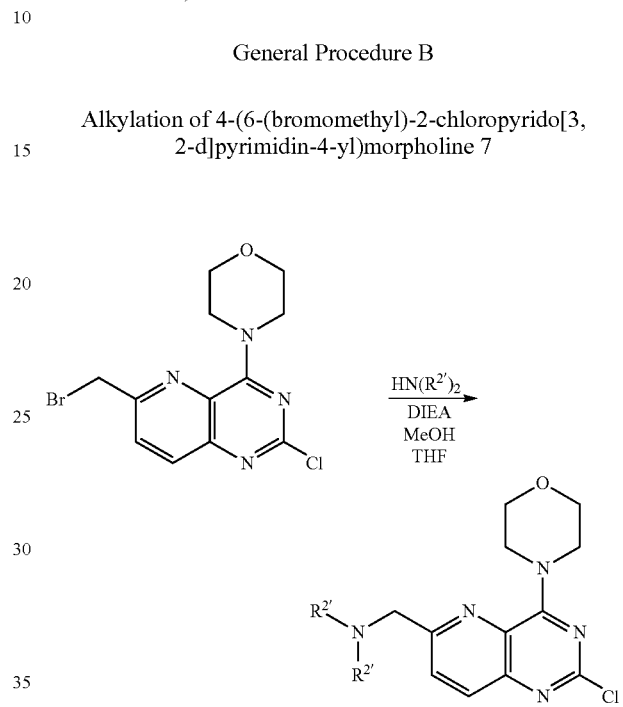

To a solution of a primary or secondary amine $HN(R^{2'})_2$ (1 equiv.) and DIEA (about 2 equiv.) in methanol and THF is added 4-(6-(bromomethyl)-2-chloropyrido[3,2-d]pyrimidin-4-yl)morpholine 7 (about 1 equiv.). The resulting solution is stirred at room temperature for about 1.5 hours. The reaction mixture is evaporated to dryness. The residue was dissolved in MeOH and loaded onto an ISOLUTE SCX-2 column. The column is first washed with MeOH. The product is then eluted with a 2M solution of ammonia in methanol. After concentration, the crude product is further purified by flash chromatography (0-10% MeOH in DCM). $R^{2'}$ is $R^2$ as defined herein, or precursors or protected forms thereof.

General Procedure C

Microwave Buchwald Coupling

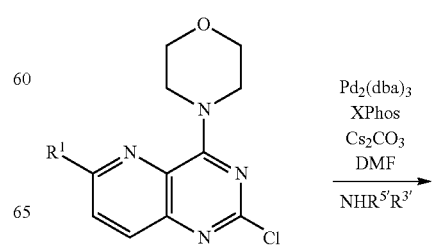

-continued

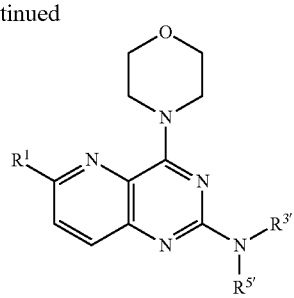

To a microwave reaction tube was charged the 4-(2-chloropyrido[3,2-d]pyrimidin-4-yl)morpholine of interest (1 mmol), the amine of interest (1.5 mmol), cesium carbonate (2 mmol), tris(dibenzylideneacetone)dipalladium (0.05 mmol), XPhos (0.1 mmol) and DMF (220 mmol). The reaction vessel was then sealed and heated in a Biotage microwave at 140° C. for 30 minutes. The reaction mixture was loaded onto a Biotage ISOLUTE SCX-2 column. The column was first washed with MeOH. The product was eluted with a 2M solution of ammonia in methanol. After concentration, the crude product was further purified by RP-HPLC. $R^{3'}$ and $R^{5'}$ are $R^3$ and $R^5$ as defined herein, or precursors or protected forms thereof.

General Procedure D

Thermal Buchwald Coupling

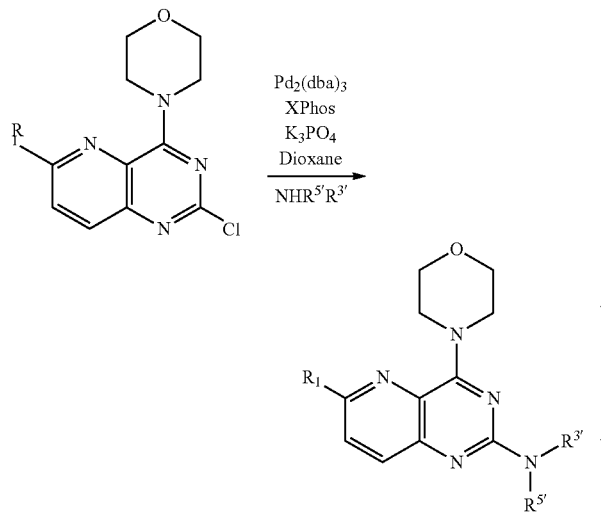

To a sealed tube was charged the 4-(2-chloropyrido[3,2-d]pyrimidin-4-yl)morpholine of interest (1 mmol), the amine of interest (1.05 mmol), potassium phosphate (2.5 mmol), tris(dibenzylideneacetone)dipalladium (0.05 mmol) and XPhos (0.1 mmol) in 1,4-Dioxane (220 mmol). The reaction heated in an oil bath at 150° C. for 2-18 hours. The reaction mixture was then loaded onto a Biotage ISOLUTE SCX-2 column. The column was first washed with MeOH. The product was eluted with a 2M solution of ammonia in methanol. After concentration, the crude product was further purified by RP-HPLC. $R^{3'}$ and $R^{5'}$ are $R^3$ and $R^5$ as defined herein, or precursors or protected forms thereof.

Scheme 1 shows a general synthetic route to pyrido[3,2-d]pyrimidine compounds via intermediate 6.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

Microwave experiments were carried out using a CEM Explorer, Smith Synthesizer or a Biotage Initiator™, which uses a single-mode resonator and dynamic field tuning, both of which give reproducibility and control. Temperatures from 40-250° C. can be achieved and pressures up to 20 bar can be reached.

Unless otherwise stated, all reactions were performed under an inert, i.e. argon or nitrogen, atmosphere.

Example 1

5-aminopyrimidine-2,4(1H,3H)-dione 1

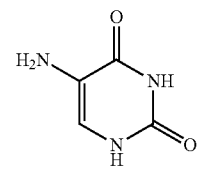

Into a 5-L 4-necked round-bottom flask were placed water (2.871 L), ammonia (116.1 mL) and 5-nitropyrimidine-2,4(1H,3H)-dione (180 g, 1.15 mol, 1.00 equiv). This was followed by the addition of $Na_2S_2O_2$ (860 g, 6.06 mol, 4.30 equiv) in several batches. The pH value of the solution was adjusted to 8 with ammonia (25%). The resulting solution was stirred for 3 h (hours) at 75° C. The reaction mixture was cooled to 15° C. with an ice/water bath. The solid was collected by filtration. This resulted in 118 g (81%) of 5-aminopyrimidine-2,4(1H,3H)-dione 1 as a yellow solid (see Scheme 1).

Example 2

6-methylpyrido[3,2-d]pyrimidine-2,4(1H,3H)-dione 2

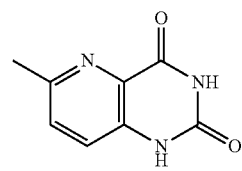

Into a 2000-mL 4-necked round-bottom flask was placed a solution of 5-aminopyrimidine-2,4(1H,3H)-dione 1 (217 g, 1.71 mol, 1.00 equiv) in HCl (20%, 1302 mL), then added (E)-but-2-enal (143.5 g, 2.05 mol, 1.20 equiv). The resulting solution was heated to reflux for 3 h (hours) in an oil bath. The reaction mixture was cooled and filtered. The filtrate was concentrated under vacuum. The residual solution was diluted with 250 mL of water and adjusted to pH 10 with ammonia (25%). The isolated solid was collected by filtration, then washed with 2×100 mL of water, 2×250 ml of ethanol and 3×500 mL of ether and finally dried in an oven. This resulted in 63 g (21%) of 6-methylpyrido[3,2-d]pyrimidine-2,4(1H,3H)-dione 2. $^1$H-NMR (400 MHz, CD$_3$OD, ppm): 7.56 (2H, s), 2.60 (3H, s)

Example 3

(2,4-dioxo-1,2,3,4-tetrahydropyrido[3,2-d]pyrimidin-6-yl)methyl acetate 3

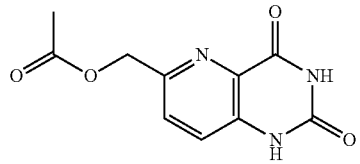

Into a 5000-mL 4-necked round-bottom flask was placed a solution of 6-methylpyrido[3,2-d]pyrimidine-2,4(1H,3H)-dione 2 (120 g, 677.97 mmol, 1.00 equiv) in acetic acid (2400 mL). This was followed by the addition of m-CBPA (608 g, 3.51 mol, 5.18 equiv) in several batches. The resulting solution was stirred overnight at 100° C. The resulting mixture was cooled and concentrated under vacuum. The residue was washed with 2×1500 mL of ether and 2×500 mL of DCM, then it was dissolved in HOAc (1200 mL) and acetic anhydride (500 mL). The resulting solution was stirred for 0.5 h at 110° C. The reaction mixture was cooled and filtered. The filtrate was concentrated under vacuum. The residue was washed with 2×500 ml of ether and dried. This resulted in 80 g (50%) of (2,4-dioxo-1,2,3,4-tetrahydropyrido[3,2-d]pyrimidin-6-yl)methyl acetate 3 as a brown solid.

Example 4

(2,4-dichloropyrido[3,2-d]pyrimidin-6-yl)methyl acetate 4

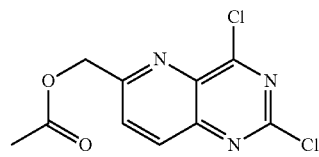

Into a 1000-mL 3-round-bottom flask was placed a solution of (2,4-dioxo-1,2,3,4-tetrahydropyrido[3,2-d]pyrimidin-6-yl)methyl acetate 3 (40 g, 161.70 mmol, 1.00 equiv, 95%) in POCl$_3$ (400 ml), then added DIEA (37.3 g, 289.15 mmol, 1.70 equiv). The resulting solution was stirred for 3 h at 108° C. in an oil bath. The resulting mixture was cooled and concentrated under vacuum. The residue was then quenched by the addition of 1000 g of ice water. The resulting solution was extracted with 4×500 mL of dichloromethane. The organic layers were combined, washed with 2×500 mL of water, dried over sodium sulfate and concentrated under vacuum. The residue was applied onto a silica gel column and eluted with ethyl acetate/petroleum ether (1:20-1:3). This resulted in 24 g (53%) of (2,4-dichloropyrido[3,2-d]pyrimidin-6-yl)methyl acetate 4 as a yellow solid. $^1$H-NMR (400 MHz, CDCl$_3$, ppm): 8.30-8.32 (1H, d, J=8.8 Hz), 7.92-7.94 (1H, d, J=8.8 Hz), 5.47 (2H, s), 2.24 (3H, s)

Example 5

(2-chloro-4-morpholinopyrido[3,2-d]pyrimidin-6-yl)methyl acetate 5

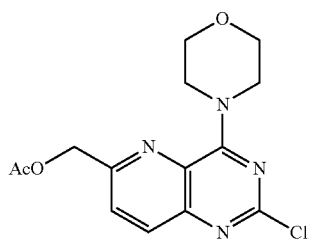

A mixture of (2,4-dichloropyrido[3,2-d]pyrimidin-6-yl)methyl acetate (1.92 g, 7.06 mmol) according to Srinivasan and Broom (1981) J. Org. Chem. 46:1777-1781, and morpholine (1.3 mL, 14.9 mmol) in ethanol (100 mL) was stirred at room temperature for 2 hours. The reaction mixture was then evaporated to dryness. The crude product was purified by flash chromatography (DCM) to give (2-chloro-4-morpholinopyrido[3,2-d]pyrimidin-6-yl)methyl acetate 5 (2.2 g, 96%). $^1$H-NMR (CDCl$_3$): δ 8.05 (d, 1H), 7.66 (d, 1H), 5.29 (s, 2H), 4.5 (s, br, 4H), 3.87 (m, 4H), 2.19 (s, 3H)

Example 6

(2-chloro-4-morpholinopyrido[3,2-d]pyrimidin-6-yl)methanol 6

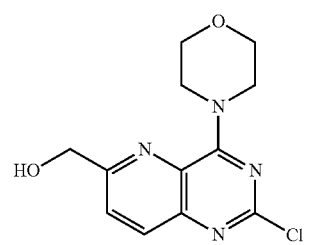

To a solution of (2-chloro-4-morpholinopyrido[3,2-d]pyrimidin-6-yl)methyl acetate 5 (2.3 g, 7.1 mmol) in THF (50 mL) was added a 1M solution of lithium hydroxide in water (26 mL). The resulting solution was stirred at room temperature for 2 hours. The reaction mixture was diluted with water and extracted three times with dichloromethane. The combined extracts were washed with brine, dried over sodium sulfate, filtered and concentrated to give (2-chloro-4-morpholinopyrido[3,2-d]pyrimidin-6-yl)methanol 6. LCMS (MH)⁺=281.1. ¹H-NMR (400 MHz, CDCl₃, ppm): 8.09 (1H, d, J=8.8 Hz), 7.66 (1H, d, J=8.8 Hz), 4.91 (2H, s), 4.56 (4H, br), 3.91 (4H, t), 2.86 (1H, s)

Example 7

4-(6-(bromomethyl)-2-chloropyrido[3,2-d]pyrimidin-4-yl)morpholine 7

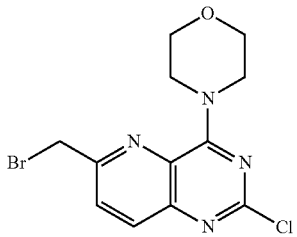

(2-Chloro-4-morpholinopyrido[3,2-d]pyrimidin-6-yl)methanol 6 (2.0 g, 0.0071 mol) and 40 mL dichloromethane were cooled to 0° C. and triphenylphosphine (2.2 g, 0.0085 mol) was added. The solution was recooled to 0° C. and N-Bromosuccinimide NBS (1.5 g, 0.0085 mol) was added in one portion. The heterogeneous mixture became homogeneous yellow upon NBS addition. After 30 mins, the progress was checked by tlc. The reaction mixture again became heterogeneous yellow mixture and was stirred overnight at room temperature. A check by LC/MS showed the reaction was complete. The reaction mixture was concentrated to dryness, taken up in MeOH, and filtered to yield 2.13 gm (87%) of 4-(6-(bromomethyl)-2-chloropyrido[3,2-d]pyrimidin-4-yl)morpholine 7 as a yellow solid. More product 7 precipitated from the mother liquor, filtered, and dried to give a second batch (133 mg) of product 7. Analyzed and confirmed by LC/MS.

Example 8

2-(1-((2-chloro-4-morpholinopyrido[3,2-d]pyrimidin-6-yl)methyl)piperidin-4-yl)propan-2-ol

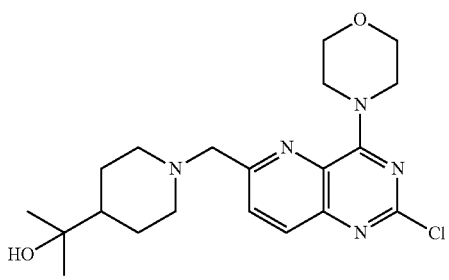 [SMILES: CC(C)(O)C1CCN(Cc2ccc3nc(Cl)nc(N4CCOCC4)c3n2)CC1]

Following General Procedure B, 4-(6-(bromomethyl)-2-chloropyrido[3,2-d]pyrimidin-4-yl)morpholine 7 and 2-(piperidin-4-yl)propan-2-ol were reacted to give 2-(1-((2-chloro-4-morpholinopyrido[3,2-d]pyrimidin-6-yl)methyl)piperidin-4-yl)propan-2-ol. LCMS (MH+)=406.1. ¹H-NMR (DMSO-d₆): δ 8.02 (d, 1H), 7.83 (d, 1H), 4.46 (s, br, 4H), 4.01 (s, 1H), 3.78 (m, 4H), 3.68 (s, 2H), 2.88 (m, 2H), 1.96 (m, 2H), 1.65 (m, 2H), 1.25 (m, 3H), 1.03 (s, 6H)

Example 101

2-(1-((2-(2-methyl-1H-benzo[d]imidazol-1-yl)-4-morpholinopyrido[3,2-d]pyrimidin-6-yl)methyl)piperidin-4-yl)propan-2-ol 101

Following General Procedure C, 2-methylbenzimidazole and 2-(1-((2-chloro-4-morpholinopyrido[3,2-d]pyrimidin-6-yl)methyl)piperidin-4-yl)propan-2-ol from Example 8 were reacted to give 101. LCMS (MH⁺)=502.3. ¹H-NMR (DMSO-d₆): δ 8.20 (m, 2H), 7.89 (m, 1H), 7.62 (m, 1H), 7.27 (m, 2H), 4.56 (s, 4H), 4.08 (s, 1H), 3.84 (m, 4H), 3.73 (s, 2H), 2.92 (m, 2H), 2.88 (s, 3H), 1.98 (m, 2H), 1.67 (m, 2H), 1.29 (m, 2H), 1.18 (m, 1H), 1.04 (s, 6H)

Example 102

2-(1-((2-(2-cyclopropyl-1H-benzo[d]imidazol-1-yl)-4-morpholinopyrido[3,2-d]pyrimidin-6-yl)methyl)piperidin-4-yl)propan-2-ol 102

Following General Procedure C, 2-cyclopropyl-benzimidazole and 2-(1-((2-chloro-4-morpholinopyrido[3,2-d]pyrimidin-6-yl)methyl)piperidin-4-yl)propan-2-ol from Example 8 were reacted to give 102. LCMS (MH⁺)=528.3. ¹H-NMR (DMSO-d₆): δ 8.19 (d, 1H), 8.03 (m, 1H), 7.89 (d, 1H), 7.44 (m, 1H), 7.23 (m, 2H), 4.56 (s, 4H), 4.01 (s, 1H), 3.83 (m, 4H), 3.74 (2, 2H), 2.94 (m, 3H), 1.99 (m, 2H), 1.67 (m, 2H), 1.29 (m, 2H), 1.16 (m, 3H), 1.08 (m, 2H), 1.04 (s, 6H)

Example 103

2-(1-((2-(2-methylbenzofuran-3-yl)-4-morpholinopyrido[3,2-d]pyrimidin-6-yl)methyl)piperidin-4-yl)propan-2-ol 103

Following General Procedure A, 4,4,5,5-tetramethyl-2-(2-methylbenzofuran-3-yl)-1,3,2-dioxaborolane and 2-(1-((2-chloro-4-morpholinopyrido[3,2-d]pyrimidin-6-yl)methyl)piperidin-4-yl)propan-2-ol from Example 8 were reacted to give 103. LCMS (MH⁺)=502.3. ¹H-NMR (DMSO-d₆): δ 8.55 (m, 1H), 8.19 (d, 1H), 7.86 (d, 1H), 7.56 (m, 1H), 7.32 (m, 2H), 4.48 (s, 4H), 4.01 (s, 1H), 3.85 (m, 4H), 3.72 (s, 2H), 2.96 (s, 3H), 2.93 (m, 2H), 2.01 (m, 2H), 1.66 (m, 2H), 1.29 (m, 2H), 1.25 (m, 1H), 1.04 (s, 6H)

Example 104

2-ethyl-1-(6-((4-(2-hydroxypropan-2-yl)piperidin-1-yl)methyl)-4-morpholinopyrido[3,2-d]pyrimidin-2-yl)-1H-indazol-3(2H)-one 104

Following General Procedure C, 2-ethyl-1H-indazol-3 (2H)-one and 2-(1-((2-chloro-4-morpholinopyrido[3,2-d]pyrimidin-6-yl)methyl)piperidin-4-yl)propan-2-ol from Example 8 were reacted to give 104. LCMS (MH⁺)=532.3. ¹H-NMR (DMSO-d₆): δ 8.39 (d, 1H), 8.09 (d, 1H), 7.82 (d, 1H), 7.78 (m, 1H), 7.70 (m, 1H), 7.33 (m, 1H), 4.54 (s, 4H), 4.32 (m, 2H), 4.00 (s, 1H), 3.85 (m, 4H), 3.68 (s, 2H), 2.90 (m, 2H), 1.97 (m, 2H), 1.64 (m, 2H), 1.29 (m, 2H), 1.16 (m, 1H), 1.07 (t, 3H), 1.03 (s, 6H)

Example 105

2-(1-((2-(5-fluoro-1H-indol-4-yl)-4-morpholinopyrido[3,2-d]pyrimidin-6-yl)methyl)piperidin-4-yl)propan-2-ol 105

Following General Procedure A, 1-(tert-butyldimethylsilyl)-5-fluoro-4-(4,4,5,5-tetramethyl-1,3,2-dioxaborolan-2-yl)-1H-indole and 2-(1-((2-chloro-4-morpholinopyrido[3,2-d]pyrimidin-6-yl)methyl)piperidin-4-yl)propan-2-ol from Example 8 were reacted to give 105. LCMS (MH$^+$)=505.2. $^1$H-NMR (DMSO-d$_6$): δ 11.2 (s, 1H), 8.15 (d, 1H), 7.87 (d, 1H), 7.47 (m, 1H), 7.44 (s, 1H), 7.01 (m, 1H), 6.75 (s, 1H), 4.49 (s, 4H), 4.02 (s, 1H), 3.80 (m, 4H), 3.73 (s, 2H), 2.93 (m, 2H), 1.99 (m, 2H), 1.66 (m, 2H), 1.28 (m, 3H), 1.04 (s, 6H)

Example 106

2-(1-((2-(5-methyl-1H-pyrazol-3-ylamino)-4-morpholinopyrido[3,2-d]pyrimidin-6-yl)methyl)piperidin-4-yl)propan-2-ol 106

Following General Procedure C, 5-methyl-1H-pyrazol-3-amine and 2-(1-((2-chloro-4-morpholinopyrido[3,2-d]pyrimidin-6-yl)methyl)piperidin-4-yl)propan-2-ol from Example 8 were reacted to give 106. LCMS (MH$^+$)=467.3. $^1$H-NMR (DMSO-d$_6$): δ 11.8 (s, 1H), 8.91 (s, 1H), 7.78 (s, 1H), 7.62 (d, 1H), 6.48 (s, 1H), 4.39 (s, 4H), 3.99 (s, 1H), 3.76 (m, 4H), 3.59 (s, 2H), 2.90, (m, 2H), 2.19 (s, 3H), 1.93 (m, 2H), 1.63 (m, 2H), 1.24 (m, 2H), 1.16 (m, 1H), 1.03 (s, 6H)

Example 107

2-(1-((2-(2-aminopyrimidin-5-yl)-4-morpholinopyrido[3,2-d]pyrimidin-6-yl)methyl)piperidin-4-yl)propan-2-ol 107

Following General Procedure A, 5-(4,4,5,5-tetramethyl-1,3,2-dioxaborolan-2-yl)pyrimidin-2-amine and 2-(1-((2-chloro-4-morpholinopyrido[3,2-d]pyrimidin-6-yl)methyl)piperidin-4-yl)propan-2-ol from Example 8 were reacted to give 107. LCMS (MH$^+$)=465.3. $^1$H-NMR (DMSO-d$_6$): δ 8.29 (s, 1H), 8.09 (d, 1H), 7.80 (d, 1H), 7.09 (s, 2H), 4.50 (s, 4H), 4.01 (s, 1H), 3.81 (m, 4H), 3.68 (s, 2H), 2.91 (m, 2H), 1.97 (m, 2H), 1.65 (m, 2H), 1.29 (m, 2H), 1.17 (m, 1H), 1.03 (s, 6H)

Example 108

(2-(5-fluoro-1H-indol-4-yl)-4-morpholinopyrido[3,2-d]pyrimidin-6-yl)methanol 108

(2-Chloro-4-morpholinopyrido[3,2-d]pyrimidin-6-yl)methanol 6 (0.1 g) was reacted with 1-(tert-butyldimethylsilyl)-5-fluoro-4-(4,4,5,5-tetramethyl-1,3,2-dioxaborolan-2-yl)-1H-indole via General Procedure A to produce 73.4 mg of 108 following reverse phase HPLC purification. MS (Q1) 380.1 (M)+

Example 109

2-(1-((2-(1H-indol-4-yl)-4-morpholinopyrido[3,2-d]pyrimidin-6-yl)methyl)piperidin-4-yl)propan-2-ol 109

2-(1-((2-chloro-4-morpholinopyrido[3,2-d]pyrimidin-6-yl)methyl)piperidin-4-yl)propan-2-ol from Example 8 (88 mg) was reacted with 1H-indol-4-ylboronic acid via General Procedure A to produce 22.8 mg of 109 following reverse phase HPLC purification. MS (Q1) 487.3 (M)+

Example 110

2-(1-((2-(1H-indazol-4-yl)-4-morpholinopyrido[3,2-d]pyrimidin-6-yl)methyl)piperidin-4-yl)propan-2-ol 110

2-(1-((2-chloro-4-morpholinopyrido[3,2-d]pyrimidin-6-yl)methyl)piperidin-4-yl)propan-2-ol from Example 8 (88 mg) was reacted with 4-(4,4,5,5-tetramethyl-1,3,2-dioxaborolan-2-yl)-1H-indazole via General Procedure A to produce 29.6 mg of 110 following reverse phase hplc purification. MS (Q1) 488.3 (M)+

Example 111

4-(2-(5-fluoro-1H-indol-4-yl)-6-((3-(tetrahydro-2H-pyran-4-yl)azetidin-1-yl)methyl)pyrido[3,2-d]pyrimidin-4-yl)morpholine 111

Step 1: 4-(2-chloro-6-((3-(tetrahydro-2H-pyran-4-yl)azetidin-1-yl)methyl)pyrido[3,2-d]pyrimidin-4-yl)morpholine

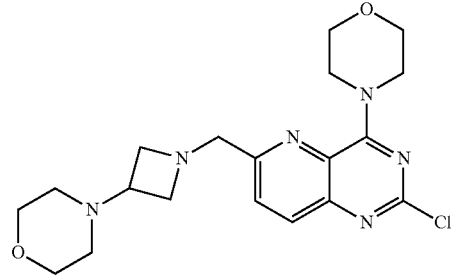 [SMILES: Clc1nc(N2CCOCC2)c2nc(CN3CC(N4CCOCC4)C3)ccc2n1]

4-(6-(Bromomethyl)-2-chloropyrido[3,2-d]pyrimidin-4-yl)morpholine 7 (0.34 g) was reacted with 3-(tetrahydro-2H-pyran-4-yl)azetidine via General Procedure B to produce crude 4-(2-chloro-6-((3-(tetrahydro-2H-pyran-4-yl)azetidin-1-yl)methyl)pyrido[3,2-d]pyrimidin-4-yl)morpholine Step 2: Crude 4-(2-chloro-6-((3-(tetrahydro-2H-pyran-4-yl)azetidin-1-yl)methyl)pyrido[3,2-d]pyrimidin-4-yl)morpholine (0.1 g) was reacted with 1-(tert-butyldimethylsilyl)-5-fluoro-4-(4,4,5,5-tetramethyl-1,3,2-dioxaborolan-2-yl)-1H-indole via General Procedure A to produce 49 mg of 111 following reverse phase HPLC purification.
MS (Q1) 503.3 (M)+

Example 112

2-(1-((2-(2-isopropyl-1H-benzo[d]imidazol-1-yl)-4-morpholinopyrido[3,2-d]pyrimidin-6-yl)methyl)piperidin-4-yl)propan-2-ol 112

2-(1-((2-Chloro-4-morpholinopyrido[3,2-d]pyrimidin-6-yl)methyl)piperidin-4-yl)propan-2-ol from Example 8 (0.73 g) was reacted with 2-isopropyl-1H-benzo[d]imidazole and sodium tert-butoxide (instead of cesium carbonate) via General Procedure C to produce 0.192 g of 112 following reverse phase HPLC purification. MS (Q1) 530.3 (M)+

Example 113

4-(2-(2-isopropyl-1H-benzo[d]imidazol-1-yl)-6-((3-(tetrahydro-2H-pyran-4-yl)azetidin-1-yl)methyl)pyrido[3,2-d]pyrimidin-4-yl)morpholine 113

4-(2-chloro-6-((3-(tetrahydro-2H-pyran-4-yl)azetidin-1-yl)methyl)pyrido[3,2-d]pyrimidin-4-yl)morpholine from Example 111 (0.1 g) was reacted with 2-isopropyl-1H-benzo[d]imidazole via General Procedure C to produce 10.2 mg of 113 following reverse phase HPLC purification. MS (Q1) 528.3 (M)+

Example 116

2-(1-((2-(6-amino-2-methylpyridin-3-yl)-4-morpholinopyrido[3,2-d]pyrimidin-6-yl)methyl)piperidin-4-yl)propan-2-ol 116

Step 1: 6-methyl-5-(4,4,5,5-tetramethyl-1,3,2-dioxaborolan-2-yl)pyridin-2-amine

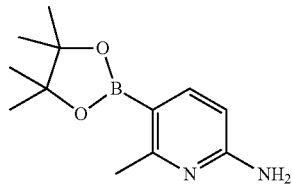 [SMILES: Cc1nc(N)ccc1B1OC(C)(C)C(C)(C)O1]

To 5-bromo-6-methylpyridin-2-amine (0.75 g), bispinacol ester boronate (1.2 eq), potassium acetate (3 eq), Palladium Acetate (0.05 eq) and S-Phos (0.1 eq) in a microwave vial were added Acetonitrile (8 mL) and Water (8 mL). The reaction was heated into a Biotage microwave at 140° C. for 30 minutes. The mixture was diluted with ethyl acetate and washed with twice with brine. The aqueous layer was back-extracted twice with ethyl acetate. The combined organic layers were dried over magnesium sulfate, filtered and concentrated to yield the crude 6-methyl-5-(4,4,5,5-tetramethyl-1,3,2-dioxaborolan-2-yl)pyridin-2-amine Step 2: 2-(1-((2-Chloro-4-morpholinopyrido[3,2-d]pyrimidin-6-yl)methyl)piperidin-4-yl)propan-2-ol from Example 8 (70 mg) was reacted with 6-methyl-5-(4,4,5,5-tetramethyl-1,3,2-dioxaborolan-2-yl)pyridin-2-amine via General Procedure A to produce 32.1 mg of 116 following reverse phase HPLC purification. MS (Q1) 478.3 (M)+

Example 117 methyl 2-(3-((2-(2-isopropyl-1H-benzo[d]imidazol-1-yl)-4-morpholinopyrido[3,2-d]pyrimidin-6-yl)methyl)azetidin-1-yl)-2-methylpropanoate 117

Step 1: dimethyl (2-chloro-4-morpholinopyrido[3,2-d]pyrimidin-6-yl)methylphosphonate

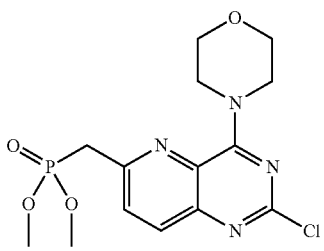 [SMILES: COP(=O)(Cc1ccc2nc(Cl)nc(N3CCOCC3)c2n1)OC]

To 4-(6-(bromomethyl)-2-chloropyrido[3,2-d]pyrimidin-4-yl)morpholine 7 (2 g) was added Trimethyl Phosphite (30 eq) and the reaction was refluxed at 120° C. for 90 minutes. The reaction was cooled and concentrated to dryness under vacuum. To the dried crude was added water, upon which a yellow solid crashed out and was filtered and dried overnight under vacuum to afford 2 g of pure dimethyl (2-chloro-4-morpholinopyrido[3,2-d]pyrimidin-6-yl)methylphosphonate.

Step 2: tert-butyl 3-((2-chloro-4-morpholinopyrido[3,2-d]pyrimidin-6-yl)methylene)azetidine-1-carboxylate

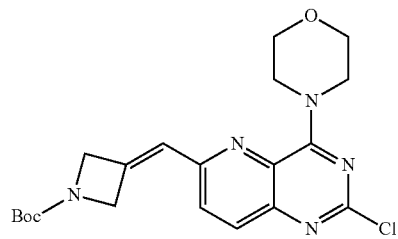 [SMILES: CC(C)(C)OC(=O)N1CC(=Cc2ccc3nc(Cl)nc(N4CCOCC4)c3n2)C1]

To a suspension of dimethyl (2-chloro-4-morpholinopyrido[3,2-d]pyrimidin-6-yl)methylphosphonate (0.32 g) in anhydrous THF (3 mL) at 0° C. was added 2.0 M of lithium diisopropylamide in tetrahydrofuran (1.4 eq). The resulting solution was allowed to warm to RT (room temperature) before adding a solution of tert-butyl 3-oxoazetidine-1-carboxylate (1.4 eq) in anhydrous THF (3 mL). The reaction mixture was stirred at room temperature for 1 h, then partitioned between brine and DCM. The organic layer was isolated, dried (MgSO4) and concentrated in vacuo to give 0.34 g of crude tert-butyl 3-((2-chloro-4-morpholinopyrido[3,2-d]pyrimidin-6-yl)methylene)azetidine-1-carboxylate.

Step 3: tert-butyl 3-((2-(2-isopropyl-1H-benzo[d]imidazol-1-yl)-4-morpholinopyrido[3,2-d]pyrimidin-6-yl)methylene)azetidine-1-carboxylate

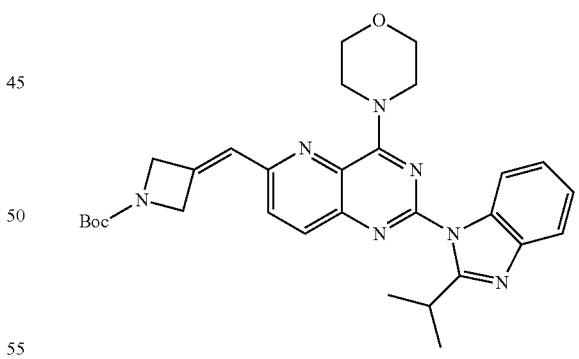

To a microwave vial was added tert-butyl 3-((2-chloro-4-morpholinopyrido[3,2-d]pyrimidin-6-yl)methylene)azetidine-1-carboxylate, 2-isopropyl-1H-benzo[d]imidazole (1.05 eq), sodium tert-butoxide (2 eq), Palladium Acetate (0.1 eq) and Bis(tri-t-butylphosphine)palladium (0.1 eq). The tube was flushed with nitrogen for 10 minutes before adding Toluene (8 mL). The reaction was microwaved at 145° C. for 20 minutes. The crude was purified by flash column chromatography to afford 0.22 g of tert-butyl 3-((2-(2-isopropyl-1H-benzo[d]imidazol-1-yl)-4-morpholinopyrido[3,2-d]pyrimidin-6-yl)methylene)azetidine-1-carboxylate.

Step 4: tert-butyl 3-((2-(2-isopropyl-1H-benzo[d]imidazol-1-yl)-4-morpholinopyrido[3,2-d]pyrimidin-6-yl)methyl)azetidine-1-carboxylate

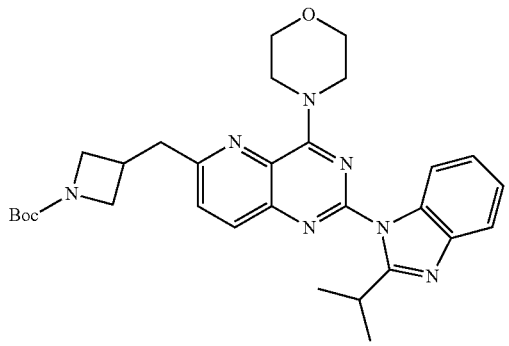 [SMILES: CC(C)c1nc2ccccc2n1-c1nc(N2CCOCC2)c2nc(CC3CN(C(=O)OC(C)(C)C)C3)ccc2n1]

tert-butyl 3-((2-(2-isopropyl-1H-benzo[d]imidazol-1-yl)-4-morpholinopyrido[3,2-d]pyrimidin-6-yl)methylene)azetidine-1-carboxylate (0.2 g) was brought up in MeOH (20 mL) and the flask was purged with nitrogen before addition of 10% Palladium on Carbon (20 mol %). The reaction was heated at 60° C. for 6 hours, cooled and filtered thru celite to obtain the crude tert-butyl 3-((2-(2-isopropyl-1H-benzo[d]imidazol-1-yl)-4-morpholinopyrido[3,2-d]pyrimidin-6-yl)methyl)azetidine-1-carboxylate following solvent evaporation.

Step 5: tert-Butyl 3-((2-(2-isopropyl-1H-benzo[d]imidazol-1-yl)-4-morpholinopyrido[3,2-d]pyrimidin-6-yl)methyl)azetidine-1-carboxylate (0.2 g) was deprotected with 4N HCl in dioxane (0.9 mL) at room temperature over 1 hour. The reaction was concentrated to dryness to afford crude 4-(6-(azetidin-3-ylmethyl)-2-(2-isopropyl-1H-benzo[d]imidazol-1-yl)pyrido[3,2-d]pyrimidin-4-yl)morpholine which was reacted with methyl 2-bromo-2-methylpropanoate (3 eq) and potassium carbonate (6 eq) at 75° C. for 3 hours. The reaction mixture loaded onto a Biotage isolute cartridge, eluted with 2M NH$_3$ in MeOH then purified by reverse phase HPLC to yield 17.9 mg of 117. MS (Q1) 544.3 (M)+

Example 118

(2-(5-fluoro-1H-indol-4-yl)-4-morpholinopyrido[3,2-d]pyrimidin-6-yl)(4-(2-hydroxypropan-2-yl)piperidin-1-yl)methanone 118

Step 1: 2-chloro-4-morpholinopyrido[3,2-d]pyrimidine-6-carbaldehyde

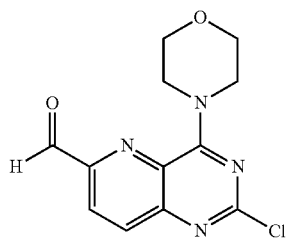 [SMILES: O=Cc1ccc2nc(Cl)nc(N3CCOCC3)c2n1]

(2-chloro-4-morpholinopyrido[3,2-d]pyrimidin-6-yl)methanol 6 (1 g) was reacted with pyridinium chlorochromate (1.1 eq) overnight at room temperature in dichloromethane (25 mL). The reaction was filtered thru celite and run thru a silica plug to get 0.69 g of 2-chloro-4-morpholinopyrido[3,2-d]pyrimidine-6-carbaldehyde as a yellow solid after evaporation.

Step 2: 2-chloro-4-morpholinopyrido[3,2-d]pyrimidine-6-carboxylic acid

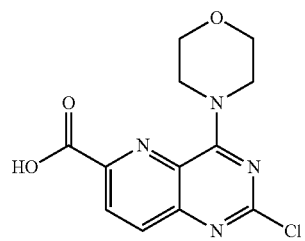 [SMILES: O=C(O)c1ccc2nc(Cl)nc(N3CCOCC3)c2n1]

2-Chloro-4-morpholinopyrido[3,2-d]pyrimidine-6-carbaldehyde (0.56 g) was reacted with Oxone (1.1 eq) in DMF (10 mL) overnight. The DMF was removed under vacuum and the reaction mixture was brought up into water. The pH was adjusted to 2-3 and product crashed out of solution. The solid was collected by filtration and dried to afford 0.45 g of 2-chloro-4-morpholinopyrido[3,2-d]pyrimidine-6-carboxylic acid as a light yellow solid.

Step 3: (2-chloro-4-morpholinopyrido[3,2-d]pyrimidin-6-yl)(4-(2-hydroxypropan-2-yl)piperidin-1-yl)methanone

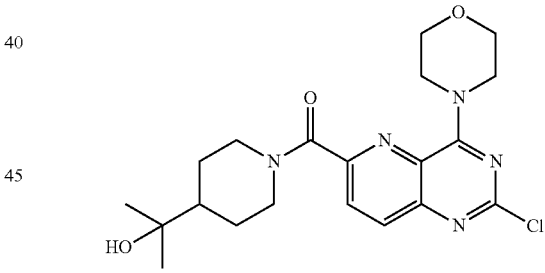

2-Chloro-4-morpholinopyrido[3,2-d]pyrimidine-6-carboxylic acid (0.12 g) was reacted with 2-(piperidin-4-yl)propan-2-ol (1.2 eq), HATU O-(7-azabenzotriazol-1-yl)-N,N,N',N'-tetramethyluronium hexafluorophosphate (1.2 eq) and DIPEA (3 eq) in DMF (3.2 mL) for 1 hour. The reaction was then extracted with EtOAc and bicarbonate solution and the organic layer was dried with Magnesium sulfate, filtered and concentrated to give (2-chloro-4-morpholinopyrido[3,2-d]pyrimidin-6-yl)(4-(2-hydroxypropan-2-yl)piperidin-1-yl)methanone in quantitative yield.

Step 4: (2-chloro-4-morpholinopyrido[3,2-d]pyrimidin-6-yl)(4-(2-hydroxypropan-2-yl)piperidin-1-yl)methanone (88 mg) was reacted with 1-(tert-butyldimethylsilyl)-5-fluoro-4-(4,4,5,5-tetramethyl-1,3,2-dioxaborolan-2-yl)-1H-indole via General Procedure A to yield 41.5 mg 118 following reverse phase HPLC purification. MS (Q1) 519.2 (M)+

Example 119

(4-(2-hydroxypropan-2-yl)piperidin-1-yl)(2-(2-isopropyl-1H-benzo[d]imidazol-1-yl)-4-morpholinopyrido[3,2-d]pyrimidin-6-yl)methanone 119

(2-Chloro-4-morpholinopyrido[3,2-d]pyrimidin-6-yl)(4-(2-hydroxypropan-2-yl)piperidin-1-yl)methanone from Example 118 (80 mg) was reacted with 2-isopropyl-1H-benzo[d]imidazole (1.05 eq), sodium tert-butoxide (2 eq), palladium acetate (0.1 eq) and bis(tri-t-butylphosphine)palladium (0.1 eq). The tube was flushed with nitrogen for 10 minutes before adding Toluene (2 mL). The reaction was microwaved at 145° C. for 20 minutes. The crude was loaded onto a Biotage isolute scx-2 cartridge, eluted with 2M ammonia in MeOH then purified by flash column chromatography to afford 6.6 mg of 119. MS (Q1) 544.3 (M)+

Example 120

2-(1-((2-(2-(1,1-difluoroethyl)-1H-benzo[d]imidazol-1-yl)-4-morpholinopyrido[3,2-d]pyrimidin-6-yl)methyl)piperidin-4-yl)propan-2-ol 120

Step 1: 2-(1-((2-(2-aminophenylamino)-4-morpholinopyrido[3,2-d]pyrimidin-6-yl)methyl)piperidin-4-yl)propan-2-ol

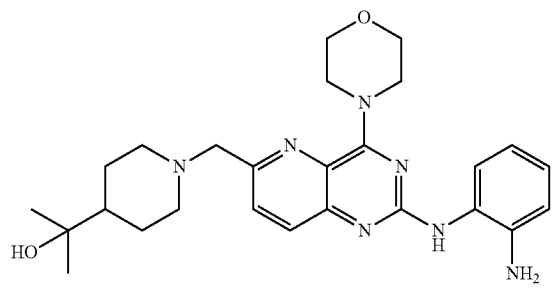 [SMILES: CC(C)(O)C1CCN(Cc2ccc3nc(Nc4ccccc4N)nc(N4CCOCC4)c3n2)CC1]

2-(1-((2-chloro-4-morpholinopyrido[3,2-d]pyrimidin-6-yl)methyl)piperidin-4-yl)propan-2-ol from Example 8 (0.12 g) was reacted with diaminobenzene via General Procedure C to afford crude 2-(1-((2-(2-aminophenylamino)-4-morpholinopyrido[3,2-d]pyrimidin-6-yl)methyl)piperidin-4-yl)propan-2-ol after elution thru a Biotage isolute scx-2 cartridge.

Step 2: 2,2-difluoro-N-(2-(6-((4-(2-hydroxypropan-2-yl)piperidin-1-yl)methyl)-4-morpholinopyrido[3,2-d]pyrimidin-2-ylamino)phenyl)propanamide

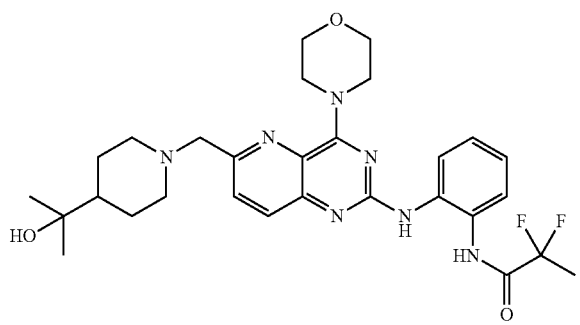 [SMILES: CC(F)(F)C(=O)Nc1ccccc1Nc1nc(N2CCOCC2)c2nc(CN3CCC(C(C)(C)O)CC3)ccc2n1]

2-(1-((2-(2-aminophenylamino)-4-morpholinopyrido[3,2-d]pyrimidin-6-yl)methyl)piperidin-4-yl)propan-2-ol was reacted with 2,2-difluoropropanoic acid (2 eq), O-(7-azabenzotriazol-1-yl)-N,N,N',N'-tetramethyluronium hexafluorophosphate (HATU, 1.5 eq) and DIPEA (4 eq) in DMF (4 mL) for 1 hr (hour). The reaction mixture was extracted with EtOAc and bicarbonate solution and the organic layer was dried with Magnesium sulfate, filtered, evaporated and purified via flash column chromatography to get 50 mg of 2,2-difluoro-N-(2-(6-((4-(2-hydroxypropan-2-yl)piperidin-1-yl)methyl)-4-morpholinopyrido[3,2-d]pyrimidin-2-ylamino)phenyl)propanamide. This intermediate was reacted with acetic acid (1.6 mL) over one week to yield 4.1 mg of 120 following reverse phase HPLC purification. MS (Q1) 552.3 (M)+

Example 121

2-(4-((2-(5-fluoro-1H-indol-4-yl)-4-morpholinopyrido[3,2-d]pyrimidin-6-yl)methyl)piperazin-1-yl)-2-methylpropanamide 121

Step 1: 2-(4-((2-chloro-4-morpholinopyrido[3,2-d]pyrimidin-6-yl)methyl)piperazin-1-yl)-2-methylpropanamide

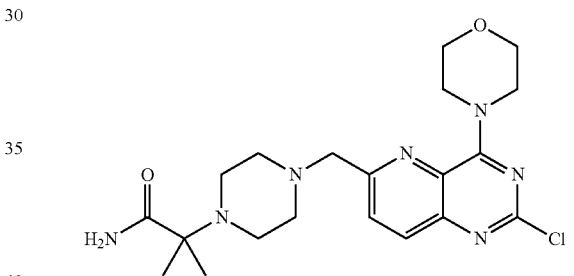

4-(6-(Bromomethyl)-2-chloropyrido[3,2-d]pyrimidin-4-yl)morpholine 7 (0.1 g) was reacted with 2-methyl-2-(piperazin-1-yl)propanamide via General Procedure B to give 123 mg of 2-(4-((2-chloro-4-morpholinopyrido[3,2-d]pyrimidin-6-yl)methyl)piperazin-1-yl)-2-methylpropanamide.

Step 2: 2-(4-((2-Chloro-4-morpholinopyrido[3,2-d]pyrimidin-6-yl)methyl)piperazin-1-yl)-2-methylpropanamide (123 mg) was reacted with 1-(tert-butyldimethylsilyl)-5-fluoro-4-(4,4,5,5-tetramethyl-1,3,2-dioxaborolan-2-yl)-1H-indole via General Procedure A to produce 114 mg of 121 following reverse phase HPLC purification. MS (Q1) 533.3 (M)+

Example 122

2-(1-((2-(6-aminopyridin-3-yl)-4-morpholinopyrido[3,2-d]pyrimidin-6-yl)methyl)piperidin-4-yl)propan-2-ol 122

2-(1-((2-Chloro-4-morpholinopyrido[3,2-d]pyrimidin-6-yl)methyl)piperidin-4-yl)propan-2-ol from Example 8 (0.1 g) was reacted with 2-aminopyridine-5-boronic acid, pinacol ester via General Procedure A to yield 40.3 mg 122 following reverse phase HPLC purification. MS (Q1) 464.3 (M)+

Example 123

2-(4-((2-(1H-indol-3-yl)-4-morpholinopyrido[3,2-d]pyrimidin-6-yl)methyl)piperazin-1-yl)-2-methylpropanamide 123

2-(4-((2-Chloro-4-morpholinopyrido[3,2-d]pyrimidin-6-yl)methyl)piperazin-1-yl)-2-methylpropanamide from Example 121 (115 mg) was reacted with 1-(phenylsulfonyl)-3-indoleboronic acid via General Procedure A to yield 31.8 mg 123 following phenylsulfonyl group deprotection with aqueous potassium hydroxide at 50° C. for 2 hours then reverse phase HPLC purification. MS (Q1) 515.3 (M)+

Example 124

2-(4-((2-(6-aminopyridin-3-yl)-4-morpholinopyrido[3,2-d]pyrimidin-6-yl)methyl)piperazin-1-yl)-2-methylpropanamide 124

2-(4-((2-Chloro-4-morpholinopyrido[3,2-d]pyrimidin-6-yl)methyl)piperazin-1-yl)-2-methylpropanamide from Example 121 (115 mg) was reacted with 2-aminopyridine-5-boronic acid, pinacol ester via General Procedure A to yield 8.5 mg 124 following reverse phase HPLC purification. MS (Q1) 492.3 (M)+

Example 125

4-(6-((3-(4,4-difluoropiperidin-1-yl)azetidin-1-yl)methyl)-2-(5-fluoro-1H-indol-4-yl)pyrido[3,2-d]pyrimidin-4-yl)morpholine 125

Step 1: 4-(2-chloro-6-((3-(4,4-difluoropiperidin-1-yl)azetidin-1-yl)methyl)pyrido[3,2-d]pyrimidin-4-yl)morpholine

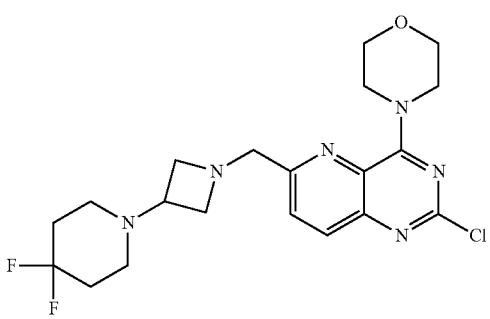 [SMILES: FC1(F)CCN(C2CN(Cc3ccc4nc(Cl)nc(N5CCOCC5)c4n3)C2)CC1]

4-(6-(Bromomethyl)-2-chloropyrido[3,2-d]pyrimidin-4-yl)morpholine 7 (0.1 g) was reacted with 1-(azetidin-3-yl)-4,4-difluoropiperidine via General Procedure B to give 80 mg 4-(2-chloro-6-((3-(4,4-difluoropiperidin-1-yl)azetidin-1-yl)methyl)pyrido[3,2-d]pyrimidin-4-yl)morpholine.

Step 2: 4-(2-chloro-6-((3-(4,4-difluoropiperidin-1-yl)azetidin-1-yl)methyl)pyrido[3,2-d]pyrimidin-4-yl)morpholine was reacted with 1-(tert-butyldimethylsilyl)-5-fluoro-4-(4,4,5,5-tetramethyl-1,3,2-dioxaborolan-2-yl)-1H-indole via General Procedure A to produce 24.7 mg of 125 following reverse phase HPLC purification. MS (Q1) 538.3 (M)+

Example 126

4-(1-((2-(5-fluoro-1H-indol-4-yl)-4-morpholinopyrido[3,2-d]pyrimidin-6-yl)methyl)azetidin-3-yl)morpholine 126

Step 1: 4-(1-((2-chloro-4-morpholinopyrido[3,2-d]pyrimidin-6-yl)methyl)azetidin-3-yl)morpholine

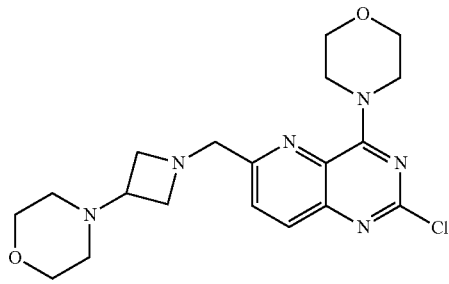 [SMILES: Clc1nc(N2CCOCC2)c2nc(CN3CC(N4CCOCC4)C3)ccc2n1]

tert-butyl 3-morpholinoazetidine-1-carboxylate (31 mg) was treated with 4N HCl in dioxane (5 eq) in 1 mL of DCM. The reaction mixture was stirred for 3 hours at room temperature and then concentrated to dryness to yield 4-(azetidin-3-yl)morpholine in quantitative yield. 4-(6-(Bromomethyl)-2-chloropyrido[3,2-d]pyrimidin-4-yl)morpholine 7 (0.413 g) was reacted with 4-(azetidin-3-yl)morpholine via General Procedure B to afford 0.4 g 4-(1-((2-chloro-4-morpholinopyrido[3,2-d]pyrimidin-6-yl)methyl)azetidin-3-yl)morpholine Step 2: 4-(1-((2-chloro-4-morpholinopyrido[3,2-d]pyrimidin-6-yl)methyl)azetidin-3-yl)morpholine (119 mg) was reacted with 1-(tert-butyldimethylsilyl)-5-fluoro-4-(4,4,5,5-tetramethyl-1,3,2-dioxaborolan-2-yl)-1H-indole via General Procedure A to produce 46 mg of 126 following reverse phase HPLC purification. MS (Q1) 504.2 (M)+

Example 127

4-(1-((2-(5-fluoro-1H-indol-4-yl)-4-morpholinopyrido[3,2-d]pyrimidin-6-yl)methyl)azetidin-3-yl)piperazin-2-one 127

Step 1: 4-(1-((2-chloro-4-morpholinopyrido[3,2-d]pyrimidin-6-yl)methyl)azetidin-3-yl)piperazin-2-one

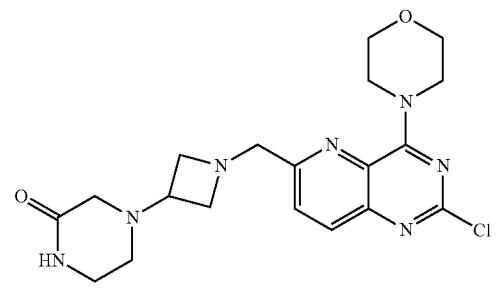 [SMILES: O=C1CN(C2CN(Cc3ccc4nc(Cl)nc(N5CCOCC5)c4n3)C2)CCN1]

4-(6-(bromomethyl)-2-chloropyrido[3,2-d]pyrimidin-4-yl)morpholine 7 (0.201 g) was reacted with 4-(azetidin-3-yl)

piperazin-2-one via General Procedure B to afford 0.18 g 4-(1-((2-chloro-4-morpholinopyrido[3,2-d]pyrimidin-6-yl)methyl)azetidin-3-yl)piperazin-2-one.

Step 2: 4-(1-((2-chloro-4-morpholinopyrido[3,2-d]pyrimidin-6-yl)methyl)azetidin-3-yl)piperazin-2-one (87 mg) was reacted with 1-(tert-butyldimethylsilyl)-5-fluoro-4-(4,4,5,5-tetramethyl-1,3,2-dioxaborolan-2-yl)-1H-indole via General Procedure A to produce 46.1 mg of 127 following reverse phase HPLC purification. MS (Q1) 517.3 (M)+

Example 128

2-(1-((2-(1H-indol-1-yl)-4-morpholinopyrido[3,2-d]pyrimidin-6-yl)methyl)piperidin-4-yl)propan-2-ol 128

Sodium Hydride (60% oil dispersion, 1.5 eq) was added to a solution of indole (1.05 eq) in DMF at 0° C. and stirred until gas evolution was complete. After 30 minutes, the solution was warmed to room temperature and 2-(1-((2-chloro-4-morpholinopyrido[3,2-d]pyrimidin-6-yl)methyl)piperidin-4-yl)propan-2-ol from Example 8 (0.15 g) was added. The reaction mixture was microwaved for 15 minutes at 175° C. and run thru a Biotage isolate scx-2 cartridge. The crude was purified by reverse phase HPLC to afford 8.7 mg of 128. MS (Q1) 487.3 (M)+

Example 129

4-(2-(5-fluoro-1H-indol-4-yl)-6-((3-(1,1-dioxo)thiomorpholinoazetidin-1-yl)methyl)pyrido[3,2-d]pyrimidin-4-yl)morpholine 129

Step 1: 4-(2-chloro-6-((3-(1,1-dioxo)thiomorpholinoazetidin-1-yl)methyl)pyrido[3,2-d]pyrimidin-4-yl)morpholine

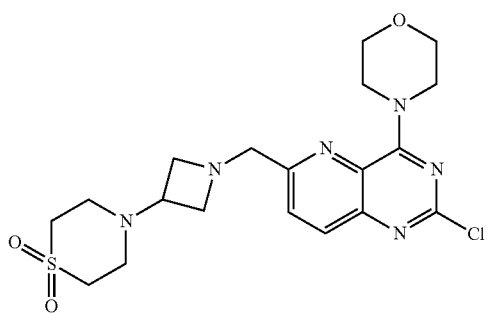 [SMILES: O=S1(=O)CCN(C2CN(Cc3ccc4nc(Cl)nc(N5CCOCC5)c4n3)C2)CC1]

4-(6-(Bromomethyl)-2-chloropyrido[3,2-d]pyrimidin-4-yl)morpholine 7 (0.256 g) was reacted with 4-(azetidin-3-yl)1,1-dioxothiomorpholine via General Procedure B to afford 0.12 g 4-(2-chloro-6-((3-(1,1-dioxo)thiomorpholinoazetidin-1-yl)methyl)pyrido[3,2-d]pyrimidin-4-yl)morpholine.

Step 2: 4-(2-chloro-6-((3-(1,1-dioxo)thiomorpholinoazetidin-1-yl)methyl)pyrido[3,2-d]pyrimidin-4-yl)morpholine (0.13 g) was reacted with 1-(tert-butyldimethylsilyl)-5-fluoro-4-(4,4,5,5-tetramethyl-1,3,2-dioxaborolan-2-yl)-1H-indole via General Procedure A to produce 47.4 mg of 129 following reverse phase HPLC purification. MS (Q1) 552.2 (M)+

Example 130

4-(2-(5-fluoro-1H-indol-4-yl)-6-((4-(oxetan-3-yl)piperidin-1-yl)methyl)pyrido[3,2-d]pyrimidin-4-yl)morpholine 130

Step 1: 4-(2-chloro-6-((4-(oxetan-3-yl)piperidin-1-yl)methyl)pyrido[3,2-d]pyrimidin-4-yl)morpholine

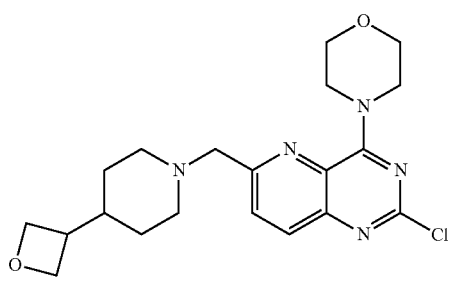 [SMILES: Clc1nc(N2CCOCC2)c2nc(CN3CCC(C4COC4)CC3)ccc2n1]

4-(6-(Bromomethyl)-2-chloropyrido[3,2-d]pyrimidin-4-yl)morpholine 7 (0.199 g) was reacted with 4-(oxetan-3-yl)piperidine via General Procedure B to afford 0.11 g 4-(2-chloro-6-((4-(oxetan-3-yl)piperidin-1-yl)methyl)pyrido[3,2-d]pyrimidin-4-yl)morpholine.

Step 2: 4-(2-chloro-6-((4-(oxetan-3-yl)piperidin-1-yl)methyl)pyrido[3,2-d]pyrimidin-4-yl)morpholine (0.11 g) was reacted with 1-(tert-butyldimethylsilyl)-5-fluoro-4-(4,4,5,5-tetramethyl-1,3,2-dioxaborolan-2-yl)-1H-indole via General Procedure A to produce 59.8 mg of 130 following reverse phase HPLC purification. MS (Q1) 503.3 (M)+

Example 131

4-(1-((2-(2-ethyl-1H-benzo[d]imidazol-1-yl)-4-morpholinopyrido[3,2-d]pyrimidin-6-yl)methyl)azetidin-3-yl)morpholine 131

4-(1-((2-chloro-4-morpholinopyrido[3,2-d]pyrimidin-6-yl)methyl)azetidin-3-yl)morpholine from Example 126 (105 mg) was reacted with 2-ethylbenzimidazole and sodium-tert-butoxide (instead of cesium carbonate) via General Procedure C to afford 15.2 mg of 131 following reverse phase HPLC purification. MS (Q1) 515.3 (M)+

Example 132

2-(1-((2-(6-amino-5-methylpyridin-3-yl)-4-morpholinopyrido[3,2-d]pyrimidin-6-yl)methyl)piperidin-4-yl)propan-2-ol 132

Step 1: 3-methyl-5-(4,4,5,5-tetramethyl-1,3,2-dioxaborolan-2-yl)pyridin-2-amine

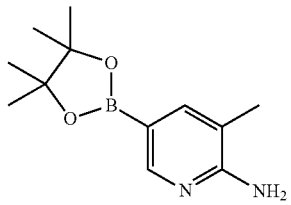

5-bromo-3-methylpyridin-2-amine (1 equiv.), bispinacol ester boronate (1.2 eq), potassium acetate (3 eq), Palladium Acetate (0.05 eq) and S-Phos (0.1 eq) in a microwave vial were added Acetonitrile (8 mL) and Water (8 mL). The reaction was heated into a biotage microwave at 140° C. for 30 minutes. The mixture was diluted with ethyl acetate and washed with twice with brine. The aqueous layer was back-extracted twice with ethyl acetate. The combined organic layers were dried over magnesium sulfate, filtered and concentrated to yield the crude 3-methyl-5-(4,4,5,5-tetramethyl-1,3,2-dioxaborolan-2-yl)pyridin-2-amine.

Step 2: 2-(1-((2-chloro-4-morpholinopyrido[3,2-d]pyrimidin-6-yl)methyl)piperidin-4-yl)propan-2-ol (0.185 g) was reacted with 3-methyl-5-(4,4,5,5-tetramethyl-1,3,2-dioxaborolan-2-yl)pyridin-2-amine via General Procedure A to produce 90.9 mg of 132 following reverse phase HPLC purification. MS (Q1) 478.3 (M)+

Example 133

2-(1-((2-(1H-indol-3-yl)-4-morpholinopyrido[3,2-d]pyrimidin-6-yl)methyl)piperidin-4-yl)propan-2-ol 133

2-(1-((2-chloro-4-morpholinopyrido[3,2-d]pyrimidin-6-yl)methyl)piperidin-4-yl)propan-2-ol from Example 8 (0.1 g) was reacted with 1-(phenylsulfonyl)-3-indoleboronic acid via General Procedure A to yield 56.9 mg 133 following phenylsulfonyl group deprotection with aqueous potassium hydroxide at 50° C. for 2 hours then reverse phase HPLC purification. MS (Q1) 487.3 (M)+

Example 134

4-(1-((2-(2-ethyl-1H-benzo[d]imidazol-1-yl)-4-morpholinopyrido[3,2-d]pyrimidin-6-yl)methyl)azetidin-3-yl)piperazin-2-one 134

4-(1-((2-chloro-4-morpholinopyrido[3,2-d]pyrimidin-6-yl)methyl)azetidin-3-yl)piperazin-2-one from Example 127 (90 mg) was reacted with 2-ethylbenzimidazole and sodium-tert-butoxide (instead of cesium carbonate) via General Procedure C to afford 10.2 mg of 134 following reverse phase HPLC purification. MS (Q1) 528.3 (M)+

Example 135

2-(1-((2-(2-methyl-1H-indol-1-yl)-4-morpholinopyrido[3,2-d]pyrimidin-6-yl)methyl)piperidin-4-yl)propan-2-ol 135

2-(1-((2-chloro-4-morpholinopyrido[3,2-d]pyrimidin-6-yl)methyl)piperidin-4-yl)propan-2-ol from Example 8 (0.1 g) was reacted with 2-methylindole and sodium-tert-butoxide (instead of cesium carbonate) via General Procedure C to afford 19 mg of 135 following reverse phase HPLC purification. MS (Q1) 501.3 (M)+

Example 136

2-(1-((2-(2-ethyl-2H-indazol-3-yl)-4-morpholinopyrido[3,2-d]pyrimidin-6-yl)methyl)piperidin-4-yl)propan-2-ol 136

Step 1: 2-(1-((4-morpholino-2-(tributylstannyl)pyrido[3,2-d]pyrimidin-6-yl)methyl)piperidin-4-yl)propan-2-ol

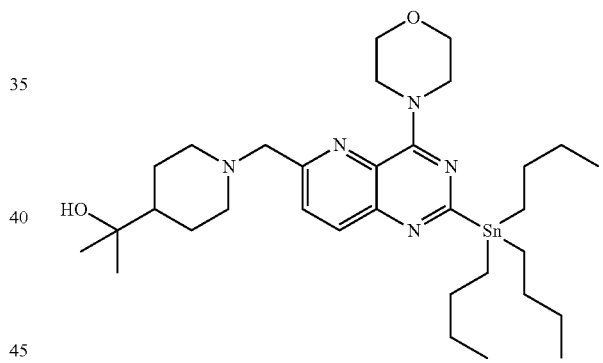

A solution of 2-(1-((2-chloro-4-morpholinopyrido[3,2-d]pyrimidin-6-yl)methyl)piperidin-4-yl)propan-2-ol from Example 8 (1.2 g) and bis(tributyltin) (2 eq) in 1,4-dioxane was degassed for 15 minutes prior to addition of bis[di-tert-butyl(4-dimethylaminophenyl)phosphine]dichloropalladium (II) (0.16 eq). The reaction was microwaved at 150° C. for 30 minutes then purified by flash column chromatography to afford 1.24 g of 2-(1-((4-morpholino-2-(tributylstannyl)pyrido[3,2-d]pyrimidin-6-yl)methyl)piperidin-4-yl)propan-2-ol as a clear oil.

Step 2: To a degassed solution of 2-(1-((4-morpholino-2-(tributylstannyl)pyrido[3,2-d]pyrimidin-6-yl)methyl)piperidin-4-yl)propan-2-ol (0.13 g) and 2-ethyl-3-iodo-2H-indazole (1.05 eq) in 1,4-dioxane (1.5 mL) was added copper(I) thiophene-2-carboxylate (1 eq) and tetrakis(triphenylphosphine)palladium(0) (0.05 eq). The reaction was microwaved at 140° C. for 30 minutes and then loaded onto Biotage isolute scx-2 catridge and eluted with 2M ammonia in Methanol. The crude material was purified by reverse phase HPLC to afford 36.6 mg of 136. MS (Q1) 516.3 (M)+

Example 137 tert-butyl 4-((2-(5-fluoro-1H-indol-4-yl)-4-morpholinopyrido[3,2-d]pyrimidin-6-yl)methyl)piperidine-1-carboxylate 137

Step 1: tert-butyl 4-((2-chloro-4-morpholinopyrido[3,2-d]pyrimidin-6-yl)methylene)piperidine-1-carboxylate

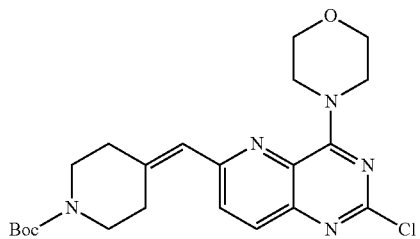 [SMILES: CC(C)(C)OC(=O)N1CCC(=Cc2ccc3nc(Cl)nc(N4CCOCC4)c3n2)CC1]

To a suspension of dimethyl (2-chloro-4-morpholinopyrido[3,2-d]pyrimidin-6-yl)methylphosphonate from Example 117 (0.71 g) in anhydrous THF (15 mL) at 0° C. was added 2.0 M of lithium diisopropylamide in THF (1.4 eq). The resulting solution was allowed to warm to RT (room temperature) before adding a solution of 1-boc-4-piperidone (1.4 eq) in anhydrous THF (3 mL). The reaction mixture was stirred at room temperature for 1 h, then partitioned between brine and DCM. The organic layer was isolated, dried (MgSO4), concentrated and recrystallized from methanol. The light yellow solid was filtered and collected to give 0.72 g of tert-butyl 4-((2-chloro-4-morpholinopyrido[3,2-d]pyrimidin-6-yl)methylene)piperidine-1-carboxylate as a light yellow solid.

Step 1: tert-butyl 4-((2-chloro-4-morpholinopyrido[3,2-d]pyrimidin-6-yl)methyl)piperidine-1-carboxylate

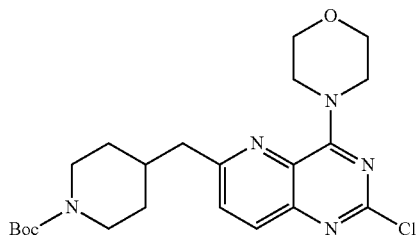 [SMILES: CC(C)(C)OC(=O)N1CCC(Cc2ccc3nc(Cl)nc(N4CCOCC4)c3n2)CC1]

tert-Butyl 4-((2-chloro-4-morpholinopyrido[3,2-d]pyrimidin-6-yl)methylene)piperidine-1-carboxylate (0.72 g) was brought up in ethanol (80 mL) and ethyl acetate (80 mL) and the flask was purged with nitrogen before addition of 10% Palladium on carbon (10 mol %). The reaction was placed under a hydrogen balloon and stirred at room temperature overnight. The reaction was filtered thru celite and purified by flash column chromatography to obtain 0.55 g tert-butyl 4-((2-chloro-4-morpholinopyrido[3,2-d]pyrimidin-6-yl)methyl)piperidine-1-carboxylate.

Step 3: tert-butyl 4-((2-chloro-4-morpholinopyrido[3,2-d]pyrimidin-6-yl)methyl)piperidine-1-carboxylate (0.2 g) was reacted with 1-(tert-butyldimethylsilyl)-5-fluoro-4-(4,4,5,5-tetramethyl-1,3,2-dioxaborolan-2-yl)-1H-indole via General Procedure A and purified via reverse phase hplc to produce 57.5 mg of 137. MS (Q1) 547.3 (M)+

Example 138

2-(1-((2-(1H-indazol-3-yl)-4-morpholinopyrido[3,2-d]pyrimidin-6-yl)methyl)piperidin-4-yl)propan-2-ol 138

To a degassed solution of 2-(1-((4-morpholino-2-(tributylstannyl)pyrido[3,2-d]pyrimidin-6-yl)methyl)piperidin-4-yl)propan-2-ol from Example 136 (0.15 g) and 3-iodo-1H-indazole (1.4 eq) in 1,4-dioxane (1.4 mL) was added Copper(I) thiophene-2-carboxylate (1 eq) and Tetrakis(triphenylphosphine)palladium(0) (0.125 eq). The reaction was microwaved at 140° C. for 30 minutes and then loaded onto biotage isolute scx-2 cartridge and eluted with 2M ammonia in Methanol. The crude material was purified by reverse phase HPLC to afford 23.4 mg of 138. MS (Q1) 488.3 (M)+

Example 139

4-(2-(5-fluoro-1H-indol-4-yl)-6-(piperidin-4-ylmethyl)pyrido[3,2-d]pyrimidin-4-yl)morpholine 139

Crude tert-butyl 4-((2-(5-fluoro-1H-indol-4-yl)-4-morpholinopyrido[3,2-d]pyrimidin-6-yl)methyl)piperidine-1-carboxylate 137 was reacted with 4N HCl in dioxane and purified by reverse phase HPLC to afford 16 mg of 139. MS (Q1) 447.2 (M)+

Example 140

1-(((2-(5-fluoro-1H-indol-4-yl)-4-morpholinopyrido[3,2-d]pyrimidin-6-yl)methyl)(methyl)amino)-2-methylpropan-2-ol 140

1-(((2-chloro-4-morpholinopyrido[3,2-d]pyrimidin-6-yl)methyl)(methyl)amino)-2-methylpropan-2-ol from Example 143 (0.12 g) was reacted with 1-(tert-butyldimethylsilyl)-5-fluoro-4-(4,4,5,5-tetramethyl-1,3,2-dioxaborolan-2-yl)-1H-indole via General Procedure A to produce 35.6 mg of 140 following reverse phase HPLC purification. MS (Q1) 465.2 (M)+

Example 141

4-(2-(5-fluoro-1H-indol-4-yl)-6-(1-isopropyl-1H-1,2,4-triazol-5-yl)pyrido[3,2-d]pyrimidin-4-yl)morpholine 141

Step 1: 2-chloro-4-morpholinopyrido[3,2-d]pyrimidine-6-carboxamide

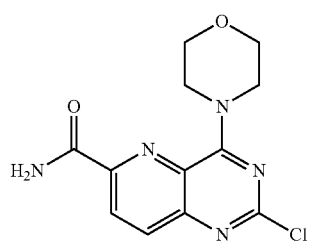 [SMILES: NC(=O)c1ccc2nc(Cl)nc(N3CCOCC3)c2n1]

2-Chloro-4-morpholinopyrido[3,2-d]pyrimidine-6-carboxylic acid from Example 118 (0.12 g) was reacted with ammonium chloride (7 eq), HATU (1.5 eq) and DIPEA (4 eq) in DMF (5.2 mL) for 30 minutes. The reaction mixture was then diluted with water and the orange solid was collected by filtration to give 90 mg of 2-chloro-4-morpholinopyrido[3,2-d]pyrimidine-6-carboxamide.

Step 2: 4-(2-chloro-6-(1-isopropyl-1H-1,2,4-triazol-5-yl)pyrido[3,2-d]pyrimidin-4-yl)morpholine

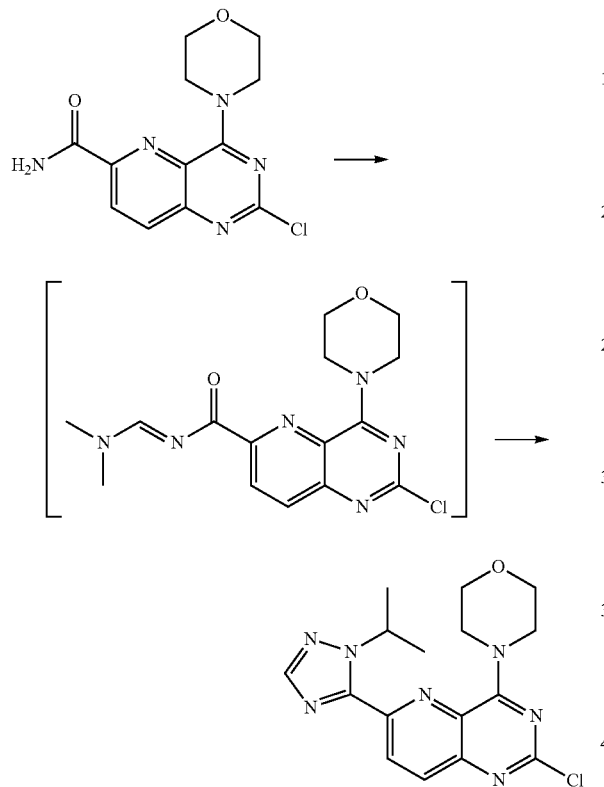

2-Chloro-4-morpholinopyrido[3,2-d]pyrimidine-6-carboxamide (90 mg) was suspended in toluene (5 mL) and treated with 1,1-dimethoxy-N,N-dimethylmethanamine (11 eq). The reaction was heated at 95° C. overnight then concentrated to dryness to afford crude (E)-2-chloro-N-((dimethylamino)methylene)-4-morpholinopyrido[3,2-d]pyrimidine-6-carboxamide. This intermediate was subsequently brought up in acetic acid (1.4 mL), isopropyl hydrazine hydrochloride was added and the reaction was stirred at room temperature for 1 hour. The reaction was concentrated to dryness then extracted with DCM and a saturated bicarbonate solution. The organic layer was dried (Mg₂SO₄), filtered and concentrated to give 0.11 g crude 4-(2-chloro-6-(1-isopropyl-1H-1,2,4-triazol-5-yl)pyrido[3,2-d]pyrimidin-4-yl)morpholine.

Step 3: 4-(2-chloro-6-(1-isopropyl-1H-1,2,4-triazol-5-yl)pyrido[3,2-d]pyrimidin-4-yl)morpholine (0.11 g) was reacted with 1-(tert-butyldimethylsilyl)-5-fluoro-4-(4,4,5,5-tetramethyl-1,3,2-dioxaborolan-2-yl)-1H-indole via General Procedure A to produce 57.7 mg of 141 following reverse phase HPLC purification. MS (Q1) 459.2 (M)+

Example 142

N-((2-(5-fluoro-1H-indol-4-yl)-4-morpholinopyrido[3,2-d]pyrimidin-6-yl)methyl)tetrahydro-2H-pyran-4-amine 142

Step 1: N-((2-chloro-4-morpholinopyrido[3,2-d]pyrimidin-6-yl)methyl)tetrahydro-2H-pyran-4-amine

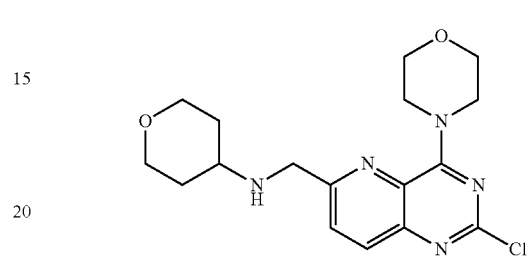

4-(6-(bromomethyl)-2-chloropyrido[3,2-d]pyrimidin-4-yl)morpholine 7 (0.3 g) was reacted with tetrahydro-2H-pyran-4-amine via General Procedure B to afford quantitative yield of N-((2-chloro-4-morpholinopyrido[3,2-d]pyrimidin-6-yl)methyl)tetrahydro-2H-pyran-4-amine.

Step 2: N-((2-chloro-4-morpholinopyrido[3,2-d]pyrimidin-6-yl)methyl)tetrahydro-2H-pyran-4-amine (0.17 g) was reacted with 1-(tert-butyldimethylsilyl)-5-fluoro-4-(4,4,5,5-tetramethyl-1,3,2-dioxaborolan-2-yl)-1H-indole via General Procedure A to produce 79.1 mg of 142 following reverse phase HPLC purification. MS (Q1) 463.2 (M)+

Example 143

1-((2-(5-fluoro-1H-indol-4-yl)-4-morpholinopyrido[3,2-d]pyrimidin-6-yl)methylamino)-2-methylpropan-2-ol 143

Step 1: 1-((2-chloro-4-morpholinopyrido[3,2-d]pyrimidin-6-yl)methylamino)-2-methylpropan-2-ol

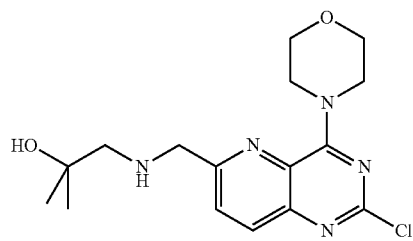 [SMILES: CC(C)(O)CNCc1ccc2nc(Cl)nc(N3CCOCC3)c2n1]

4-(6-(Bromomethyl)-2-chloropyrido[3,2-d]pyrimidin-4-yl)morpholine 7 (0.3 g) was reacted with 1-amino-2-methylpropan-2-ol via General Procedure B to afford quantitative yield of 1-((2-chloro-4-morpholinopyrido[3,2-d]pyrimidin-6-yl)methylamino)-2-methylpropan-2-ol.

Step 2: 1-(((2-chloro-4-morpholinopyrido[3,2-d]pyrimidin-6-yl)methyl)(methyl)amino)-2-methylpropan-2-ol

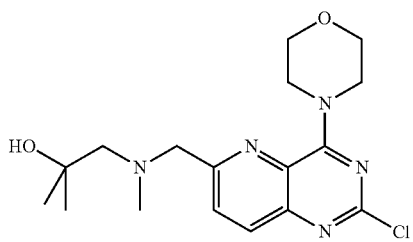 [SMILES: CN(Cc1ccc2nc(Cl)nc(N3CCOCC3)c2n1)CC(C)(C)O]

Paraformaldehyde (20 mg, 1.5 eq) was added to a solution of 1-((2-chloro-4-morpholinopyrido[3,2-d]pyrimidin-6-yl)methylamino)-2-methylpropan-2-ol (0.16 g) in DCM (2.5 mL). The reaction was stirred for 5 minutes before addition of sodium cyanoborohydride (1.2 eq). Methanol (1 mL) was added to the reaction mixture which was then stirred overnight at room temperature. The reaction was diluted with ethyl acetate and washed with water. The organic layer was dried over magnesium sulfate, filtered and concentrated to give 0.12 g of 1-(((2-chloro-4-morpholinopyrido[3,2-d]pyrimidin-6-yl)methyl)(methyl)amino)-2-methylpropan-2-ol as a yellow oil.

Step 3: 1-((2-chloro-4-morpholinopyrido[3,2-d]pyrimidin-6-yl)methylamino)-2-methylpropan-2-ol (0.16 g) was reacted with 1-(tert-butyldimethylsilyl)-5-fluoro-4-(4,4,5,5-tetramethyl-1,3,2-dioxaborolan-2-yl)-1H-indole via General Procedure A to produce 75.9 mg of 143 following reverse phase HPLC purification. MS (Q1) 451.2 (M)+

Example 144

4-(6-((3,3-dimethylpyrrolidin-1-yl)methyl)-2-(5-fluoro-1H-indol-4-yl)pyrido[3,2-d]pyrimidin-4-yl)morpholine 144

Step 1: 4-(2-chloro-6-((3,3-dimethylpyrrolidin-1-yl)methyl)pyrido[3,2-d]pyrimidin-4-yl)morpholine

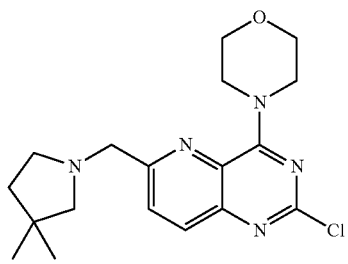 [SMILES: CC1(C)CCN(Cc2ccc3nc(Cl)nc(N4CCOCC4)c3n2)C1]

4-(6-(Bromomethyl)-2-chloropyrido[3,2-d]pyrimidin-4-yl)morpholine 7 (0.225 g) was reacted with 3,3-dimethylpyrrolidine via General Procedure B to afford quantitative yield of 4-(2-chloro-6-((3,3-dimethylpyrrolidin-1-yl)methyl)pyrido[3,2-d]pyrimidin-4-yl)morpholine.

Step 2: 4-(2-chloro-6-((3,3-dimethylpyrrolidin-1-yl)methyl)pyrido[3,2-d]pyrimidin-4-yl)morpholine (0.28 g) was reacted with 1-(tert-butyldimethylsilyl)-5-fluoro-4-(4,4,5,5-tetramethyl-1,3,2-dioxaborolan-2-yl)-1H-indole via General Procedure A to produce 70.2 mg of 144 following reverse phase HPLC purification. MS (Q1) 461.2 (M)+

Example 145

N-((2-(5-fluoro-1H-indol-4-yl)-4-morpholinopyrido[3,2-d]pyrimidin-6-yl)methyl)pivalamide 145

Step 1: (2-chloro-4-morpholinopyrido[3,2-d]pyrimidin-6-yl)methanamine

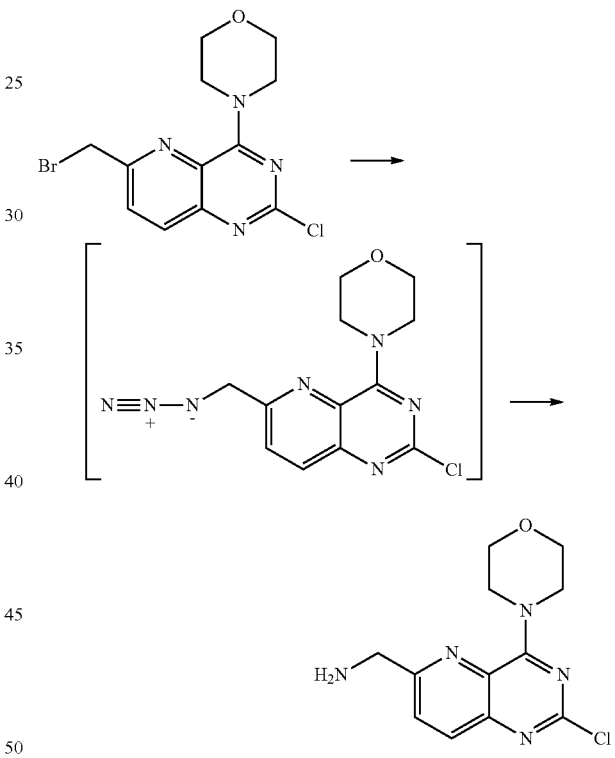

To 4-(6-(bromomethyl)-2-chloropyrido[3,2-d]pyrimidin-4-yl)morpholine 7 (0.5 g) in DMF (11 mL) was added sodium azide (2 eq). The reaction was heated at 60° C. for 1 hour and then extracted with ethyl acetate and brine. The organic layer was dried ($Mg_2SO_4$), filtered and concentrated to afford 0.437 g of crude 4-(6-(azidomethyl)-2-chloropyrido[3,2-d]pyrimidin-4-yl)morpholine. This intermediate was then suspended in THF (4 mL), triphenylphosphine (2 eq) was added and the reaction was stirred at room temperature for 1.5 hours. Water (0.1 mL) was added to the reaction mixture which was then loaded onto a 10 g biotage isolute scx-2 cartridge then eluted with 2M ammonia in methanol then purified by flash column chromatography to yield 0.27 g (2-chloro-4-morpholinopyrido[3,2-d]pyrimidin-6-yl)methanamine.

Step 2: N-((2-chloro-4-morpholinopyrido[3,2-d]pyrimidin-6-yl)methyl)pivalamide

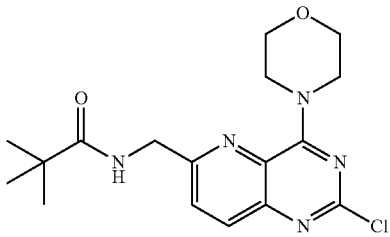 [SMILES: CC(C)(C)C(=O)NCc1ccc2nc(Cl)nc(N3CCOCC3)c2n1]

(2-chloro-4-morpholinopyrido[3,2-d]pyrimidin-6-yl)methanamine (0.1 g) was added to a pre-stirred (15 minutes) solution of trimethylacetic acid (1.2 eq), 1-hydroxybenzotriazole (1.1 eq.), N-(3-dimethylaminopropyl)-N'-ethylcarbodiimide hydrochloride (1.1 eq.), triethylamine (2 eq.) in N,N-dimethylformamide (2.77 mL). The reaction was stirred overnight then extracted with ethyl acetate and brine. The organic layer was dried ($Mg_2SO_4$), filtered and concentrated to give quantitative yield of N-((2-chloro-4-morpholinopyrido[3,2-d]pyrimidin-6-yl)methyl)pivalamide.

Step 3: N-((2-chloro-4-morpholinopyrido[3,2-d]pyrimidin-6-yl)methyl)pivalamide (0.13 g) was reacted with 1-(tert-butyldimethylsilyl)-5-fluoro-4-(4,4,5,5-tetramethyl-1,3,2-dioxaborolan-2-yl)-1H-indole via General Procedure A to produce 44 mg of 145 following reverse phase HPLC purification. MS (Q1) 463.2 (M)+

Example 146

4-((2-(5-fluoro-1H-indol-4-yl)-4-morpholinopyrido[3,2-d]pyrimidin-6-yl)methyl)morpholine 146

Step 1: 4-((2-chloro-4-morpholinopyrido[3,2-d]pyrimidin-6-yl)methyl)morpholine

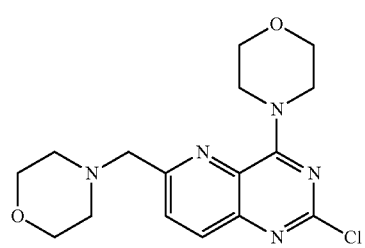

4-(6-(Bromomethyl)-2-chloropyrido[3,2-d]pyrimidin-4-yl)morpholine 7 (0.1 g) was reacted with morpholine via General Procedure B to afford quantitative yield of 4-((2-chloro-4-morpholinopyrido[3,2-d]pyrimidin-6-yl)methyl)morpholine.

Step 2: 4-((2-chloro-4-morpholinopyrido[3,2-d]pyrimidin-6-yl)methyl)morpholine (0.1 g) was reacted with 1-(tert-butyldimethylsilyl)-5-fluoro-4-(4,4,5,5-tetramethyl-1,3,2-dioxaborolan-2-yl)-1H-indole via General Procedure A to produce 94.7 mg of 146 following reverse phase HPLC purification. MS (Q1) 449.2 (M)+

Example 147

N-((2-(5-fluoro-1H-indol-4-yl)-4-morpholinopyrido[3,2-d]pyrimidin-6-yl)methyl)isobutyramide 147

Step 1: N-((2-chloro-4-morpholinopyrido[3,2-d]pyrimidin-6-yl)methyl)isobutyramide

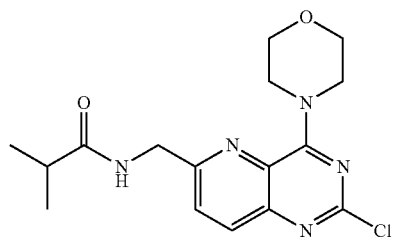 [SMILES: CC(C)C(=O)NCc1ccc2nc(Cl)nc(N3CCOCC3)c2n1]

(2-Chloro-4-morpholinopyrido[3,2-d]pyrimidin-6-yl)methanamine from Example 145 (0.1 g) was added to a pre-stirred (15 minutes) solution of 2-methylpropanoic acid (1.2 eq), 1-hydroxybenzotriazole (1.1), N-(3-dimethylaminopropyl)-N'-ethylcarbodiimide hydrochloride (1.1), triethylamine (2 eq) in N,N-dimethylformamide (2.77 mL). The reaction was stirred overnight then extracted with Ethyl Acetate and brine. The organic layer was dried ($Mg_2SO_4$), filtered and concentrated to give quantitative yield of N-((2-chloro-4-morpholinopyrido[3,2-d]pyrimidin-6-yl)methyl)isobutyramide.

Step 2: N-((2-chloro-4-morpholinopyrido[3,2-d]pyrimidin-6-yl)methyl)isobutyramide (0.125 g) was reacted with 1-(tert-butyldimethylsilyl)-5-fluoro-4-(4,4,5,5-tetramethyl-1,3,2-dioxaborolan-2-yl)-1H-indole via General Procedure A to produce 14.5 mg of 147 following reverse phase HPLC purification. MS (Q1) 449.2 (M)+

Example 148

1-(4-((2-(5-fluoro-1H-indol-4-yl)-4-morpholinopyrido[3,2-d]pyrimidin-6-yl)methyl)piperidin-1-yl)ethanone 148

Step 1: 4-(2-chloro-6-(piperidin-4-ylmethyl)pyrido[3,2-d]pyrimidin-4-yl)morpholine

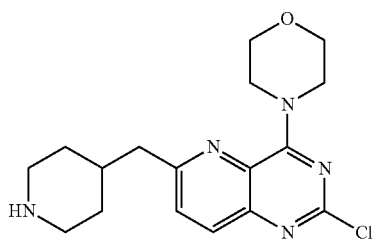 [SMILES: Clc1nc(N2CCOCC2)c2nc(CC3CCNCC3)ccc2n1]

tert-butyl 4-((2-chloro-4-morpholinopyrido[3,2-d]pyrimidin-6-yl)methyl)piperidine-1-carboxylate from Example 137 (0.33 g) in DCM (5 mL) was treated with 4N HCl in dioxane (0.9 mL) for 30 minutes at room temperature. The reaction mixture was concentrated to dryness to afford quantitative yield of 4-(2-chloro-6-(piperidin-4-ylmethyl)pyrido[3,2-d]pyrimidin-4-yl)morpholine.

Step 2: 1-(4-((2-chloro-4-morpholinopyrido[3,2-d]pyrimidin-6-yl)methyl)piperidin-1-yl)ethanone

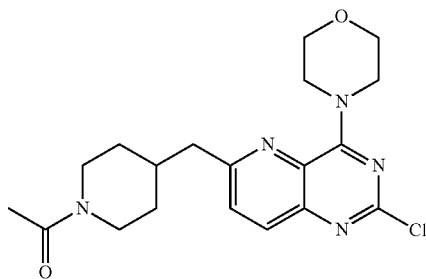 [SMILES: CC(=O)N1CCC(Cc2ccc3nc(Cl)nc(N4CCOCC4)c3n2)CC1]

4-(2-chloro-6-(piperidin-4-ylmethyl)pyrido[3,2-d]pyrimidin-4-yl)morpholine (40 mg) was added to a pre-stirred (15 minutes) solution of acetic acid (5 eq), 1-Hydroxybenzotriazole (HOBt, 1.2 eq.), N-(3-Dimethylaminopropyl)-N'-ethylcarbodiimide hydrochloride (1.5 eq.), DIPEA (5 eq) in N,N-Dimethylformamide (DMF, 0.9 mL). The reaction was stirred overnight then extracted with Ethyl Acetate and brine. The organic layer was dried (Mg$_2$SO$_4$), filtered and concentrated to give quantitative yield of 1-(4-((2-chloro-4-morpholinopyrido[3,2-d]pyrimidin-6-yl)methyl)piperidin-1-yl)ethanone.

Step 3: 1-(4-((2-chloro-4-morpholinopyrido[3,2-d]pyrimidin-6-yl)methyl)piperidin-1-yl)ethanone (30 mg) was reacted with 1-(tert-butyldimethylsilyl)-5-fluoro-4-(4,4,5,5-tetramethyl-1,3,2-dioxaborolan-2-yl)-1H-indole via General Procedure A to produce 13.7 mg of 148 following reverse phase HPLC purification. MS (Q1) 489.2 (M)+

Example 149

1-(4-((2-(5-fluoro-1H-indol-4-yl)-4-morpholinopyrido[3,2-d]pyrimidin-6-yl)methyl)piperidin-1-yl)-2-methylpropan-1-one 149

Step 1: 1-(4-((2-chloro-4-morpholinopyrido[3,2-d]pyrimidin-6-yl)methyl)piperidin-1-yl)-2-methylpropan-1-one

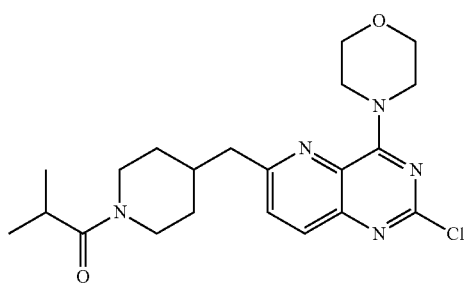 [SMILES: CC(C)C(=O)N1CCC(Cc2ccc3nc(Cl)nc(N4CCOCC4)c3n2)CC1]

4-(2-Chloro-6-(piperidin-4-ylmethyl)pyrido[3,2-d]pyrimidin-4-yl)morpholine from Example 148 (40 mg) was added to a pre-stirred (15 minutes) solution of 2-methylpropanoic acid (2 eq.), 1-Hydroxybenzotriazole (1.2), N-(3-Dimethylaminopropyl)-N'-ethylcarbodiimide hydrochloride (1.5 eq.), diisopropylethylamine (DIPEA, 5 eq.) in N,N-Dimethylformamide (0.9 mL). The reaction was stirred overnight then extracted with Ethyl Acetate and brine. The organic layer was dried (Mg$_2$SO$_4$), filtered and concentrated to give quantitative yield of 1-(4-((2-chloro-4-morpholinopyrido[3,2-d]pyrimidin-6-yl)methyl)piperidin-1-yl)-2-methylpropan-1-one.

Step 2: 1-(4-((2-Chloro-4-morpholinopyrido[3,2-d]pyrimidin-6-yl)methyl)piperidin-1-yl)-2-methylpropan-1-one (60 mg) was reacted with 1-(tert-butyldimethylsilyl)-5-fluoro-4-(4,4,5,5-tetramethyl-1,3,2-dioxaborolan-2-yl)-1H-indole via General Procedure A to produce 19.9 mg of 149 following reverse phase HPLC purification. MS (Q1) 517.3 (M)+

Example 150

(S)-4-(1-((2-(2-(1-methoxyethyl)-1H-benzo[d]imidazol-1-yl)-4-morpholinopyrido[3,2-d]pyrimidin-6-yl)methyl)azetidin-3-yl)morpholine 150

Following General procedure D, 4-(1-((2-chloro-4-morpholinopyrido[3,2-d]pyrimidin-6-yl)methyl)azetidin-3-yl)morpholine from Example 126 was reacted with (S)-2-(1-methoxyethyl)-1H-benzo[d]imidazole to give 150. $^1$H NMR (400 MHz, DMSO) δ 8.18 (d, J=8.6 Hz, 1H), 8.01 (dd, J=6.7, 1.8 Hz, 1H), 7.84 (d, J=8.7 Hz, 1H), 7.73 (dd, J=6.7, 2.1 Hz, 1H), 7.38-7.24 (m, 2H), 5.50 (q, J=6.4 Hz, 1H), 4.53 (br s, 4H), 3.92-3.79 (m, 6H), 3.63-3.52 (m, 4H), 3.45 (t, J=6.2 Hz, 2H), 3.09 (s, 3H), 2.97 (overlapping m, 3H), 2.25 (br s, 4H), 1.63 (d, J=6.4 Hz, 3H). LCMS: 345.3

Example 153

2-(1-((2-(2-(dimethylamino)-1H-benzo[d]imidazol-1-yl)-4-morpholinopyrido[3,2-d]pyrimidin-6-yl)methyl)piperidin-4-yl)propan-2-ol 153

2-(1-((2-chloro-4-morpholinopyrido[3,2-d]pyrimidin-6-yl)methyl)piperidin-4-yl)propan-2-ol from Example 8 (0.25 g) was reacted with N,N-dimethyl-1H-benzo[d]imidazol-2-amine via General Procedure D to produce 59.5 mg of 153 following reverse phase HPLC purification. MS (Q1) 531.3 (M)+

Example 154

4-(2-(5-fluoro-1H-indol-4-yl)-6-((tetrahydro-2H-pyran-4-yl)methyl)pyrido[3,2-d]pyrimidin-4-yl)morpholine 154

Step 1: 4-(6-((2H-pyran-4(3H,5H,6H)-ylidene)methyl)-2-chloropyrido[3,2-d]pyrimidin-4-yl)morpholine

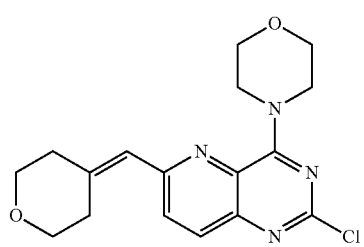 [SMILES: Clc1nc(N2CCOCC2)c2nc(C=C3CCOCC3)ccc2n1]

To a suspension of dimethyl (2-chloro-4-morpholinopyrido[3,2-d]pyrimidin-6-yl)methylphosphonate from Example 117 (0.45 g) in anhydrous THF (6 mL) at 0° C. was added 2.0 M of lithium diisopropylamide in tetrahydrofuran (1.5 eq). The resulting solution was allowed to warm to RT before adding a solution of dihydro-2H-pyran-4(3H)-one (1.5 eq) in anhydrous THF (3 mL). The reaction mixture was stirred at room temperature for 1 h, then partitioned between brine and Ethyl Acetate. The organic layer was isolated, dried (MgSO4), concentrated and recrystallized from methanol. The light yellow solid was filtered and collected to give 0.36 g of 4-(6-((2H-pyran-4(3H,5H,6H)-ylidene)methyl)-2-chloropyrido[3,2-d]pyrimidin-4-yl)morpholine as a light yellow solid.

Step 2: 4-(2-chloro-6-((tetrahydro-2H-pyran-4-yl)methyl)pyrido[3,2-d]pyrimidin-4-yl)morpholine

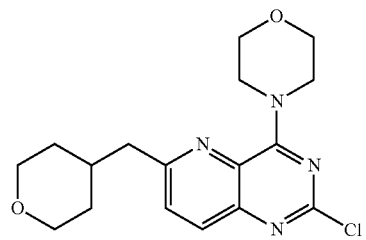 [SMILES: Clc1nc(N2CCOCC2)c2nc(CC3CCOCC3)ccc2n1]

4-(6-((2H-Pyran-4(3H,5H,6H)-ylidene)methyl)-2-chloropyrido[3,2-d]pyrimidin-4-yl)morpholine (0.22 g) was brought up in ethanol (30 mL) and ethyl acetate (30 mL) and the flask was purged with nitrogen before addition of 10% Palladium on Carbon (10 mol %). The reaction was placed under a hydrogen balloon and stirred at room temperature for 2.5 hours. The reaction was filtered thru celite and purified by flash column chromatography to obtain 0.11 g 4-(2-chloro-6-((tetrahydro-2H-pyran-4-yl)methyl)pyrido[3,2-d]pyrimidin-4-yl)morpholine.

Step 3: 4-(2-chloro-6-((tetrahydro-2H-pyran-4-yl)methyl)pyrido[3,2-d]pyrimidin-4-yl)morpholine (0.05 g) was reacted with 1-(tert-butyldimethylsilyl)-5-fluoro-4-(4,4,5,5-tetramethyl-1,3,2-dioxaborolan-2-yl)-1H-indole via General Procedure A to produce 38.8 mg of 154 following reverse phase HPLC purification. MS (Q1) 448.2 (M)+

Example 156

2-(1-((4-morpholino-2-(2-(trifluoromethyl)-1H-benzo[d]imidazol-1-yl)pyrido[3,2-d]pyrimidin-6-yl)methyl)piperidin-4-yl)propan-2-ol 156

Following General Procedure D, 2-(1-((2-chloro-4-morpholinopyrido[3,2-d]pyrimidin-6-yl)methyl)piperidin-4-yl)propan-2-ol from Example 8 was reacted with 2-(trifluoromethyl)-1H-benzo[d]imidazole to give 156. ¹H NMR (400 MHz, DMSO) δ 8.20 (d, J=8.6 Hz, 1H), 8.14 (d, J=8.3 Hz, 1H), 7.94 (d, J=8.6 Hz, 2H), 7.56 (t, J=7.5 Hz, 1H), 7.49 (t, J=7.6 Hz, 1H), 4.56 (s, 4H), 4.04 (s, 1H), 3.86-3.79 (m, 4H), 3.75 (s, 2H), 2.93 (d, J=11.0 Hz, 2H), 2.00 (t, J=10.9 Hz, 2H), 1.67 (d, J=12.1 Hz, 2H), 1.38-1.12 (m, 3H), 1.04 (s, 6H). LCMS: 556.3

Example 157

2-(1-((2-(2-(difluoromethyl)-1H-benzo[d]imidazol-1-yl)-4-morpholinopyrido[3,2-d]pyrimidin-6-yl)methyl)piperidin-4-yl)propan-2-ol 157

Following General Procedure D, 2-(1-((2-chloro-4-morpholinopyrido[3,2-d]pyrimidin-6-yl)methyl)piperidin-4-yl)propan-2-ol from Example 8 was reacted with 2-(difluoromethyl)-1H-benzo[d]imidazole to give 157. ¹H NMR (400 MHz, DMSO) δ 8.43 (d, J=8.3 Hz, 1H), 8.23 (d, J=8.7 Hz, 1H), 8.00-7.72 (overlapping m, 3H), 7.51 (app t, J=7.7 Hz, 1H), 7.44 (app t, J=7.7 Hz, 1H), 4.56 (br s, 4H), 4.03 (s, 1H), 3.86 (br s, 4H), 3.74 (br s, 2H), 2.92 (d, J=10.6 Hz, 2H), 1.99 (t, J=11.3 Hz, 2H), 1.67 (d, J=11.8 Hz, 2H), 1.38-1.10 (overlapping m, 3H), 1.04 (s, 6H). LCMS: 538.3

Example 158

2-(1-(6-((4-(2-hydroxypropan-2-yl)piperidin-1-yl)methyl)-4-morpholinopyrido[3,2-d]pyrimidin-2-yl)-1H-benzo[d]imidazol-2-yl)acetonitrile 158

Following General Procedure D, 2-(1-((2-chloro-4-morpholinopyrido[3,2-d]pyrimidin-6-yl)methyl)piperidin-4-yl)propan-2-ol from Example 8 was reacted with 2-(1H-benzo[d]imidazol-2-yl)acetonitrile to give 158. ¹H NMR (400 MHz, DMSO) δ 8.32 (d, J=7.8 Hz, 1H), 8.21 (d, J=8.5 Hz, 1H), 7.91 (d, J=8.6 Hz, 1H), 7.76 (d, J=7.8 Hz, 1H), 7.38 (overlapping m, 2H), 4.88 (s, 2H), 4.54 (s, 4H), 4.04 (s, 1H), 3.86 (s, 4H), 3.73 (s, 2H), 2.92 (d, J=10.5 Hz, 2H), 1.99 (t, J=11.5 Hz, 2H), 1.67 (d, J=11.7 Hz, 2H), 1.26 (overlapping m, 3H), 1.04 (s, 6H). LCMS: 527.3

Example 163

N,N-dimethyl-1-(4-morpholino-6-((3-(1,1-dioxo)thiomorpholinoazetidin-1-yl)methyl)pyrido[3,2-d]pyrimidin-2-yl)-1H-benzo[d]imidazol-2-amine 163

4-(2-chloro-6-((3-(1,1-dioxo)thiomorpholinoazetidin-1-yl)methyl)pyrido[3,2-d]pyrimidin-4-yl)morpholine from Example 129 (0.1 g) was reacted with N,N-dimethyl-1H-benzo[d]imidazol-2-amine via General Procedure D to produce 12.5 mg of 163 following reverse phase HPLC purification. MS (Q1) 578.2 (M)+

Example 164

(S)-1-(4-((2-(2-(1-methoxyethyl)-1H-benzo[d]imidazol-1-yl)-4-morpholinopyrido[3,2-d]pyrimidin-6-yl)methyl)piperidin-1-yl)ethanone 164

1-(4-((2-Chloro-4-morpholinopyrido[3,2-d]pyrimidin-6-yl)methyl)piperidin-1-yl)ethanone from Example 148 (0.125 g) was reacted with (S)-2-(1-methoxyethyl)-1H-benzo[d]imidazole via General Procedure D to produce 22.1 mg of 164 following reverse phase HPLC purification. MS (Q1) 530.3 (M)+

Example 165

1-(4-((2-(2-(dimethylamino)-1H-benzo[d]imidazol-1-yl)-4-morpholinopyrido[3,2-d]pyrimidin-6-yl)methyl)piperidin-1-yl)ethanone 165

1-(4-((2-Chloro-4-morpholinopyrido[3,2-d]pyrimidin-6-yl)methyl)piperidin-1-yl)ethanone from Example 148 (0.125 g) was reacted with N,N-dimethyl-1H-benzo[d]imidazol-2-amine via General Procedure D to produce 47.5 mg of 165 following reverse phase HPLC purification. MS (Q1) 515.2 (M)+

Example 166

2-(1-((2-([1,2,4]triazolo[1,5-a]pyridin-5-yl)-4-morpholinopyrido[3,2-d]pyrimidin-6-yl)methyl)piperidin-4-yl)propan-2-ol 166

2-(1-((2-Chloro-4-morpholinopyrido[3,2-d]pyrimidin-6-yl)methyl)piperidin-4-yl)propan-2-ol from Example 8 (50 mg, 0.12 mmol) was dissolved in 2 mL of THF and treated with CuI (1.2 mg, 0.006 mmol) and 5-(tributylstannyl)-[1,2,4]triazolo[1,5-a]pyridine (65.4 mg, 0.16 mmol). The solution was sparged with bubbling nitrogen and tetrakis(triphenylphosphine)palladium (0) (7 mg, 0.006 mmol) was added. The mixture was heated in an Agilent microwave (140° C., 20 min). The solution was cooled to room temperature and concentrated. Purification by reverse phase HPLC gave 166 as a colorless solid. $^1$H NMR (400 MHz, DMSO) δ 8.52 (s, 1H), 8.21 (d, J=8.6 Hz, 1H), 7.99 (d, J=8.9 Hz, 1H), 7.91 (d, J=8.7 Hz, 1H), 7.84-7.74 (m, 1H), 7.65 (d, J=7.0 Hz, 1H), 4.51 (s, 4H), 4.03 (s, 1H), 3.83-3.77 (m, 4H), 3.75 (s, 2H), 2.93 (d, J=11.1 Hz, 2H), 2.00 (t, J=11.2 Hz, 2H), 1.67 (d, J=11.4 Hz, 2H), 1.24 (overlapping m, 3H), 1.04 (s, 6H). LCMS: 489.2

Example 167

N,N-dimethyl-1-(4-morpholino-6-((3-morpholinoazetidin-1-yl)methyl)pyrido[3,2-d]pyrimidin-2-yl)-1H-benzo[d]imidazol-2-amine 167

4-(1-((2-chloro-4-morpholinopyrido[3,2-d]pyrimidin-6-yl)methyl)azetidin-3-yl)morpholine from Example 126 (75 mg) was reacted with N,N-dimethyl-1H-benzo[d]imidazol-2-amine via General Procedure D to produce 6.8 mg of 167 following reverse phase HPLC purification. MS (Q1) 530.2 (M)+

Example 168

2-(1-((2-(2-(2-hydroxyethyl)-1H-benzo[d]imidazol-1-yl)-4-morpholinopyrido[3,2-d]pyrimidin-6-yl)methyl)piperidin-4-yl)propan-2-ol 168

2-(1-((2-chloro-4-morpholinopyrido[3,2-d]pyrimidin-6-yl)methyl)piperidin-4-yl)propan-2-ol from Example 8 (0.15 g) was reacted with 2-(1H-benzo[d]imidazol-2-yl)ethanol via General Procedure D to produce 19 mg of 168 following reverse phase HPLC purification. MS (Q1) 532.3 (M)+

Example 169

4-(2-(2-(difluoromethyl)-1H-benzo[d]imidazol-1-yl)-6-((3-(1,1-dioxo)thiomorpholinoazetidin-1-yl)methyl)pyrido[3,2-d]pyrimidin-4-yl)morpholine 169

4-(2-chloro-6-((3-(1,1-dioxo)thiomorpholinoazetidin-1-yl)methyl)pyrido[3,2-d]pyrimidin-4-yl)morpholine from Example 129 (0.125 g) was reacted with 2-(difluoromethyl)-1H-benzo[d]imidazole via General Procedure D to produce 50.9 mg of 169 following reverse phase HPLC purification. MS (Q1) 585.2 (M)+

Example 171

1-(4-((2-(2-(difluoromethyl)-1H-benzo[d]imidazol-1-yl)-4-morpholinopyrido[3,2-d]pyrimidin-6-yl)methyl)piperidin-1-yl)ethanone 171

1-(4-((2-chloro-4-morpholinopyrido[3,2-d]pyrimidin-6-yl)methyl)piperidin-1-yl)ethanone from Example 148 (0.135 g) was reacted with 2-(difluoromethyl)-1H-benzo[d]imidazole via General Procedure D to produce 31.4 mg of 171 following reverse phase HPLC purification. MS (Q1) 522.2 (M)+

Example 172

4-(1-((2-(2-(difluoromethyl)-1H-benzo[d]imidazol-1-yl)-4-morpholinopyrido[3,2-d]pyrimidin-6-yl)methyl)azetidin-3-yl)morpholine 172

4-(1-((2-chloro-4-morpholinopyrido[3,2-d]pyrimidin-6-yl)methyl)azetidin-3-yl)morpholine from Example 126 (0.07 g) was reacted with 2-(difluoromethyl)-1H-benzo[d]imidazole via General Procedure D to produce 10.7 mg of 172 following reverse phase HPLC purification. MS (Q1) 537.2 (M)+

Example 173

2-(1-((4-morpholino-2-(2-(2,2,2-trifluoroethyl)-1H-benzo[d]imidazol-1-yl)pyrido[3,2-d]pyrimidin-6-yl)methyl)piperidin-4-yl)propan-2-ol 173

A small vial was charged with 2-(1-((2-chloro-4-morpholinopyrido[3,2-d]pyrimidin-6-yl)methyl)piperidin-4-yl)propan-2-ol from Example 8 (0.070 g, 0.17 mmol), 2-(2,2,2-trifluoro-ethyl)-1H-benzoimidazole (0.042 g, 0.21 mmol), XPhos (0.012 g, 0.026 mmol) and Potassium phosphate (0.110 g, 0.519 mmol). Dry 1,4-dioxane (1.9 mL, 0.024 mol) was added. The whole was sparged with nitrogen for 3 min. Tris(dibenzylideneacetone)dipalladium(0) (0.012 g, 0.013 mmol) was added under nitrogen. The vial was sealed and heated at 155° C. (heating block temp) for 4 h. LC/MS indicates complete reaction. The solution was diluted with water and extracted with dichloromethane 3 times. The combined organics were washed with brine and dried over sodium sulfate. The material was purified by reverse phase HPLC to give 51.3 mg (53% yield) of 173 as a white solid. LCMS (MH$^+$) =570.3. $^1$H NMR (400 MHz, DMSO) δ 8.25-8.15 (m, 2H), 7.91 (d, J=8.7 Hz, 1H), 7.76 (d, J=7.5 Hz, 1H), 7.42-7.31 (m, 2H), 4.65 (q, J=10.7 Hz, 2H), 4.90-4.25 (br m, 4H), 4.05 (s, 1H), 3.88-3.80 (m, 4H), 3.74 (s, 2H), 2.92 (d, J=11.1 Hz, 2H), 1.99 (t, J=11.1 Hz, 2H), 1.67 (d, J=11.2 Hz, 2H), 1.37-1.23 (m, 2H), 1.22-1.12 (m, 1H), 1.04 (s, 6H)

Example 901

PI3K Isoform Inhibition Assay (p110 Alpha, Beta, Gamma, Delta: α, β, γ, δ)

PI3K enzymatic activity was assayed by measuring the amount of product phosphatidylinositol 3,4,5-phosphate (PIP3) formed from substrate 4,5 phosphatidylinositol 4,5-phosphate (PIP2) using a fluorescence polarization displacement assay. The decrease in fluorescence polarization of a fluorescent PIP$_3$ probe is measured as it is displaced from a PIP$_3$-binding protein GRP-1 detector by PI3K-catalyzed product. Assays were conducted in 384-well black Proxiplates in the presence of 10 mM Tris (pH 7.5), 50 mM NaCl, 4 mM $MgCl_2$, 5% glycerol, 25 μM ATP, 10 μM $PIP_2$ (Echelon Biosciences), 0.05% 3-[(3-cholamidopropyl)dimethylammonio]-1-propanesulfonate, 1 mM dithiothreitol, and 2% DMSO. The kinase reactions were initiated by the addition of 40 ng/mL p110α/p85α, 300 ng/mL p110β/p85α, 40 ng/mL p110γ, or 40 ng/mL p110δ/p85α (Upstate Group, Millipore; Dundee, UK), and 10 μM $PIP_2$ (Echelon Biosciences) to the wells. The reactions were stopped at time points that yielded a fixed change in fluorescence polarization consistent with initial rate conditions (typically 30 minutes), by the addition of 12.5 mM EDTA, 100 nM GRP-1 detector, and 5 nM tetramethylrhodamine-labeled $PIP_3$ (TAMRA-$PIP_3$; Echelon Biosciences). After 60 minutes of incubation at room temperature to allow equilibration of labeled and unlabeled PIP3 binding, the parallel and perpendicular components of the fluorescence emissions from each sample were measured at an excitation wavelength of 530 nm and an emission wavelength of 590 nm using an Envision fluorescent plate reader with a rhodamine filter (PerkinElmer Life and Analytical Sciences; Wellesley, Mass.). The assay is capable of detecting 0.1-2.0 μM $PIP_3$ product. The $IC_{50}$ values were obtained by fitting the dose-dependent inhibition data to a 4-parameter equation using Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

The same protocol may be used to establish $IC_{50}$ values for p110α (alpha) PI3K binding.

Recombinant PI3K p110 isoforms alpha, beta, and delta may be prepared and purified according to US 2008/0275067 from recombinant PI3K heterodimeric complexes consisting of a p110 catalytic subunit and a p85 regulatory subunit overexpressed using the BAC-TO-BAC® HT baculovirus expression system (GIBCO/BRL), and then purified for use in biochemical assays. The four Class I PI 3-kinases are cloned into baculovirus vectors as follows:

p110 delta: A FLAG™-tagged (Eastman Kodak Co., U.S. Pat. No. 4,703,004; U.S. Pat. No. 4,782,137; U.S. Pat. No. 4,851,341) version of human p110.delta (Chantry et al., J. Biol. Chem. (1997) 272:19236-41) is subcloned using standard recombinant DNA techniques into the BamH1-Xba1 site of the insect cell expression vector pFastbac HTb (Life Technologies, Gaithersburg, Md.), such that the clone is in frame with the His tag of the vector.

p110 alpha: Similar to the method used for p110 delta, described above, a FLAG™-tagged version of p110 alpha (Volinia et al (1994) Genomics, 24(3):427-77) was subcloned in BamH1-HindIII sites of pFastbac HTb (Life Technologies) such that the clone was in frame with the His tag of the vector.

p110 beta: A p110 beta (see Hu et al (1993) Mol. Cell. Biol., 13:7677-88) clone was amplified from the human MARATHON™ Ready spleen cDNA library (Clontech, Palo Alto Calif.) according to the manufacturer's protocol using the specified primers.

The p110 delta binding IC50 values and delta/alpha selectivity of selected compounds from Table 1 include:

| Compound No. | p110 delta IC50 (micromolar) | IC50 p110 alpha/IC50 p110 delta |
|---|---|---|
| 101 | 0.0125 | 33 |
| 102 | 0.00794 | 71 |
| 103 | 0.0105 | 200 |
| 104 | 0.0118 | 83 |
| 105 | 0.00343 | >350 |
| 106 | 0.0669 | 31 |
| 107 | 0.00257 | 5.4 |
| 108 | 0.0265 | 13.5 |
| 109 | 0.00282 | >350 |
| 110 | 0.00632 | 21 |
| 111 | 0.00532 | 281 |
| 112 | 0.00533 | 44 |
| 113 | 0.00852 | 28.4 |
| 114 | 0.00178 | 53 |
| 115 | 0.00711 | 58 |
| 116 | 0.00933 | 43 |
| 117 | 0.00509 | 37 |
| 118 | 0.013 | 77 |
| 119 | 0.0878 | 15 |
| 120 | 0.00231 | 45 |
| 121 | 0.00129 | 203 |
| 122 | 0.00542 | 15 |
| 123 | 0.00448 | 55 |
| 124 | 0.00203 | 14 |
| 125 | 0.00152 | 246 |
| 126 | 0.00114 | 257 |
| 127 | 0.00175 | 141 |
| 128 | 0.0819 | 26 |
| 129 | 0.000845 | 440 |
| 130 | 0.00312 | 352 |
| 131 | 0.00223 | 36 |
| 132 | 0.0224 | 10 |
| 133 | 0.0238 | 22 |
| 134 | 0.00356 | 10.9 |
| 135 | 0.0256 | 82 |
| 141 | 0.0636 | 9.4 |
| 143 | 0.0359 | 58 |
| 156 | 0.00286 | 42 |
| 159 | 0.873 | 1.4 |
| 160 | 0.0983 | 21 |
| 161 | 0.118 | 17.8 |
| 188 | 0.00869 | 0.18 |
| 197 | 0.00572 | 0.20 |
| 198 | 0.00388 | 0.27 |
| 199 | 0.728 | 0.95 |
| 200 | 0.716 | 0.97 |
| 201 | 0.00491 | 0.34 |

Example 902

Collagen Induced Arthritis Efficacy Test

The efficacy of Formula I compound inhibitors of PI3K delta to inhibit the induction and/or progression of collagen induced arthritis was tested in mice. DBA1/J male mice (Jackson Labs; 5-6 weeks of age) are acclimatized for one week and are then injected intra-dermally at the base of the tail with 0.1 ml of an emulsion of Bovine Type II Collagen (100 mg) and an equal volume of Complete Freunds Adjuvant (200 mg *Mycobacterium tuberculosis*). Three weeks later, mice are injected intra-dermally at the base of the tail with 0.1 ml of an emulsion of Bovine Type II Collagen (100 mg) and an equal volume of Incomplete Freunds Adjuvant for boost. Dosing generally starts as soon as animals display signs of joint inflammation or clinical score 1-2.

All mice are evaluated 2-3 times a week for arthritis using a macroscopic scoring system for each paw. At the end of the experiment clinical scores are obtained to evaluate the intensity of edema in the four paws. A score of 0 to 4 is assigned to each paw. Animals are scored 0 when no inflammatory signs (swelling and redness) are observed in any of the small joints (intraphalangeal, metacarpophalangeal, metatarsophalangeal) or large joints (wrist/carpus, ankle/tarsus). Animals are scored 1 when very slight to slight inflammation was observed (swelling and/or redness of paw or one digit), 2 moderate edema (swelling in two or more joint), 3 severe edema (gross swelling of the paw with more than two joints involved), and 4 when very severe edema (severe arthritis of the entire paw and digits) is present. The arthritic index for each mouse is evaluated by adding the four scores of the individual paws, giving a maximum score of 16. Plasma and serum samples are taken at 1 hour (orbital bleed) post dose and 24 hrs (cardiac puncture) post dose. Samples are stored at −20° C. until analysis. At termination, the hind paws are transected at the distal tibia, just proximal to the tarsal joint. The left and right hind paws are placed in the histology cassettes individually and fixed in 10% formalin. These paws are sent to histology dept for further process.

Materials: Bovine Type II collagen, immunization grade, 2 mg/ml (5 ml/vial) in 0.05 M acetic acid (solution), store at −20° C., from Chondrex, LLC, Seattle, Wash. Adjuvant complete H37 Ra, 6×10 ml/box, contains 1 mg/ml *Mycobacterium tuberculosis*. For use in animal immunological studies, for laboratory use, store at +4° C., from Difco Laboratories, Detroit, Mich. 48232-7058 USA. Adjuvant Incomplete H37 Ra, 6×10 ml/box: For use in animal immunological studies, for laboratory use, store at +4° C., from Difco Laboratories.

Example 903

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer tubes with sodium heparin.

Cynomolgus monkey blood is obtained courtesy of the LAT group from monkeys not previously exposed to, or after a washout period from, chemical dosing. Additional cyno blood draws may be collected during the course of pharmacokinetic or toxicology studies. Blood (25-30 mls for naïve monkeys or 3-4 mls from monkeys on studies requiring repeated draws) is collected by venipuncture into Vacutainer tubes with sodium heparin.

Solutions of Formula I compounds at 1000 or 2000 µM in PBS (20×), are diluted by three-fold serial dilutions in 10% DMSO in PBS for a nine point dose-response curve. An aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes. Goat F(ab')2 anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with florescent labeled antibodies for 30 minutes, at 37° C., 5% $CO_2$, 100% humidity. Include induced control, unstained and single stains for compensation adjustments and initial voltage settings. Samples are then lysed with Pharmingen Lyse according to the manufacturer's instructions. Samples are then transferred to a 96 well plate suitable to be run on the AMS 96 well system on the BD Calibur FACs machine. Data acquired and Mean Fluorescence Intensity values were obtained using Cell Quest Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The IC50 values are calculated by ActivityBase using Xlfit version 3, equation 201.

The IC50 values of selected compounds from Table 1 in the CD69 Whole Blood Assay include:

| Compound No. | IC50 (micromolar) |
|---|---|
| 105 | 0.0412 |
| 112 | 0.0838 |
| 114 | 0.012 |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A compound selected from Formula I:

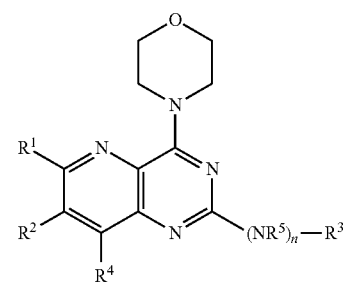

and stereoisomers, geometric isomers, tautomers, or pharmaceutically acceptable salts thereof, wherein $R^1$ is selected from F, Cl, Br, I, $N(R^2)_2$, $OR^2$, $SR^2$, $SOR^2$, $SO_2R^2$, $SO_2N(R^2)_2$, $C_1$-$C_{12}$ alkyl, $C_2$-$C_8$ alkenyl, $C_2$-$C_8$ alkynyl, $C_6$-$C_{20}$ aryl, $C_3$-$C_{12}$ carbocyclyl, $C_2$-$C_{20}$ heterocyclyl, $C_1$-$C_{20}$ heteroaryl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_2$-$C_{20}$ heterocyclyl)-($C_2$-$C_{20}$ heterocyclyl), —($C_1$-$C_{12}$ alkylene)-($C_2$-$C_{20}$ heterocyclyl)-($C_3$-$C_{12}$ carbocyclyl), —($C_1$-$C_{12}$ alkylene)-($C_2$-$C_{20}$ heterocyclyl)-C(=O)—($C_2$-$C_{20}$ heterocyclyl), —($C_1$-$C_{12}$ alkylene)-($C_1$-$C_{20}$ heteroaryl), —(C$_1$-C$_{12}$ alkylene)-(C$_2$-C$_{20}$ heterocyclyl)-(C$_1$-C$_{12}$ alkyl),
—(C$_1$-C$_{12}$ alkylene)-(C$_6$-C$_{20}$ aryl)-(C$_1$-C$_{12}$ alkyl),
—(C$_1$-C$_{12}$ alkylene)-(C$_1$-C$_{20}$ heteroaryl)-(C$_1$-C$_{12}$ alkyl),
—(C$_1$-C$_{12}$ alkylene)-C(=O)—(C$_2$-C$_{20}$ heterocyclyl),
—(C$_1$-C$_{12}$ alkylene)-N(R$^2$)$_2$,
—(C$_1$-C$_{12}$ alkylene)-NR$^2$C(=O)R$^2$,
—(C$_1$-C$_{12}$ alkylene)-NR$^2$—(C$_1$-C$_{12}$ alkyl),
—(C$_1$-C$_{12}$ alkylene)-N(C$_1$-C$_{12}$ alkyl)(C$_2$-C$_{20}$ heterocyclyl),
—(C$_1$-C$_{12}$ alkylene)-NR$^2$—(C$_1$-C$_{12}$ alkylene)-(C$_1$-C$_{20}$ heteroaryl),
—(C$_1$-C$_{12}$ alkylene)-NR$^2$—(C$_1$-C$_{12}$ alkylene)-(C$_1$-C$_{20}$ heterocyclyl),
—(C$_1$-C$_{12}$ alkylene)-NR$^2$—(C$_1$-C$_{12}$ alkylene)-NHC(=O)—(C$_1$-C$_{20}$ heteroaryl),
—(C$_1$-C$_{12}$ alkylene)-(C$_2$-C$_{20}$ heterocyclyl)-N(C$_1$-C$_{12}$ alkyl)R$^2$,
—(C$_1$-C$_{12}$ alkylene)-(C$_2$-C$_{20}$ heterocyclyl)-(C$_1$-C$_{12}$ alkyl)-N(C$_1$-C$_{12}$ alkyl)R$^2$,
—(C$_1$-C$_{12}$ alkylene)-NR$^2$—(C$_2$-C$_{20}$ heterocyclyl),
—(C$_2$-C$_{12}$ alkenylene)-(C$_2$-C$_{20}$ heterocyclyl),
—(C$_2$-C$_{20}$ heterocyclyl)-(C$_1$-C$_{12}$ alkyl),
—NR$^2$—(C$_2$-C$_{20}$ heterocyclyl),
—C(=O)—(C$_2$-C$_{20}$ heterocyclyl), and
—C(=O)—(C$_1$-C$_{12}$ alkyl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$CH$_3$, —CH$_2$CH(CH$_3$)$_2$, —CH$_2$OH, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CN, —CF$_3$, —CHF$_2$, —CO$_2$H, —COCH$_3$, —CO$_2$CH$_3$, —C(CH$_3$)$_2$CO$_2$CH$_3$, —CO$_2$C(CH$_3$)$_3$, —COCH(OH)CH$_3$, —COCH(CH$_3$)$_2$, —CONH$_2$, —CONHCH$_3$, —CON(CH$_3$)$_2$, —C(CH$_3$)$_2$CONH$_2$, —NO$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, =O, —OH, —OCH$_3$, —S(O)$_2$N(CH$_3$)$_2$, —SCH$_3$, —CH$_2$OCH$_3$, —S(O)$_2$CH$_3$, cyclopropyl, oxetanyl, and morpholino;

R$^2$ is H;
R$^3$ is selected from

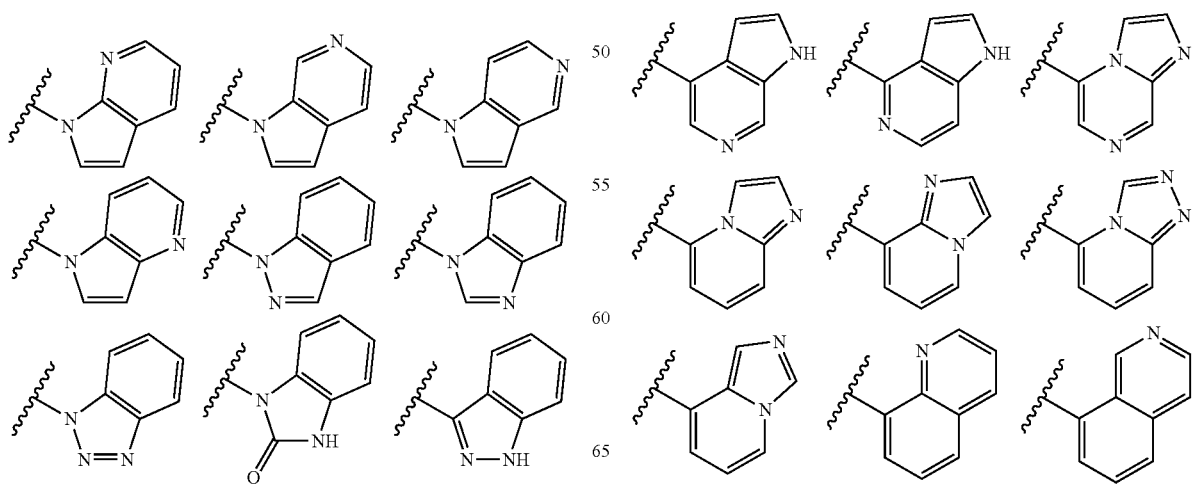

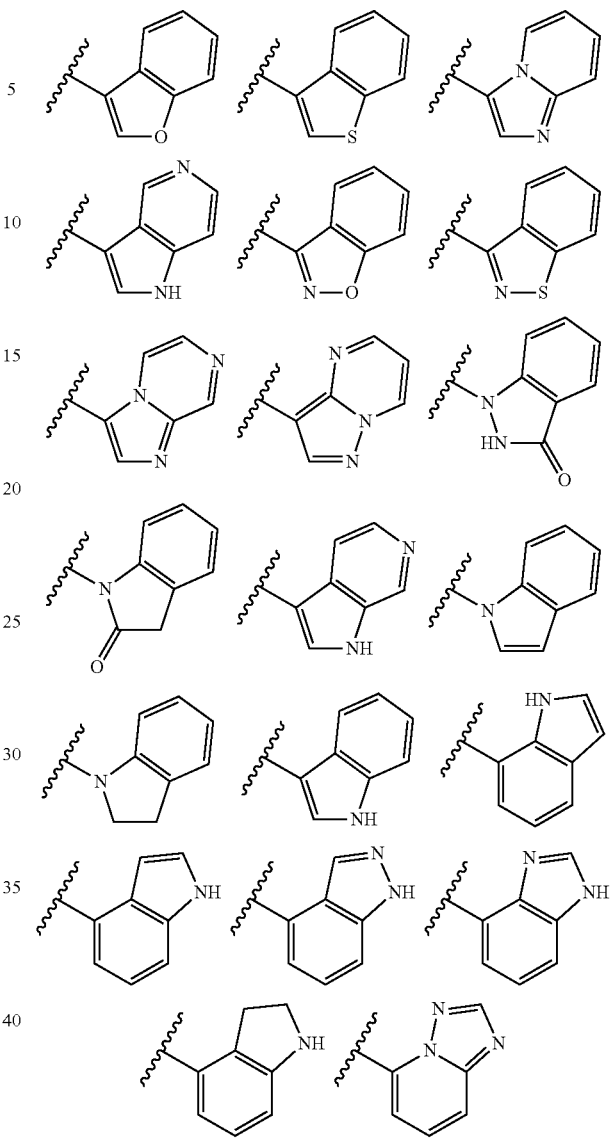

149

-continued

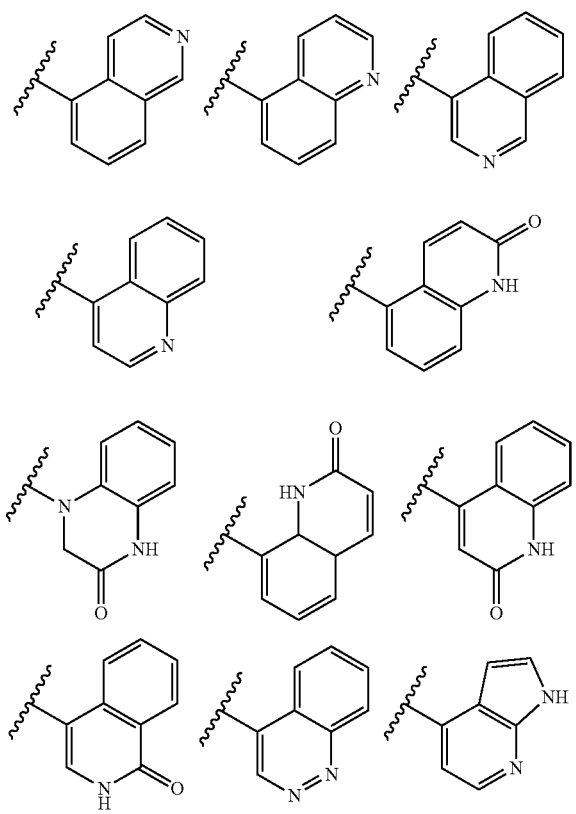

each of which are optionally substituted with one or more groups independently selected from F, Cl, Br, I, —CH$_3$, —CH$_2$CH$_3$, —CH$_2$CH$_2$CH$_3$, —CH(CH$_3$)$_2$, —C(CH$_3$)$_3$, —CH$_2$OCH$_3$, —CHF$_2$, —CN, —CF$_3$, —CH$_2$OH, —CH$_2$OCH$_3$, —CH$_2$CH$_2$OH, —CH$_2$C(CH$_3$)$_2$OH, —CH(CH$_3$)OH, —CH(CH$_2$CH$_3$)OH, —CH$_2$CH(OH)CH$_3$, —CH$_2$CH(OCH$_3$)CH$_3$, —C(CH$_3$)$_2$OH, —C(CH$_3$)$_2$OCH$_3$, —CH(CH$_3$)F, —C(CH$_3$)F$_2$, —CH(CH$_2$CH$_3$)F, —C(CH$_2$CH$_3$)$_2$F, —CO$_2$H, —CONH$_2$, —CON(CH$_2$CH)$_2$, —COCH$_3$, —CON(CH$_3$)$_2$, —NO$_2$, —NH$_2$, —NHCH$_3$, —N(CH$_3$)$_2$, —NHCH$_2$CH$_3$, —NHCH(CH$_3$)$_2$, —NHCH$_2$CH$_2$OH, —NHCH$_2$CH$_2$OCH$_3$, —NHCOCH$_3$, —NHCOCH$_2$CH$_3$, —NHCOCH$_2$OH, —NHS(O)$_2$CH$_3$, —N(CH$_3$)S(O)$_2$CH$_3$, =O, —OH, —OCH$_3$, —OCH$_2$CH$_3$, —OCH(CH$_3$)$_2$, —SH, —NHC(=O)NHCH$_3$, —NHC(=O)NHCH$_2$CH$_3$, —S(O)CH$_3$, —S(O)CH$_2$CH$_3$, —S(O)$_2$CH$_3$, —S(O)$_2$NH$_2$, —S(O)$_2$NHCH$_3$, —S(O)$_2$N(CH$_3$)$_2$, —CH$_2$S(O)$_2$CH$_3$, and a group selected from

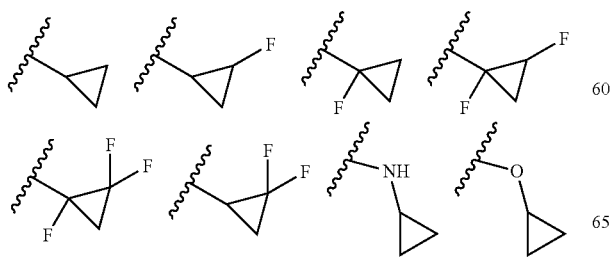

150

-continued

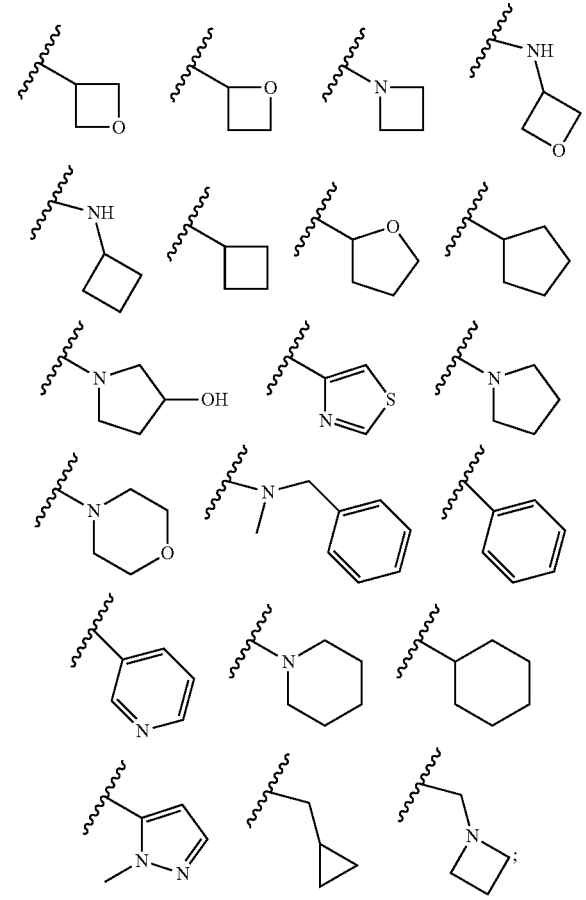

$R^4$ is H;

$R^5$ is selected from H, $C_1$-$C_{12}$ alkyl, $C_2$-$C_8$ alkenyl, $C_2$-$C_8$ alkynyl, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-C(=O)—($C_2$-$C_{20}$ heterocyclyl), —($C_1$-$C_{12}$ alkylene)-($C_6$-$C_{20}$ aryl), and —($C_1$-$C_{12}$ alkylene)-($C_1$-$C_{20}$ heteroaryl), where alkyl, alkenyl, alkynyl, alkylene, carbocyclyl, heterocyclyl, aryl, and heteroaryl are optionally substituted with one or more groups independently selected from F, Cl, Br, I, —CH$_3$, —CH$_2$OH, —CN, —CF$_3$, —CO$_2$H, —COCH$_3$, —CO$_2$CH$_3$, —CONH$_2$, —CONHCH$_3$, —CON(CH$_3$)$_2$, —NO$_2$, —NH$_2$, —NHCH$_3$, —NHCOCH$_3$, —NHS(O)$_2$CH$_3$, —OH, —OCH$_3$, —S(O)$_2$N(CH$_3$)$_2$, —SCH$_3$, —CH$_2$OCH$_3$, and —S(O)$_2$CH$_3$;

and n is 0 or 1.

2. The compound of claim 1 wherein $R^1$ is selected from the structures

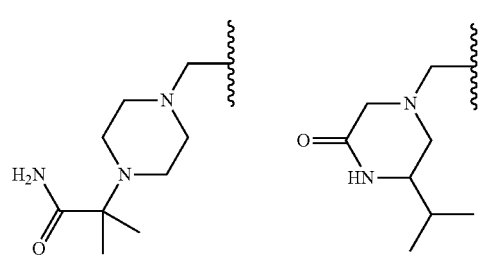

151
-continued
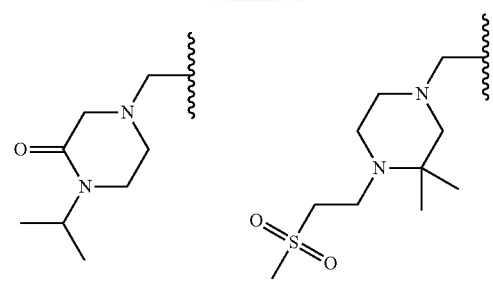
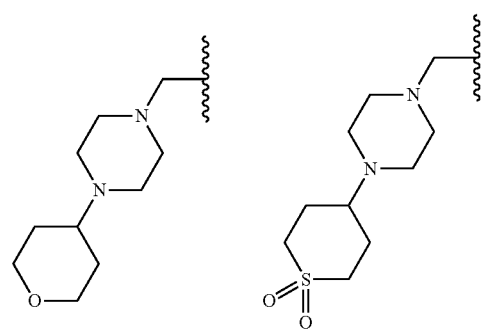
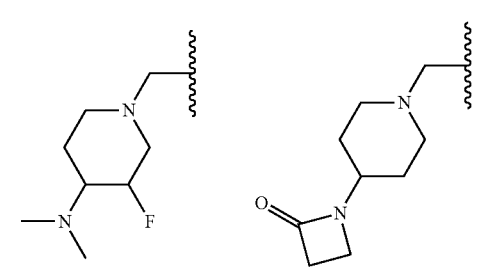
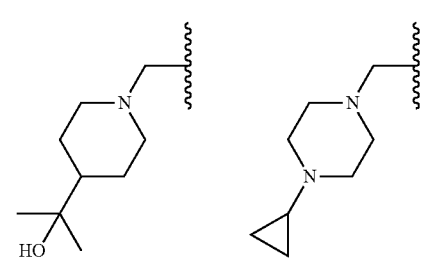
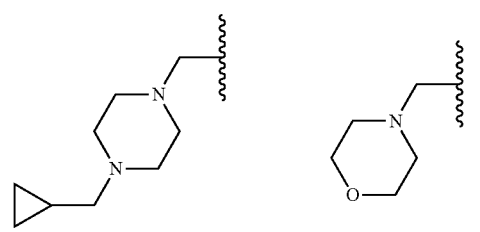
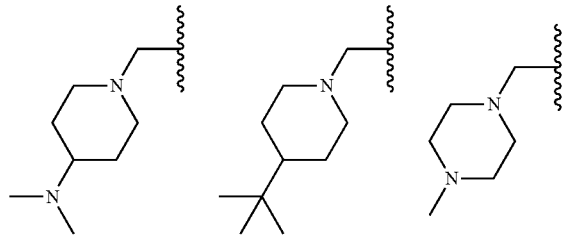
152
-continued
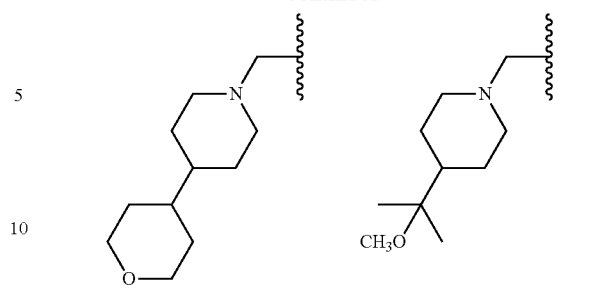
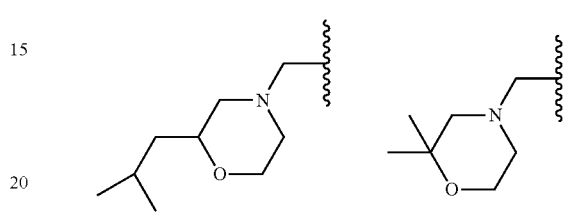
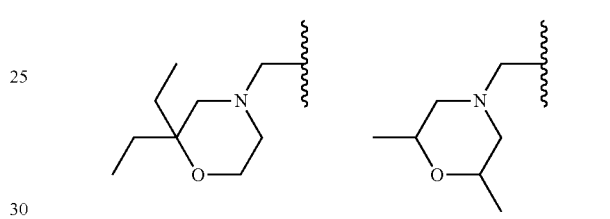
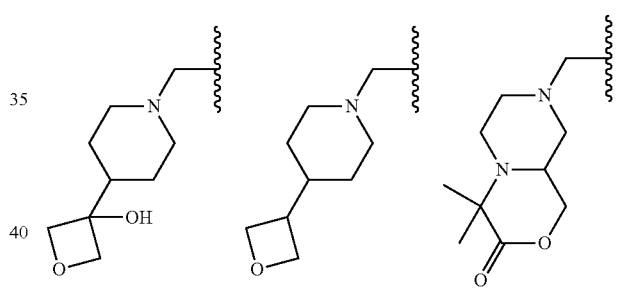
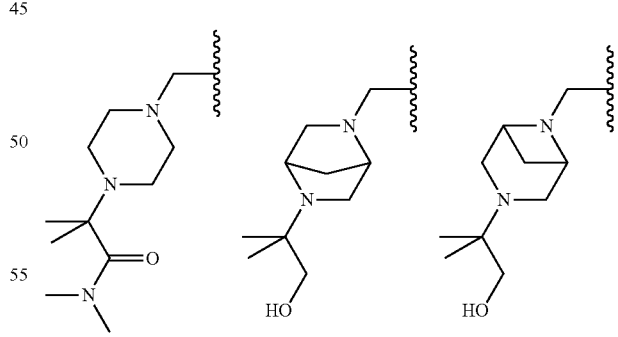
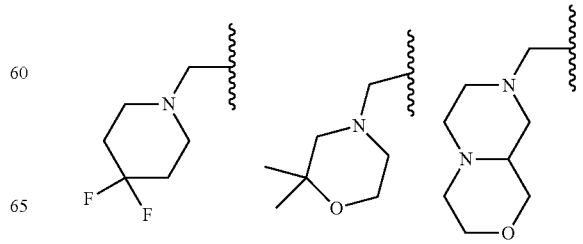

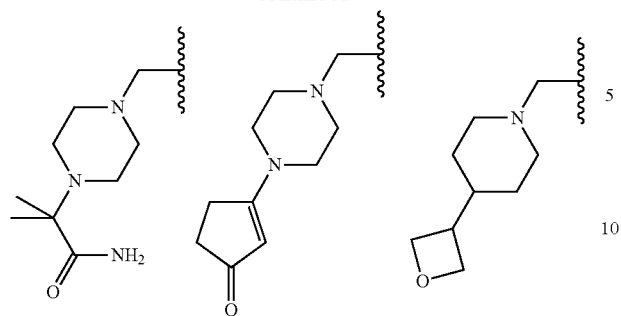
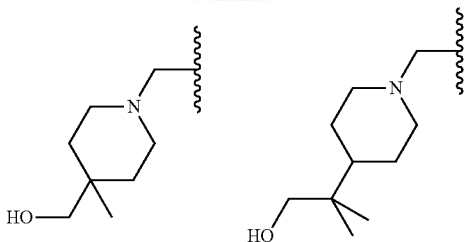
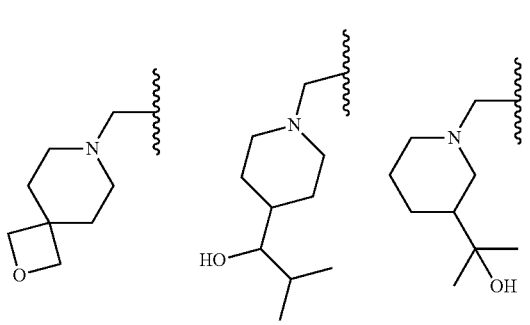
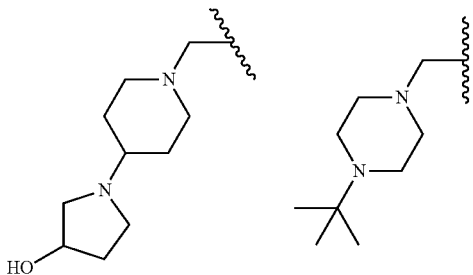
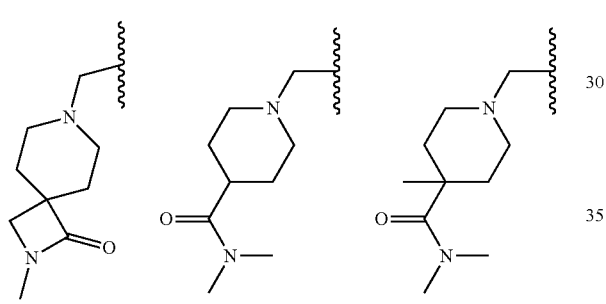
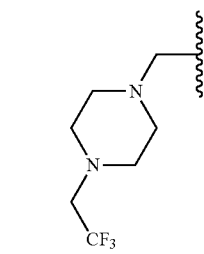
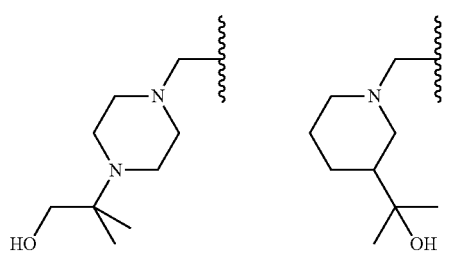
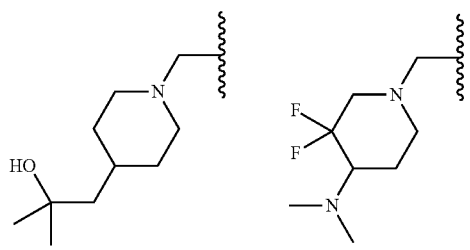
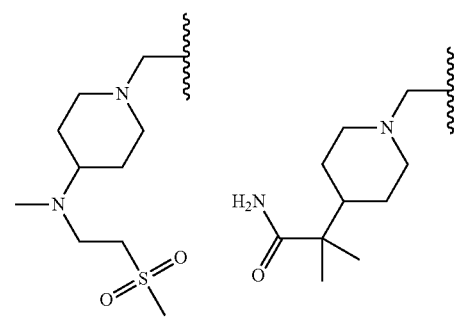
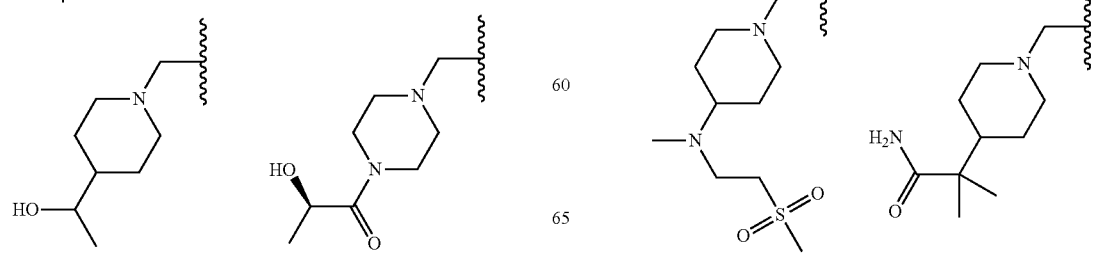

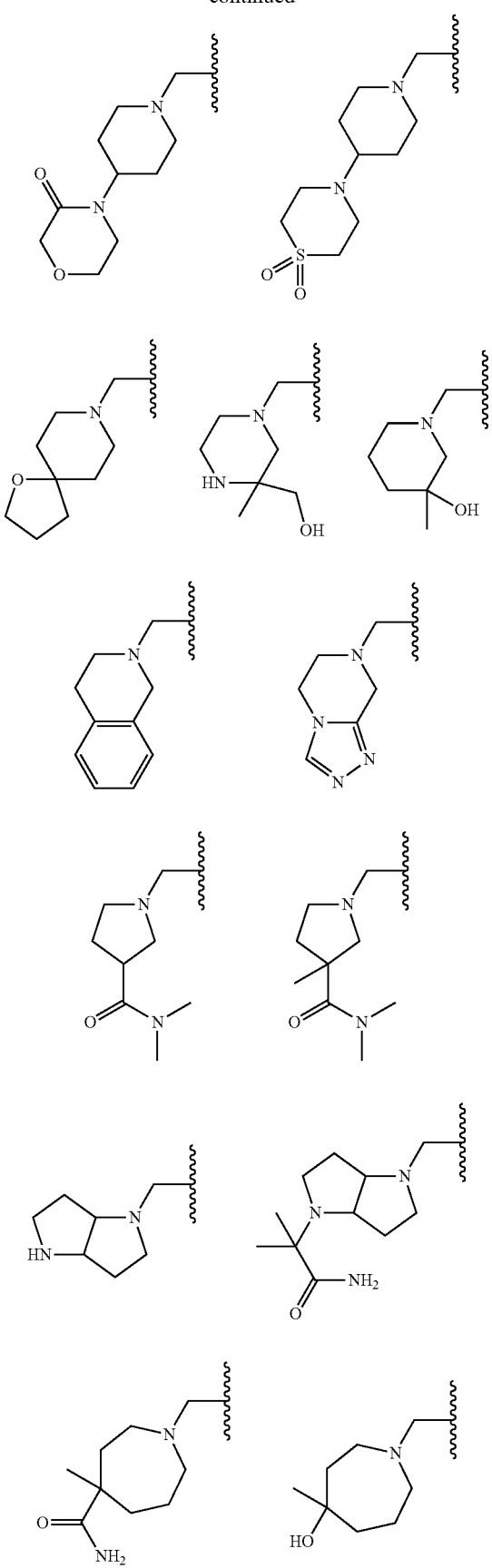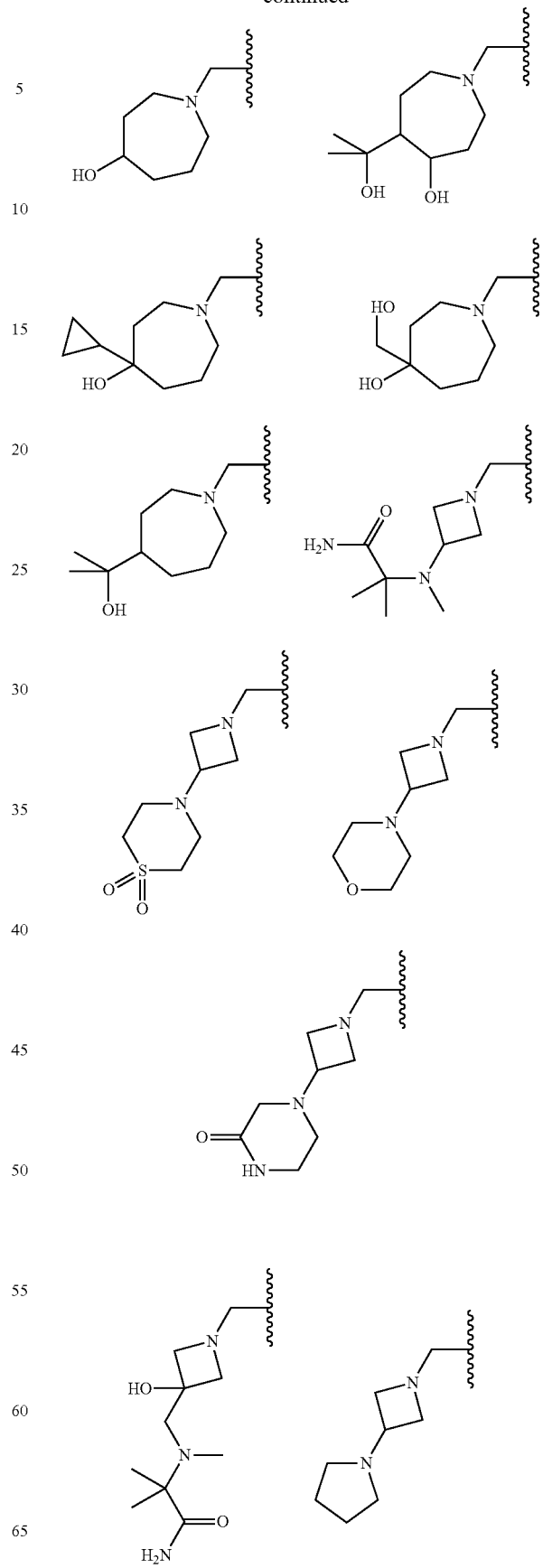

157
-continued
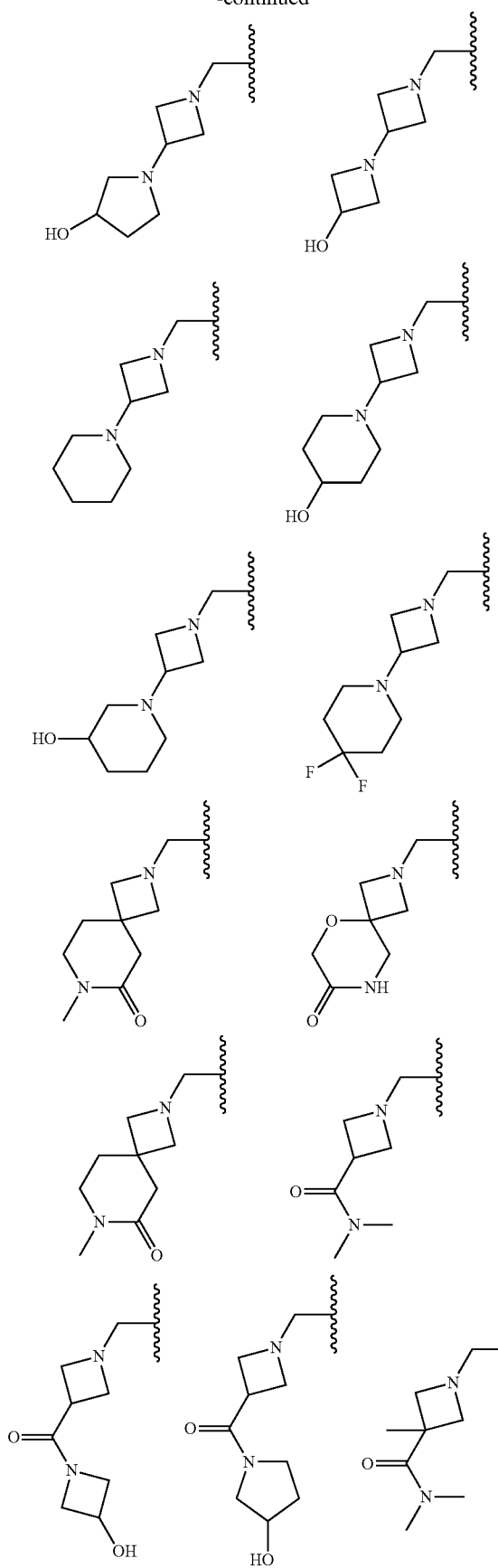
158
-continued
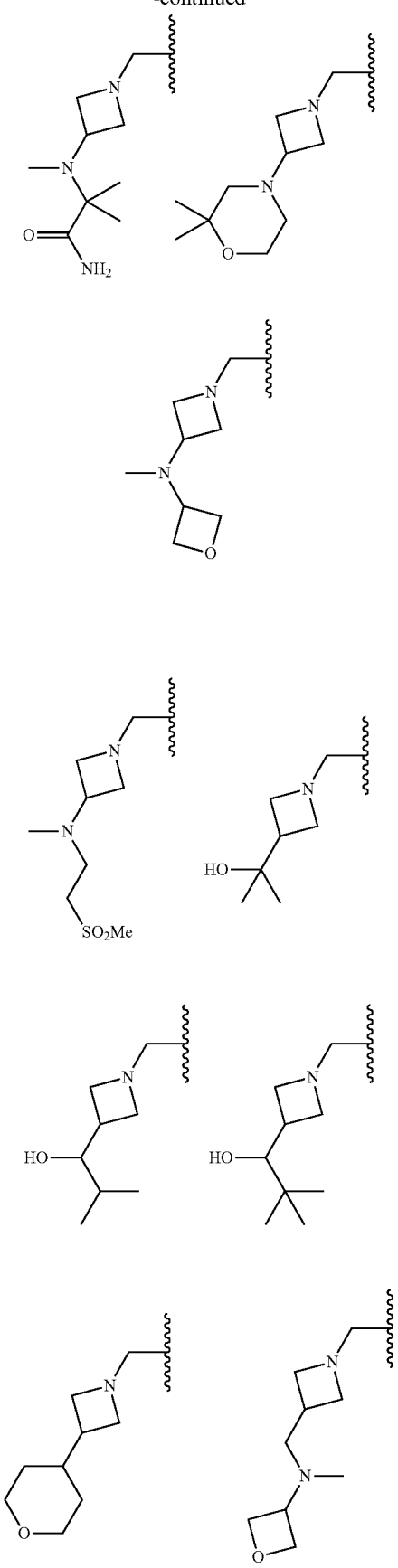

159
-continued
160
-continued
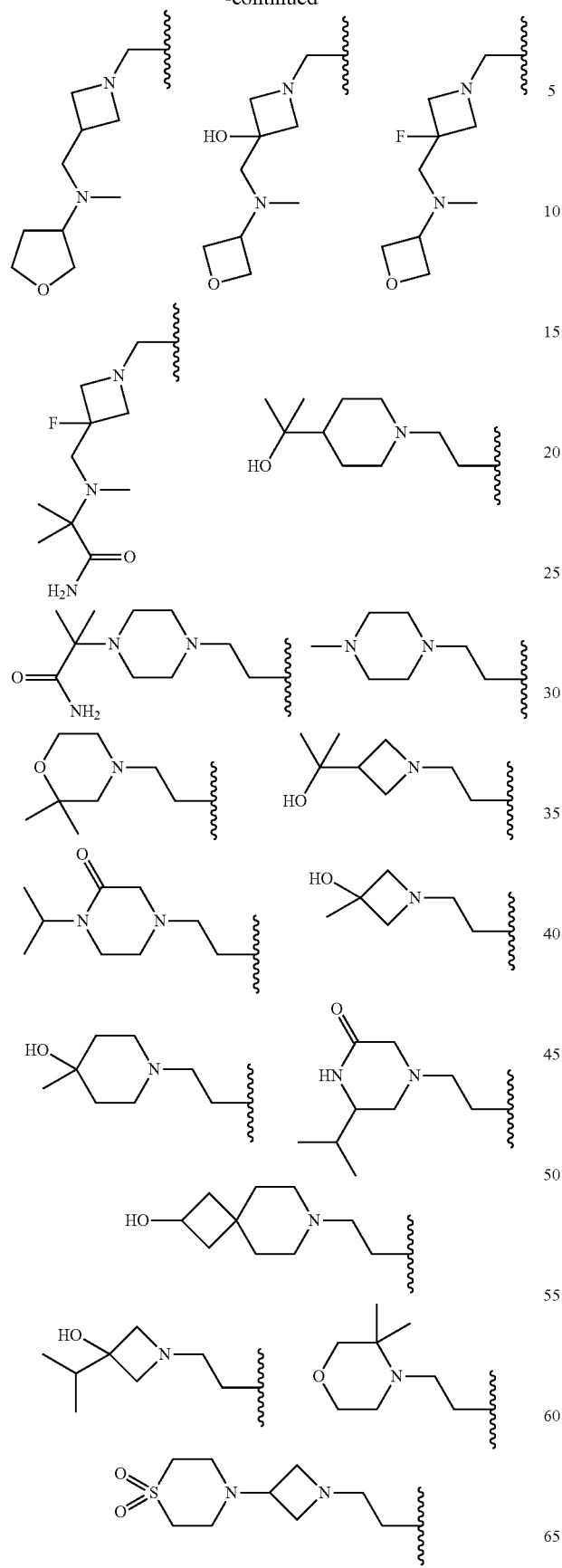
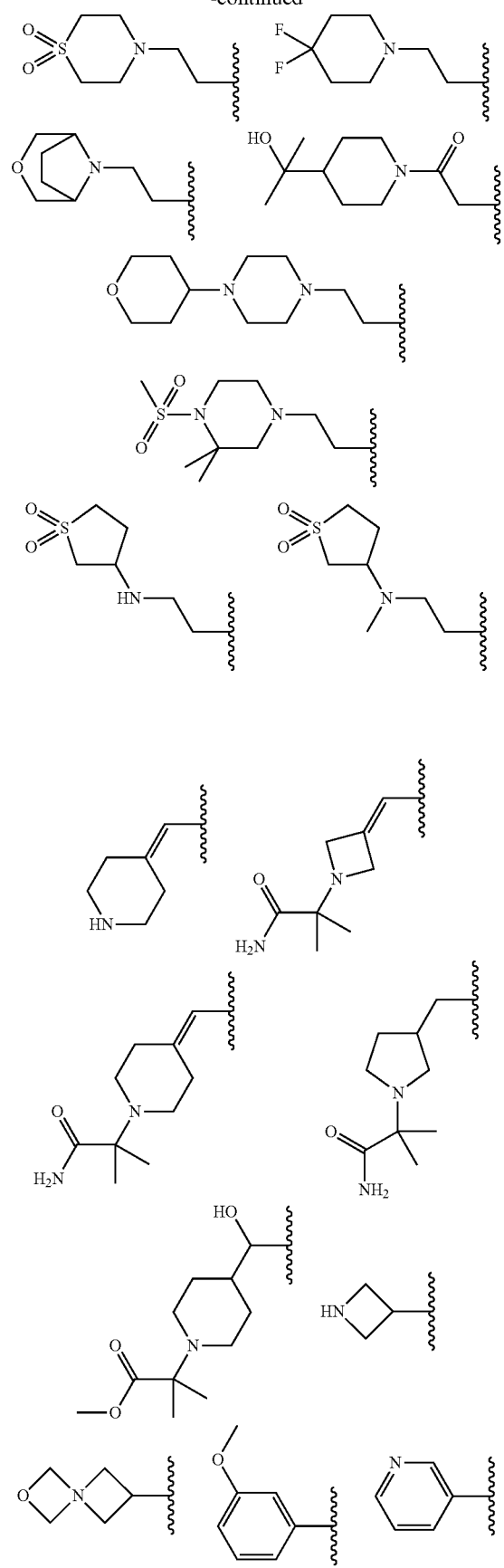

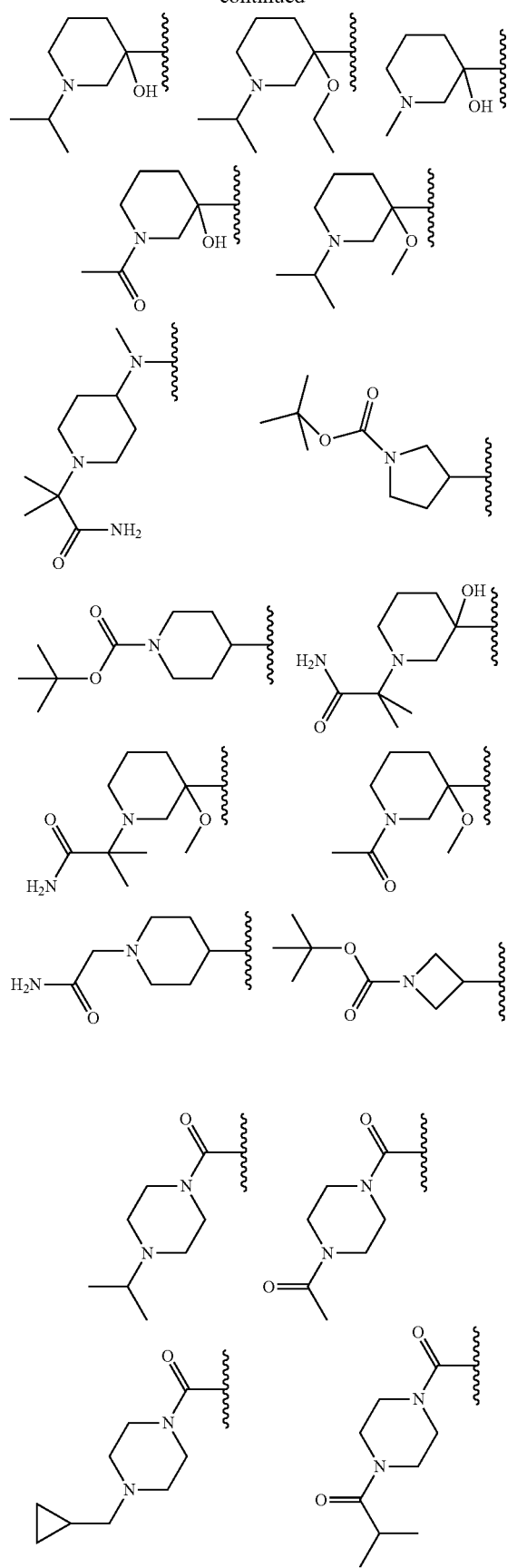
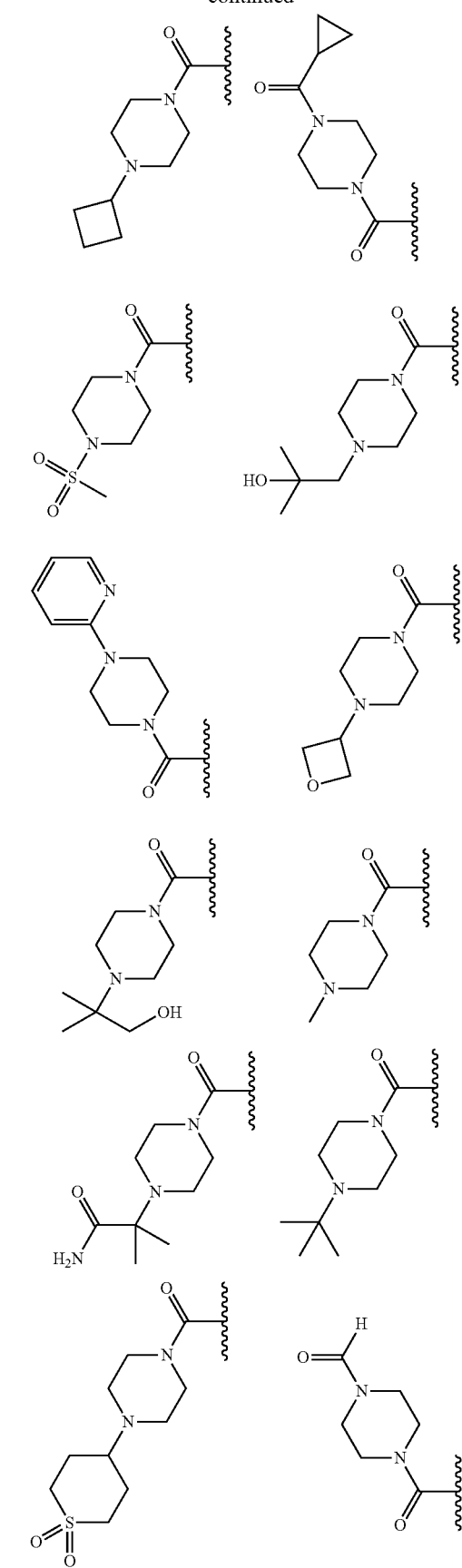

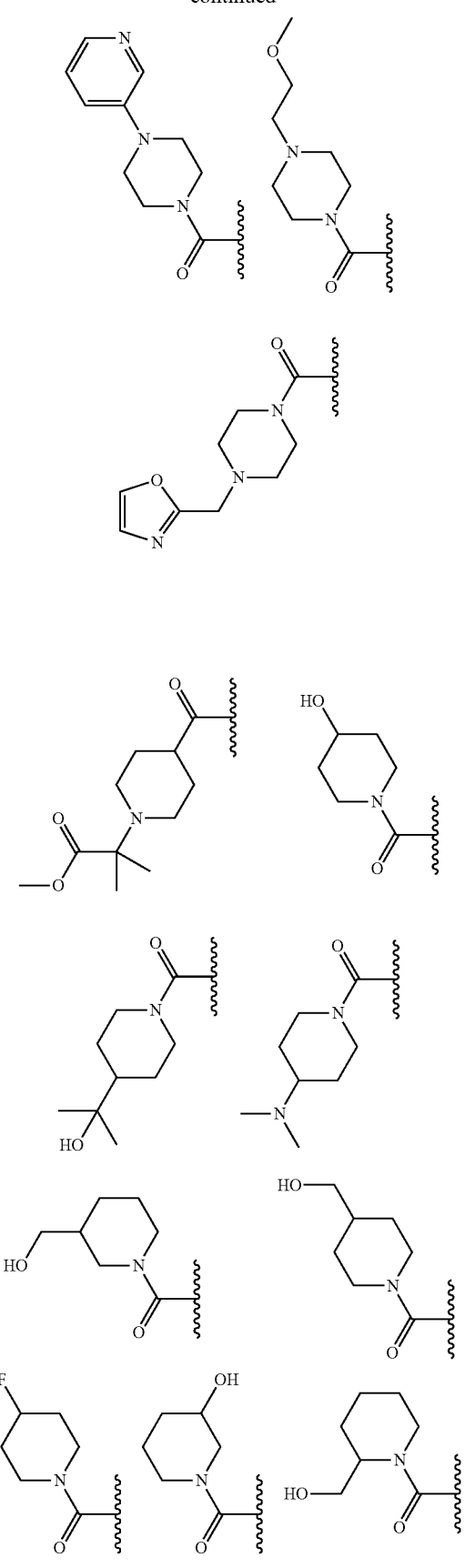
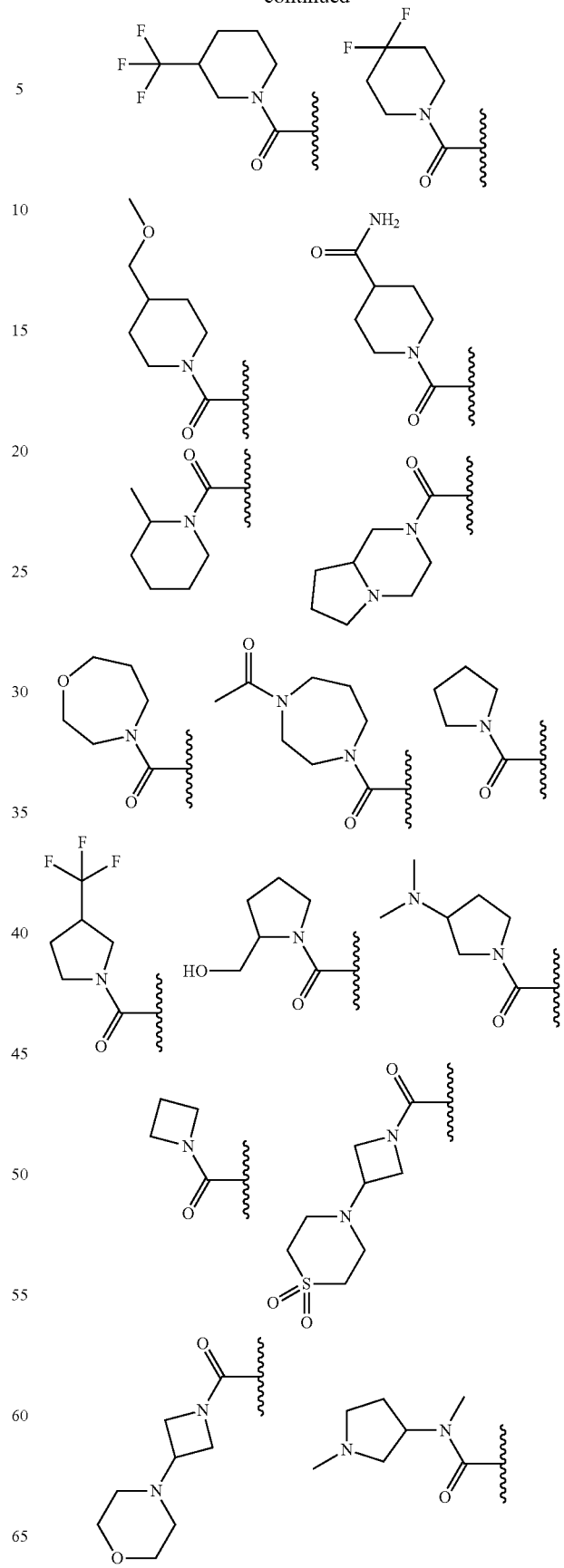

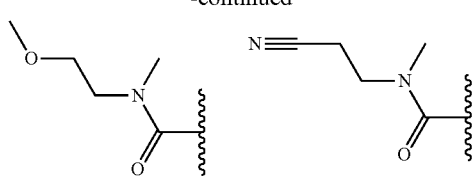
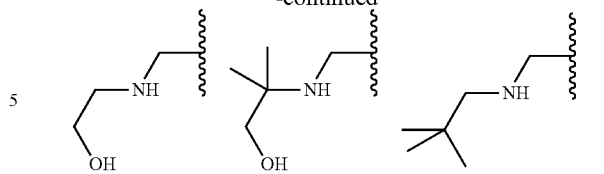
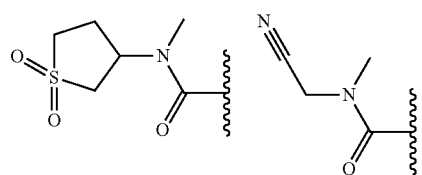
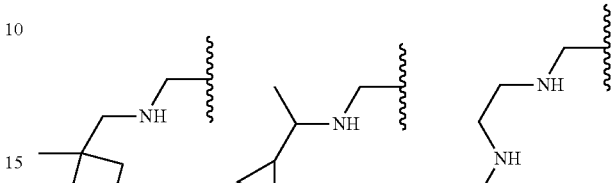
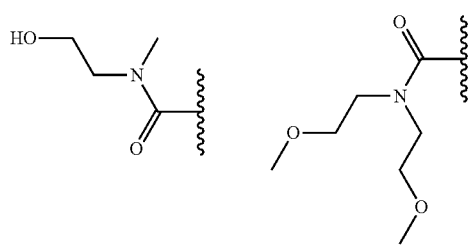
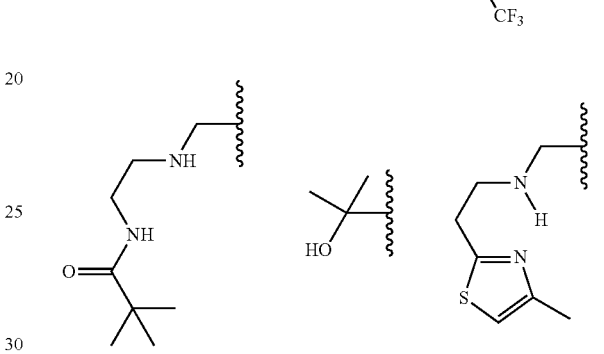
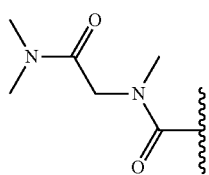
where the wavy line indicates the site of attachment.
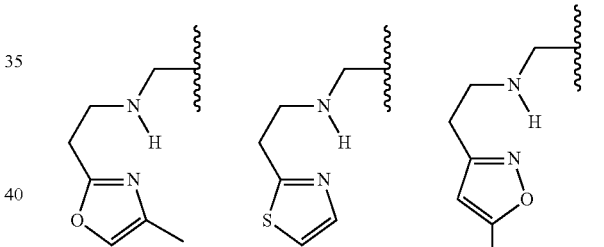
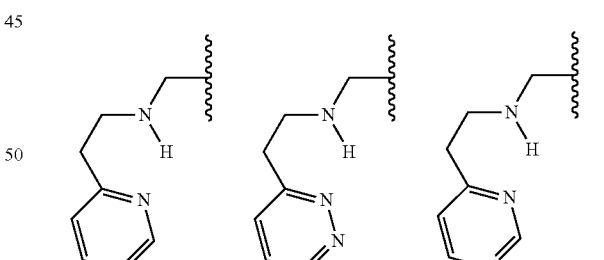
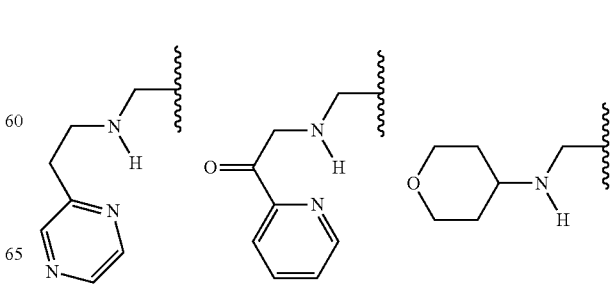

3. The compound of claim 1 wherein $R^3$ is selected from:

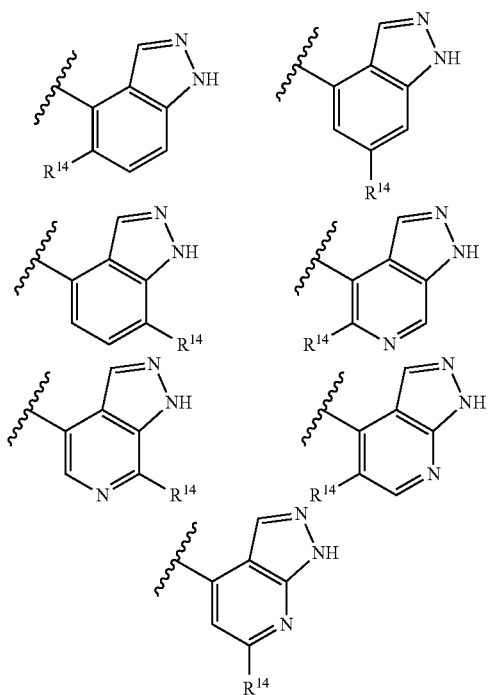

where the wavy line indicates the site of attachment and $R^{14}$ is selected from F, Cl, Br, I, —CH₃, —CN, —CF₃, —CH₂OH, —CO₂H, —CONH₂, —CON(CH₃)₂, —NO₂, —NH₂, —NHCH₃, —NHCOCH₃, —OH, —OCH₃, —SH, —NHC(=O)NHCH₃, —NHC(=O)NHCH₂CH₃, and —S(O)₂CH₃.

4. The compound of claim 1 wherein $R^3$ is 1H-indazol-4-yl and n is 0.

5. The compound of claim 1 selected from
2-(1-((2-(2-methyl-1H-benzo[d]imidazol-1-yl)-4-morpholinopyrido[3,2-d]pyrimidin-6-yl)methyl)piperidin-4-yl)propan-2-ol;
2-(1-((2-(2-cyclopropyl-1H-benzo[d]imidazol-1-yl)-4-morpholinopyrido[3,2-d]pyrimidin-6-yl)methyl)piperidin-4-yl)propan-2-ol;
2-(1-((2-(2-methylbenzofuran-3-yl)-4-morpholinopyrido[3,2-d]pyrimidin-6-yl)methyl)piperidin-4-yl)propan-2-ol;
2-ethyl-1-(6-((4-(2-hydroxypropan-2-yl)piperidin-1-yl)methyl)-4-morpholinopyrido[3,2-d]pyrimidin-2-yl)-1H-indazol-3(2H)-one;
2-(1-((2-(5-fluoro-1H-indol-4-yl)-4-morpholinopyrido[3,2-d]pyrimidin-6-yl)methyl)piperidin-4-yl)propan-2-ol;
(2-(5-fluoro-1H-indol-4-yl)-4-morpholinopyrido[3,2-d]pyrimidin-6-yl)methanol;
2-(1-((2-(1H-indol-4-yl)-4-morpholinopyrido[3,2-d]pyrimidin-6-yl)methyl)piperidin-4-yl)propan-2-ol;
2-(1-((2-(1H-indazol-4-yl)-4-morpholinopyrido[3,2-d]pyrimidin-6-yl)methyl)piperidin-4-yl)propan-2-ol;
4-(2-(5-fluoro-1H-indol-4-yl)-6-((3-(tetrahydro-2H-pyran-4-yl)azetidin-1-yl)methyl)pyrido[3,2-d]pyrimidin-4-yl)morpholine;
2-(1-((2-(2-isopropyl-1H-benzo[d]imidazol-1-yl)-4-morpholinopyrido[3,2-d]pyrimidin-6-yl)methyl)piperidin-4-yl)propan-2-ol;
4-(2-(2-isopropyl-1H-benzo[d]imidazol-1-yl)-6-((3-(tetrahydro-2H-pyran-4-yl)azetidin-1-yl)methyl)pyrido[3,2-d]pyrimidin-4-yl)morpholine;
(S)-2-(1-((2-(2-(1-methoxyethyl)-1H-benzo[d]imidazol-1-yl)-4-morpholinopyrido[3,2-d]pyrimidin-6-yl)methyl)piperidin-4-yl)propan-2-ol;
(R)-2-(1-((2-(2-(1-methoxyethyl)-1H-benzo[d]imidazol-1-yl)-4-morpholinopyrido[3,2-d]pyrimidin-6-yl)methyl)piperidin-4-yl)propan-2-ol;
methyl 2-(3-((2-(2-isopropyl-1H-benzo[d]imidazol-1-yl)-4-morpholinopyrido[3,2-d]pyrimidin-6-yl)methyl)azetidin-1-yl)-2-methylpropanoate;
(2-(5-fluoro-1H-indol-4-yl)-4-morpholinopyrido[3,2-d]pyrimidin-6-yl)(4-(2-hydroxypropan-2-yl)piperidin-1-yl)methanone;
(4-(2-hydroxypropan-2-yl)piperidin-1-yl)(2-(2-isopropyl-1H-benzo[d]imidazol-1-yl)-4-morpholinopyrido[3,2-d]pyrimidin-6-yl)methanone;
2-(1-((2-(2-(1,1-difluoroethyl)-1H-benzo[d]imidazol-1-yl)-4-morpholinopyrido[3,2-d]pyrimidin-6-yl)methyl)piperidin-4-yl)propan-2-ol;
2-(4-((2-(5-fluoro-1H-indol-4-yl)-4-morpholinopyrido[3,2-d]pyrimidin-6-yl)methyl)piperazin-1-yl)-2-methylpropanamide;
2-(4-((2-(1H-indol-3-yl)-4-morpholinopyrido[3,2-d]pyrimidin-6-yl)methyl)piperazin-1-yl)-2-methylpropanamide;
4-(6-((3-(4,4-difluoropiperidin-1-yl)azetidin-1-yl)methyl)-2-(5-fluoro-1H-indol-4-yl)pyrido[3,2-d]pyrimidin-4-yl)morpholine;
4-(1-((2-(5-fluoro-1H-indol-4-yl)-4-morpholinopyrido[3,2-d]pyrimidin-6-yl)methyl)azetidin-3-yl)morpholine;
4-(1-((2-(5-fluoro-1H-indol-4-yl)-4-morpholinopyrido[3,2-d]pyrimidin-6-yl)methyl)azetidin-3-yl)piperazin-2-one;
2-(1-((2-(1H-indol-1-yl)-4-morpholinopyrido[3,2-d]pyrimidin-6-yl)methyl)piperidin-4-yl)propan-2-ol;
4-(2-(5-fluoro-1H-indol-4-yl)-6-((3-(1,1-dioxo)thiomorpholinoazetidin-1-yl)methyl)pyrido[3,2-d]pyrimidin-4-yl)morpholine;
4-(2-(5-fluoro-1H-indol-4-yl)-6-((4-(oxetan-3-yl)piperidin-1-yl)methyl)pyrido[3,2-d]pyrimidin-4-yl)morpholine;
4-(1-((2-(2-ethyl-1H-benzo[d]imidazol-1-yl)-4-morpholinopyrido[3,2-d]pyrimidin-6-yl)methyl)azetidin-3-yl)morpholine;
2-(1-((2-(1H-indol-3-yl)-4-morpholinopyrido[3,2-d]pyrimidin-6-yl)methyl)piperidin-4-yl)propan-2-ol; and
4-(1-((2-(2-ethyl-1H-benzo[d]imidazol-1-yl)-4-morpholinopyrido[3,2-d]pyrimidin-6-yl)methyl)azetidin-3-yl)piperazin-2-one.

6. The compound of claim 1 selected from
2-(1-((2-(2-methyl-1H-indol-1-yl)-4-morpholinopyrido[3,2-d]pyrimidin-6-yl)methyl)piperidin-4-yl)propan-2-ol;
2-(1-((2-(2-ethyl-2H-indazol-3-yl)-4-morpholinopyrido[3,2-d]pyrimidin-6-yl)methyl)piperidin-4-yl)propan-2-ol;
tert-butyl 4-((2-(5-fluoro-1H-indol-4-yl)-4-morpholinopyrido[3,2-d]pyrimidin-6-yl)methyl)piperidine-1-carboxylate;
2-(1-((2-(1H-indazol-3-yl)-4-morpholinopyrido[3,2-d]pyrimidin-6-yl)methyl)piperidin-4-yl)propan-2-ol;
4-(2-(5-fluoro-1H-indol-4-yl)-6-(piperidin-4-ylmethyl)pyrido[3,2-d]pyrimidin-4-yl)morpholine;

1-(((2-(5-fluoro-1H-indol-4-yl)-4-morpholinopyrido[3,2-d]pyrimidin-6-yl)methyl)(methyl)amino)-2-methylpropan-2-ol;
4-(2-(5-fluoro-1H-indol-4-yl)-6-(1-isopropyl-1H-1,2,4-triazol-5-yl)pyrido[3,2-d]pyrimidin-4-yl)morpholine;
N-((2-(5-fluoro-1H-indol-4-yl)-4-morpholinopyrido[3,2-d]pyrimidin-6-yl)methyl)tetrahydro-2H-pyran-4-amine;
1-((2-(5-fluoro-1H-indol-4-yl)-4-morpholinopyrido[3,2-d]pyrimidin-6-yl)methylamino)-2-methylpropan-2-ol;
4-(6-((3,3-dimethylpyrrolidin-1-yl)methyl)-2-(5-fluoro-1H-indol-4-yl)pyrido[3,2-d]pyrimidin-4-yl)morpholine;
N-((2-(5-fluoro-1H-indol-4-yl)-4-morpholinopyrido[3,2-d]pyrimidin-6-yl)methyl)pivalamide;
4-((2-(5-fluoro-1H-indol-4-yl)-4-morpholinopyrido[3,2-d]pyrimidin-6-yl)methyl)morpholine;
N-((2-(5-fluoro-1H-indol-4-yl)-4-morpholinopyrido[3,2-d]pyrimidin-6-yl)methyl)isobutyramide;
1-(4-((2-(5-fluoro-1H-indol-4-yl)-4-morpholinopyrido[3,2-d]pyrimidin-6-yl)methyl)piperidin-1-yl)ethanone;
1-(4-((2-(5-fluoro-1H-indol-4-yl)-4-morpholinopyrido[3,2-d]pyrimidin-6-yl)methyl)piperidin-1-yl)-2-methylpropan-1-one;
(S)-4-(1-((2-(2-(1-methoxyethyl)-1H-benzo[d]imidazol-1-yl)-4-morpholinopyrido[3,2-d]pyrimidin-6-yl)methyl)azetidin-3-yl)morpholine;
2-(1-((2-(2-(dimethylamino)-1H-benzo[d]imidazol-1-yl)-4-morpholinopyrido[3,2-d]pyrimidin-6-yl)methyl)piperidin-4-yl)propan-2-ol;
4-(2-(5-fluoro-1H-indol-4-yl)-6-((tetrahydro-2H-pyran-4-yl)methyl)pyrido[3,2-d]pyrimidin-4-yl)morpholine;
2-(1-((4-morpholino-2-(2-(trifluoromethyl)-1H-benzo[d]imidazol-1-yl)pyrido[3,2-d]pyrimidin-6-yl)methyl)piperidin-4-yl)propan-2-ol;
2-(1-((2-(2-(difluoromethyl)-1H-benzo[d]imidazol-1-yl)-4-morpholinopyrido[3,2-d]pyrimidin-6-yl)methyl)piperidin-4-yl)propan-2-ol;
2-(1-(6-((4-(2-hydroxypropan-2-yl)piperidin-1-yl)methyl)-4-morpholinopyrido[3,2-d]pyrimidin-2-yl)-1H-benzo[d]imidazol-2-yl)acetonitrile;
2-(1-((2-(imidazo[1,2-a]pyridin-5-yl)-4-morpholinopyrido[3,2-d]pyrimidin-6-yl)methyl)piperidin-4-yl)propan-2-ol;
N,N-dimethyl-1-(4-morpholino-6-((3-(1,1-dioxo)thiomorpholinoazetidin-1-yl)methyl)pyrido[3,2-d]pyrimidin-2-yl)-1H-benzo[d]imidazol-2-amine;
(S)-1-(4-((2-(2-(1-methoxyethyl)-1H-benzo[d]imidazol-1-yl)-4-morpholinopyrido[3,2-d]pyrimidin-6-yl)methyl)piperidin-1-yl)ethanone;
1-(4-((2-(2-(dimethylamino)-1H-benzo[d]imidazol-1-yl)-4-morpholinopyrido[3,2-d]pyrimidin-6-yl)methyl)piperidin-1-yl)ethanone;
2-(1-((2-([1,2,4]triazolo[1,5-a]pyridin-5-yl)-4-morpholinopyrido[3,2-d]pyrimidin-6-yl)methyl)piperidin-4-yl)propan-2-ol;
N,N-dimethyl-1-(4-morpholino-6-((3-morpholinoazetidin-1-yl)methyl)pyrido[3,2-d]pyrimidin-2-yl)-1H-benzo[d]imidazol-2-amine;
2-(1-((2-(2-(2-hydroxyethyl)-1H-benzo[d]imidazol-1-yl)-4-morpholinopyrido[3,2-d]pyrimidin-6-yl)methyl)piperidin-4-yl)propan-2-ol;
4-(2-(2-(difluoromethyl)-1H-benzo[d]imidazol-1-yl)-6-((3-(1,1-dioxo)thiomorpholinoazetidin-1-yl)methyl)pyrido[3,2-d]pyrimidin-4-yl)morpholine;
2-(1-((2-(2-methoxy-1H-benzo[d]imidazol-1-yl)-4-morpholinopyrido[3,2-d]pyrimidin-6-yl)methyl)piperidin-4-yl)propan-2-ol;
1-(4-((2-(2-(difluoromethyl)-1H-benzo[d]imidazol-1-yl)-4-morpholinopyrido[3,2-d]pyrimidin-6-yl)methyl)piperidin-1-yl)ethanone;
4-(1-((2-(2-(difluoromethyl)-1H-benzo[d]imidazol-1-yl)-4-morpholinopyrido[3,2-d]pyrimidin-6-yl)methyl)azetidin-3-yl)morpholine;
2-(1-((4-morpholino-2-(2-(2,2,2-trifluoroethyl)-1H-benzo[d]imidazol-1-yl)pyrido[3,2-d]pyrimidin-6-yl)methyl)piperidin-4-yl)propan-2-ol;
2-(1-((2-(2-(azetidin-1-yl)-1H-benzo[d]imidazol-1-yl)-4-morpholinopyrido[3,2-d]pyrimidin-6-yl)methyl)piperidin-4-yl)propan-2-ol;
2-(1-((4-morpholino-2-(2-(pyrrolidin-1-yl)-1H-benzo[d]imidazol-1-yl)pyrido[3,2-d]pyrimidin-6-yl)methyl)piperidin-4-yl)propan-2-ol;
4-(1-((2-(1H-benzo[d]imidazol-4-yl)-4-morpholinopyrido[3,2-d]pyrimidin-6-yl)methyl)azetidin-3-yl)morpholine; and
4-(1-((2-(2-methyl-1H-benzo[d]imidazol-4-yl)-4-morpholinopyrido[3,2-d]pyrimidin-6-yl)methyl)azetidin-3-yl)morpholine.

7. A pharmaceutical composition comprised of a compound of claim 1 and a pharmaceutically acceptable carrier, glidant, diluent, or excipient.

8. The pharmaceutical composition according to claim 7, further comprising a chemotherapeutic agent.

9. A kit for treating a condition mediated by the p110 delta isoform of PI3 kinase comprising a first pharmaceutical composition of claim 7; and instructions for use.

* * * * *